US010175195B2

(12) United States Patent
Bashir et al.

(10) Patent No.: US 10,175,195 B2
(45) Date of Patent: Jan. 8, 2019

(54) NANOPORE SENSORS FOR BIOMOLECULAR CHARACTERIZATION

(75) Inventors: Rashid Bashir, Champaign, IL (US); Bala Murali Venkatesan, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 480 days.

(21) Appl. No.: 14/234,590

(22) PCT Filed: Jul. 26, 2012

(86) PCT No.: PCT/US2012/048248
§ 371 (c)(1),
(2), (4) Date: Jan. 23, 2014

(87) PCT Pub. No.: WO2013/016486
PCT Pub. Date: Jan. 31, 2013

(65) Prior Publication Data
US 2014/0174927 A1  Jun. 26, 2014

Related U.S. Application Data

(60) Provisional application No. 61/512,095, filed on Jul. 27, 2011.

(51) Int. Cl.
*G01N 27/447* (2006.01)
*C12Q 1/6827* (2018.01)
*G01N 33/487* (2006.01)

(52) U.S. Cl.
CPC ..... *G01N 27/44791* (2013.01); *C12Q 1/6827* (2013.01); *G01N 27/447* (2013.01); *G01N 33/48721* (2013.01)

(58) Field of Classification Search
CPC ................. G01N 33/48721; G01N 33/48728
See application file for complete search history.

(56) References Cited

U.S. PATENT DOCUMENTS 2,656,508 A   10/1953  Coulter
5,795,782 A   8/1998   Church et al.
(Continued)

FOREIGN PATENT DOCUMENTS

WO   WO 2010/080617   7/2010
WO   WO 2011/047582   4/2011

OTHER PUBLICATIONS

Akeson et al. (1999) "Microsecond Time-Scale Discrimination Among Polycytidylic Acid, Polyadenylic Acid, and Polyuridylic Acid as Homopolymers or as Segments Within Single RNA Molecules," *Biophys. J.* 77:3227-3233.
(Continued)

*Primary Examiner* — Bach T Dinh
(74) *Attorney, Agent, or Firm* — Leydig, Voit & Mayer, Ltd.

(57) ABSTRACT

Provided herein are methods and devices for characterizing a biomolecule parameter by a nanopore-containing membrane, and also methods for making devices that can be used in the methods and devices provided herein. The nanopore membrane is a multilayer stack of conducting layers and dielectric layers, wherein an embedded conducting layer or conducting layer gates provides well-controlled and measurable electric fields in and around the nanopore through which the biomolecule translocates. In an aspect, the conducting layer is graphene.

4 Claims, 25 Drawing Sheets

(56) References Cited

U.S. PATENT DOCUMENTS

| | | | |
|---|---|---|---|
| 6,616,895 | B2 | 9/2003 | Dugas et al. |
| 7,468,271 | B2 | 12/2008 | Golovchenko et al. |
| 7,846,738 | B2 | 12/2010 | Golovchenko et al. |
| 7,947,454 | B2 | 5/2011 | Akeson et al. |
| 8,945,912 | B2 | 2/2015 | Bashir et al. |
| 2005/0019784 | A1 | 10/2005 | Su et al. |
| 2006/0231419 | A1* | 10/2006 | Barth .................. B82Y 5/00 |
| | | | 205/775 |
| 2007/0190542 | A1 | 8/2007 | Ling et al. |
| 2007/0269825 | A1 | 11/2007 | Wang et al. |
| 2008/0187915 | A1* | 8/2008 | Polonsky ............. B82Y 15/00 |
| | | | 435/6.13 |
| 2008/0280776 | A1 | 11/2008 | Bashir et al. |
| 2010/0078325 | A1* | 4/2010 | Oliver ............ G01N 33/48721 |
| | | | 204/452 |
| 2010/0327255 | A1 | 12/2010 | Peng et al. |
| 2010/0327847 | A1 | 12/2010 | Leiber et al. |
| 2010/0327956 | A1 | 12/2010 | Karkkainen et al. |
| 2011/0086352 | A1 | 4/2011 | Bashir et al. |
| 2011/0168551 | A1 | 7/2011 | White et al. |
| 2011/0226623 | A1 | 9/2011 | Timp et al. |
| 2011/0236984 | A1* | 9/2011 | Sun .................... C12Q 1/6869 |
| | | | 436/94 |
| 2012/0003438 | A1 | 1/2012 | Appleton et al. |
| 2012/0037919 | A1 | 2/2012 | Xu et al. |
| 2012/0040343 | A1 | 2/2012 | Timp et al. |
| 2013/0146480 | A1* | 6/2013 | Garaj ............. G01N 33/48721 |
| | | | 205/787 |
| 2013/0309776 | A1 | 11/2013 | Drndic et al. |
| 2014/0026686 | A1 | 1/2014 | Bashir et al. |
| 2014/0054651 | A1 | 2/2014 | Bashir et al. |
| 2014/0139204 | A1 | 5/2014 | Bashir et al. |
| 2014/0363821 | A1 | 12/2014 | Bashir et al. |

OTHER PUBLICATIONS

Asmann et al. (2002) "Identification of Differentially Expressed Genes in Normal and Malignant Prostate by Electronic Profiling of Expressed Sequence Tags," Cancer Res. 62:3308-3314.

Astier et al. (2006) "Toward Single Molecule DNA Sequencing: Direct Identification of Ribonucleoside and Deoxyribonucleoside 5'-Monophosphates by Using an Engineered Protein Nanopore Equipped with a Molecular Adapter," J. Am. Chem. Soc. 128:1705-1710.

Bates et al. (2003) "Dynamics of DNA Molecules in a Membrane Channel Probed by Active Control Techniques," Biophys. J. 84:2366-2372.

Bauer et al. (1964) "Point Defect Studies in Gold by Electron Irradiation at Low Temperatures. I. Threshold Displacement Energy and Displacement Cross Section," Phys. Rev. 135:A521-A526.

Benner et al. (2007) "Sequence-specific detection of individual DNA polymerase complexes in real time using a nanopore," Nat. Nanotechnol. 2:718-724.

Borsenberger et al. (2009) "Chemically Labeled Nucleotides and Oligonucleotides Encode DNA for Sensing with Nanopores," J. Am. Chem. Soc. 131:7530-7531.

Botstein et al. (2003) "Discovering genotypes underlying human phenotypes: past successes for mendelian disease, future approaches for complex disease," Nat. Genet. 33(Suppl):228-37.

Branton et al. (2008) "The potential and challenges of nanopore sequencing," Nat. Biotechnol. 26:1146-1153.

Calin et al. (2006) "MicroRNA signatures in human cancers," Nat. Rev. Cancer. 6:857-866.

Chen et al. (2004) "Probing Single DNA Molecule Transport Using Fabricated Nanopores," Nano Lett. 4:2293-2298.

Chen et al. (2010) "DNA translocation through an array of kinked nanopores," Nat. Mater. 9:667-675.

Chung et al. (Mar. 31, 2011) "Stability of DNA-Tethered Lipid Membranes with Mobile Tethers," Langmuir. 27:5492-5497.

Clarke et al. (2009) "Continuous base identification for single-molecule nanopore DNA sequencing," Nat. Nanotechnol. 4:265-270.

Cockroft et al. (2008) "A Single-Molecule Nanopore Device Detects DNA Polymerase Activity with Single-Nucleotide Resolution," J. Am. Chem. Soc. 130:818-820.

Dan et al. (2009) "Intrinsic Response of Graphene Vapor Sensors," Nano Lett. 9:1472-1475.

Deamer (2010) "Nanopore analysis of nucleic acids bound to exonucleases and polymerases," Annu. Rev. Biophys. 39:79-90.

Deamer et al. (2002) "Characterization of Nucleic Acids by Nanopore Analysis," Acc. Chem. Res. 35:817-825.

Dekker (2007) "Solid-state nanopores," Nat. Nanotechnol. 2:209-215.

Derrington et al. (2010) "Nanopore DNA sequencing with MspA," Proc. Natl Acad. Sci. USA. 107:16060-16065.

Drmanac et al. (2010) "Human Genome Sequencing Using Unchained Base Reads on Self-Assembling DNA Nanoarrays," Science. 327:78-81.

Durkan et al. (2000) "Analysis of Failure Mechanisms in Electrically Stressed Gold Nanowires," Ultramicroscopy. 82:125-133.

Eid et al. (2009) "Real-Time DNA Sequencing from Single Polymerase Molecules," Science. 323:133-138.

Faller et al. (2004) "The Structure of a Mycobacterial Outer-Membrane Channel," Science. 303:1189-1192.

Feldman et al. (2010) "Discovery of recurrent t(6;7)(p25.3;q32.3) translocations in ALK-negative anaplastic large cell lymphomas by massively parallel genomic sequencing," Blood. 117:915-919.

Fischbein et al. (2008) "Electron Beam Nanosculpting of Suspended Graphene Sheets," Applied Physics Letters. 93:113107. pp. 1-3.

Fologea et al. (2005) "Slowing DNA Translocation in a Solid-State Nanopore," Nano Lett. 5:1734-1737.

Fu et al. (Jul. 18, 2011) "Graphene Transistors Are Insensitive to pH Changes in Solution," Nano Lett. 11:3597-3600.

Garaj et al. (2010) "Graphene as a sub-nanometer trans-electrode membrane," Nature. 467(7312):190-193.

Geim (2007) "The Rise of Graphene," Nat. Mater. 6:183-191.

Geim (2009) "Graphene: Status and Prospects," Science. 324:1530-1534.

George (2009) "Atomic Layer Deposition: An Overview," Chem. Rev. 110:111-131.

Girdhar et al. (Sep. 30, 2013) "Graphene quantum point contact transistor for DNA sensing," Proc. Natl. Acad. Sci. USA. 110:16748-16753.

Girit et al. (2009) "Graphene at the Edge: Stability and Dynamics," Science. 323:1705-1708.

Gracheva et al. (2006) "Simulation of the electric response of DNA translocation through a semiconductor nanopore-capacitor," Nanotechnology. 17:622-633.

Groves et al. (1997) "Micropatterning fluid lipid bilayers on solid supports," Science. 275:651-653.

Hall (1975) "Access resistance of a small circular pore," J. Gen. Physiol. 66:531-532.

Hall et al. (2010) "Hybrid pore formation by directed insertion of alpha-haemolysin into solid-state nanopores," Nat. Nanotechnol. 5:874-877.

Harrer et al. (May 20, 2011) "Electrochemical Protection of Thin Film Electrodes in Solid-State Nanopores," Nanotechnology. 22:275304.

Healy (2007) "Nanopore-based single-molecule DNA analysis," Nanomedicine. 2:459-481.

Healy et al. (2007) "Solid-state nanopore technologies for nanopore-based DNA analysis," Nanomedicine. 2:875-897.

Heng et al. (2005) "Beyond the gene chip," Bell Labs Tech. J. 10:5-22.

Hoogerheide et al. (2009) "Probing Surface Charge Fluctuations with Solid-State Nanopores," Phys. Rev. Lett. 102:256804.

Howorka et al. (2001) "Sequence-specific detection of individual DNA strands using engineered nanopores," Nat. Biotech. 19:636-639.

Huang et al. (2010) "Identifying single bases in a DNA oligomer with electron tunneling," Nat. Nanotechnol. 5:868-873.

(56) References Cited

OTHER PUBLICATIONS

International Search Report with Written Opinion corresponding to International Patent Application No. PCT/US2012/048248, dated Dec. 21, 2012.
Iqbal et al. (2007) "Solid-state nanopore channels with DNA selectivity," *Nat. Nanotechnol.* 2:243-248.
Ivanov et al. (2010) "DNA Tunneling Detector Embedded in a Nanopore," *Nano Lett.* 11:279-285.
Jiang et al. (Mar. 18, 2011) "Charge Regulation in Nanopore Ionic Field-Effect Transistors," *Phys. Rev. E.* 83:031203.
Jin et al. (Apr. 10, 2011) "Gated transport in nanofluidic devices," *Microfluid. Nanofluid.* 11:297-306.
Jing et al. (2010) "One-Way Traffic of a Viral Motor Channel for Double-Stranded DNA Translocation," *Nano Lett.* 10:3620-3627.
Karnik et al. (2005) "Electrostatic Control of Ions and Molecules in Nanofluidic Transistors," *Nano Lett.* 5:943-948.
Karnik et al. (2007) "Rectification of Ionic Current in a Nanofluidic Diode," *Nano Lett.* 7:547-551.
Kasianowicz et al. (1996) "Characterization of individual polynucleotide molecules using a membrane channel," *Proc. Natl Acad. Sci. USA.* 93:13770-13773.
Keyser (Jun. 29, 2011) "Controlling molecular transport through nanopores," *J. R. Soc. Interface.* 8:1369-1378.
Kim et al. (2002) "Dispersing Character-istics of Graphite Suspension by Surface Modification with ABDM," *Part. Sci. Technol.* 20:95-107.
Kim et al. (2006) "Rapid Fabrication of Uniformly Sized Nanopores and Nanopore Arrays for Parallel DNA Analysis," *Adv. Mater.* 18:3149-3153.
Kim et al. (2007) "Nanopore sensor for fast label-free detection of short double-stranded DNAs," *Biosensors Bioelectron.* 22:2926-2931.
Kim et al. (2009) "Realization of a High Mobility Dual-Gated Graphene Field-Effect Transistor with $Al_2O_3$ Dielectric," *Appl. Phys. Lett.* 94:062107.
Kim et al. (Jul. 26, 2011) "Stretchable, Transparent Graphene Interconnects for Arrays of Micro-scale Inorganic Light Emitting Diodes on Rubber Substrates," *Nano Lett.* 11:3881-3886.
Kimoto et al. (2001) "Spatially Resolved EELS Analysis of Multilayer Using EFTEM and STEM," *J. Electron Microsc.* 50:523-528.
Knoll et al. (2008) "Tethered bimolecular lipid membranes—A novel model membrane platform," *Electrochim. Acta.* 53:6680-6689.
Knopfmacher et al. (2010) "Nernst Limit in Dual-Gated Si-Nanowire FET Sensors," *Nano Lett.* 10:2268-2274.
Kowalczyk et al. (2009) "Detection of Local Protein Structures along DNA Using Solid-State Nanopores," *Nano Lett.* 10:324-328.
Kowalczyk et al. (Jun. 19, 2011) "Single-molecule transport across an individual biomimetic nuclear pore complex," *Nat. Nanotechnol.* 6:433-438.
Lagerqvist et al. (2006) "Fast DNA Sequencing via Transverse Electronic Transport," *Nano Lett.* 6:779-782.
Laird (2003) "The power and the promise of DNA methylation markers," *Nat. Rev. Cancer.* 3:253-266.
Langford et al. (Nov. 12, 2010) "Unsupported planar lipid membranes formed from mycolic acids of Mycobacterium tuberculosis," *J. Lipid Res.* 52:272-277.
Lee et al. (1997) "CG island methylation changes near the GSTP1 gene in prostatic carcinoma cells detected using the polymerase chain reaction: A new prostate cancer biomarker," *Cancer Epidem. Biomar.* 6:443-450.
Li et al. (2001) "Ion-beam sculpting at nanometre length scales," *Nature.* 412:166-169.
Li et al. (2003) "DNA molecules and configurations in a solid-state nanopore microscope," *Nat. Mater.* 2:611-615.
Li et al. (2009) "Large-Area Synthesis of High-Quality and Uniform Graphene Films on Copper Foils," *Science.* 324:1312-1314.
Liao et al. (2010) "High-Speed Graphene Transistors with a Self-Aligned Nanowire Gate," *Nature.* 467:305-308.
Liao et al. (Jun. 20, 2011) "Thermally Limited Current Carrying Ability of Graphene Nanoribbons," *Phys. Rev. Lett.* 106:256801.
Lieberman et al. (2010) "Processive Replication of Single DNA Molecules in a Nanopore Catalyzed by phi29 DNA Polymerase," *J. Am. Chem. Soc.* 132:17961-17972.
Life Technologies (2012) "What's new with Ion and Next Generation Sequencing," http://www.iontorrent.com. [Last Accessed Oct. 10, 2014].
Liu et al. (2010) "De-screening of Field Effect in Electrically Gated Nanopores," *Appl. Phys. Lett.* 97:143109.
Liu et al. (2010) "Translocation of Single-Stranded DNA Through Single-Walled Carbon Nanotubes," *Science.* 327:64-67.
Luan et al. (2010) "Base-By-Base Ratcheting of Single Stranded DNA through a Solid-State Nanopore," *Phys. Rev. Lett.* 104:238103.
Mager et al. (2008) "Nanopore-Spanning Lipid Bilayers for Controlled Chemical Release," *Adv. Mater.* 20:4423-4427.
Mardis (2008) "Next-Generation DNA Sequencing Methods," *Annu. Rev. Genom. Human Genet.* 9:387-402.
McNally et al. (2010) "Optical Recognition of Converted DNA Nucleotides for Single-Molecule DNA Sequencing Using Nanopore Arrays," *Nano Lett.* 10:2237-2244.
Meller et al. (2000) "Rapid nanopore discrimination between single polynucleotide molecules," *Proc. Natl Acad. Sci. USA.* 97:1079-1084.
Meller et al. (2002) "Single molecule measurements of DNA transport through a nanopore," *Electrophoresis.* 23:2583-2591.
Merchant et al. (2010) "DNA Translocation through Graphene Nanopores," *Nano Lett.* 10:2915-2921.
Metzker (2010) "Sequencing technologies—the next generation," *Nat. Rev. Genet.* 11:31-46.
Min et al. (Feb. 6, 2011) "Fast DNA sequencing with a graphene-based nanochannel device," *Nat. Nanotechnol.* 6:162-165.
Mirsaidov et al. (2009) "Nanoelectromechanics of Methylated DNA in a Synthetic Nanopore," *Biophys. J.* 96:L32-L34.
Mitchell et al. (2008) "Chemical Tags Facilitate the Sensing of Individual DNA Strands with Nanopores," *Angew. Chem. Int. Ed.* 47:5565-5568.
Nam et al. (2009) "Ionic Field Effect Transistors with Sub-10 nm Multiple Nanopores," *Nano Lett.* 9:2044-2048.
National Human Genome Research Institute (2008) "Advanced Sequencing Technology Awards 2008," http://www.genome.gov/27527584. [Last Accessed Oct. 10, 2014].
Nelson et al. (2010) "Detection of Nucleic Acids with Graphene Nanopores: Ab Initio Characterization of a Novel Sequencing Device," *Nano Lett.* 10:3237-3242.
Olasagasti et al. (2010) "Replication of individual DNA molecules under electronic control using a protein nanopore," *Nat. Nanotechnol.* 5:798-806.
Postma (2010) "Rapid Sequencing of Individual DNA Molecules in Graphene Nanogaps," *Nano Lett.* 10:420-425.
Prasongkit et al. (Apr. 15, 2011) "Transverse Conductance of DNA Nucleotides in a Graphene Nanogap from First Principles," *Nano Lett.* 11:1941-1945.
Rahman et al. (2009) "Network modelling and simulation tools," *Simulation Modelling Practice and Theory.* 17(6):1011-1031.
Rhee et al. (2006) "Nanopore sequencing technology: research trends and applications," *Trends Biotechnol.* 24:580-586.
Rincon-Restrepo et al. (Jan. 11, 2011) "Controlled Translocation of Individual DNA Molecules through Protein Nanopores with Engineered Molecular Brakes," *Nano Lett.* 11:746-750.
Rothberg et al. (Jul. 20, 2011) "An Integrated Semiconductor Device Enabling Non-Optical Genome Sequencing," *Nature.* 475:348-352.
Salehi-Khojin et al. (Dec. 29, 2011) "Polycrystalline Graphene Ribbons as Chemiresistors," *Adv. Mater.* 24:53-57.
Salisbury et al. (1984) "Nanometer scale electron beam lithography in inorganic materials," *Appl. Phys. Lett.* 45:1289-1291.
Schneider et al. (2010) "DNA Translocation through Graphene Nanopores," *Nano Lett.* 10:3163-3167.
Sigalov et al. (2007) "Detection of DNA Sequences Using an Alternating Electric Field in a Nanopore Capacitor," *Nano Lett.* 8:56-63.

(56) References Cited

OTHER PUBLICATIONS

Singer et al. (2010) "Nanopore Based Sequence Specific Detection of Duplex DNA for Genomic Profiling," *Nano Lett.* 10:738-742.
Siwy et al. (2009) "Engineered voltage-responsive nanopores," *Chem. Soc. Rev.* 39:1115-1132.
Smeets et al. (2006) "Salt Dependence of Ion Transport and DNA Translocation through Solid-State Nanopores," *Nano Lett.* 6:89-95.
Smeets et al. (2008) "Translocation of RecA-coated double-stranded DNA through solid-state nanopores," *Nano Lett.* 9:3089-3095.
Song et al. (May 23, 2011) "Atomic-Scale Electron-Beam Sculpting of Near-Defect-Free Graphene Nanostructures," *Nano Lett.* 11:2247-2250.
Spencer (2004) "NHGRI Seeks Next Generation of Sequencing Technologies: New Grants Support Development of Faster, Cheaper DNA Sequencing," http://www.genome.gov/12513210. [Last Accessed Oct. 9, 2014].
Stein et al. (2004) "Surface-Charge-Governed Ion Transport in Nanofluidic Channels," *Physical Review Letters.* 93:035901.
Stoddart et al. (2009) "Single-nucleotide discrimination in immobilized DNA oligonucleotides with a biological nanopore," *Proc. Natl. Acad. Sci. USA.* 106:7702-7707.
Storm et al. (2003) "Fabrication of solid-state nanopores with single nanometer precision," *Nat. Mater.* 2:537-540.
Storm et al. (2005) "Fast DNA Translocation through a Solid-State Nanopore," *Nano Lett.* 5:1193-1197.
Storm et al. (2005) "Translocation of double-strand DNA through a silicon oxide nanopore," *Phys. Rev. E.* 71:051903.
Strathdee et al. (2002) Aberrant DNA methylation in cancer: potential clinical interventions, *Expert Rev. Mol. Med.* 4:1-17.
Supplementary European Search Report and Written Opinion corresponding to European Patent Application No. 12818129, dated Feb. 17, 2014.
Tanaka et al. (2009) "Partial sequencing of a single DNA molecule with a scanning tunnelling microscope," *Nat. Nanotechnol.* 4:518-522.
Taniguchi et al. (2009) "Fabrication of the gating nanopore device," *Appl. Phys. Lett.* 95:123701-123703.
The International HapMap, Consortium. (2005) "A haplotype map of the human genome," *Nature.* 437:1299-1320.
Thomas et al. (2004) "Coding single-nucleotide polymorphisms associated with complex vs. Mendelian disease: Evolutionary evidence for differences in molecular effects," *Proc. Natl Acad. Sci. USA.* 101:15398-15403.
Tsutsui et al. (2010) "Identifying single nucleotides by tunnelling current," *Nat. Nanotechnol.* 5:286-290.
Valota "Electrochemical Behavior of Monolayer and Bilayer Graphene," *ACS Nano.* 5(11):8809-8815.
Venkatesan (Aug. 26, 2011) "Solid-State Nanopore Sensors for Nucleic Acid Analysis," Ph.D. Disseration. *University of Illinois at Urbana-Champaign.*
Venkatesan (2011) "Solid-State Nanopore Sensors for Nucleic Acid Analysis," Ch. 1. In; *Nanopores: Sensing and Fundamental Biological Interactions. Springer.* New York, New York. pp. 1-33.
Venkatesan et al. (2009) "Highly Sensitive, Mechanically Stable Nanopore Sensors for DNA Analysis," *Adv. Mater.* 21:2771-2776.
Venkatesan et al. (2010) "DNA Sensing Using Nanocrystalline Surface-Enhanced $Al_2O_3$ Nanopore Sensors," *Adv. Funct. Mater.* 20:1266-1275.
Venkatesan et al. (Apr. 13, 2011) "Lipid Bilayer Coated $Al_2O_3$ Nanopore Sensors: Towards a Hybrid Biological Solid-State Nanopore," *Biomed. Microdevices.* 13:671-682.
Venkatesan et al. (Sep. 18, 2011) "Nanopore Sensors for Nucleic Acid Analysis," *Nat. Nanotechnol.* 6:615-624.
Venkatesan et al. (Dec. 13, 2011) "Stacked Graphene-$Al_2O_3$ Nanopore Sensors for Sensitive Detection of DNA and DNA-Protein Complexes." *ACS Nano.* 6(1):441-450.
Vercoutere et al. (2001) "Rapid discrimination among individual DNA hairpin molecules at single-nucleotide resolution using an ion channel," *Nat. Biotech.* 19:248-252.
Volinia et al. (2006) "A microRNA expression signature of human solid tumors defines cancer gene targets," *Proc. Natl Acad. Sci. USA.* 103:2257-2261.
Wanunu et al. (2007) "Chemically Modified Solid-State Nanopores," *Nano Lett.* 7:1580-1585.
Wanunu et al. (2008) "DNA Translocation Governed by Interactions with Solid-State Nanopores," *Biophys. J.* 95:4716-4725.
Wanunu et al. (2010) "Discrimination of Methylcytosine from Hydroxymethylcytosine in DNA Molecules," *J. Am. Chem. Soc.* 133:486-492.
Wanunu et al. (2010) "Electrostatic focusing of unlabelled DNA into nanoscale pores using a salt gradient," *Nat. Nanotechnol.* 5:160-165.
Wanunu et al. (2010) "Rapid electronic detection of probe-specific microRNAs using thin nanopore sensors," *Nat. Nanotechnol.* 5:807-814.
Wendell et al. (2009) "Translocation of double-stranded DNA through membrane-adapted phi29 motor protein nanopores," *Nat. Nanotechnol.* 4:765-772.
White et al. (2006) "Ionic conductivity of the aqueous layer separating a lipid bilayer membrane and a glass support," *Langmuir.* 22:10777-10783.
Wood et al. (Sep. 23, 2011) "Effects of Polycrystalline Cu Substrate on Graphene Growth by Chemical Vapor Deposition," *Nano Lett.* 11:4547-4554.
Wu et al. (2005) "Formation of Nanopores in a SiN/SiO2 Membrane with an Electron Beam," *Appl. Phys. Lett.* 87:113106.
Wu et al. (2009) "Control of Shape and Material Composition of Solid-State Nanopores," *Nano Lett.* 9:479-484.
Yusko et al.(Feb. 20, 2011) "Controlling protein translocation through nanopores with bio-inspired fluid walls," *Nat. Nanotechnol.* 6:253-260.
Zhao et al. (2007) "Detecting SNPs Using a Synthetic Nanopore," *Nano Lett.* 7:1680-1685.
Zhijun et al. (2010) "Fabrication of Nanopores with Embedded Annular Electrodes and Trans-verse Carbon Nanotube Electrodes," *J. Phys.: Condens. Matter.* 22:454114.
Zhi-mei et al. (2009) "Slow Spontaneous Transformation of the Morphology of Ultrathin Gold Films Characterized by Localized Surface Plasmon Resonance Spectroscopy," *Nanotechnology.* 20:255702.
Zhou et al. (2010) "The next-generation sequencing technology: A technology review and future perspective," *Scientia Sinica.* 53(1):44-57.
Zwolak et al. (2008) "Colloquium: Physical approaches to DNA sequencing and detection," *Rev. Mod. Phys.* 80:141-165.
Notice of Reasons for Rejection corresponding to Japanese Patent Application P2014-522982, dispatched Jun. 7, 2016—English translation only.
Office Action corresponding to European Patent Application No. 12818129.4, dated Feb. 12, 2016.
Office Action corresponding to Chinese Patent Application No. 2012800468665, dated Apr. 26, 2016. (English translation).
Michael D. Fischbein and Marija Drndic, Electron Beam Nanosculpting of Suspended Graphene Sheets, 3 pages, Sep. 16, 2008, Applied Physics Letters.†

\* cited by examiner
† cited by third party

NANOPORE SENSORS FOR BIOMOLECULAR CHARACTERIZATION

CROSS-REFERENCE TO RELATED APPLICATIONS

This application is a national stage application under 35 U.S.C. § 371 of PCT/US2012/048248, filed Jul. 26, 2012, which claims the benefit of priority of U.S. Provisional Patent Application No. 61/512,095 filed Jul. 27, 2011, which are hereby incorporated by reference in their entirety to the extent not inconsistent herewith.

STATEMENT REGARDING FEDERALLY SPONSORED RESEARCH OR DEVELOPMENT

This invention was made with government support under contract numbers NIH 5R21CA155863-02 and NIH R25CA154015 awarded by the National Institute of Health. The government has certain rights in the invention.

BACKGROUND

Provided are methods and devices for characterizing a biomolecule by monitoring an electrical parameter as the biomolecule transits a nanopore, including under an applied electric field. A number of conventional techniques are available for sequencing biomolecules including, as discussed in U.S. Pat. Pub. No. 2011/0226623, Sanger sequencing, sequencing by synthesis, pyrosequencing, sequencing by hybridization, massively parallel signature sequencing and non-enzymatic real-time single-molecule sequencing. U.S. Pat. Pub. No. 2012/0040343 discusses techniques for characterizing methylation levels including methods involving immunoprecipitation, digestion by methyl-sensitive enzymes, methylation sensitive PCR and DNA methylation binding columns. U.S. Pat. No. 5,795,782 discusses characterization of polymer molecules based on monomer-interface interactions.

There is a need in the art for systems and methods capable of precise control over the electrical properties in and around the nanopore to better control biomolecule transit and/or electrical parameter measurement in and around the nanopore, particularly during biomolecule transit or interaction with the nanopore. The methods and devices disclosed herein are configured to characterize a wide range of biomolecules, including different aspects of the biomolecule as desired, that are not readily achieved by conventional systems known in the art.

SUMMARY

Provided herein are methods and devices for characterizing a biomolecule parameter by a nanopore-containing membrane, and also methods for making devices that can be used in the methods and devices provided herein. Specially configured membranes containing a plurality of layers in a stack configuration, such as conductor/dielectric layers including graphene/dielectric layers with a nanopore through the layers, to facilitate improved control of biomolecule transit through the nanopore as well as measuring or monitoring of an electrical parameter generated during biomolecule transit through the nanopore. In particular, a conducting layer or a graphene layer provided as an embedded electrode gate that is independently biased from the rest of the device provides the ability to uniquely control biomolecule transit and/or electrical parameter measurement during biomolecule transit.

In an aspect, provided herein are devices, and use of those devices, having more than two electrical terminals, such as a pair of electrical terminals to provide a potential difference across the nanopore membrane and another terminal to energize an electrode integrated in the membrane, such as a graphene electrode or other atomically thin conducting layer such as doped silicon, monolayer silicon or silicene, ultra-thin metal, $MoS_2$ electrode. In an embodiment, the electrode is graphene or $MoS_2$. In an embodiment, a plurality of electrodes are energized. The integrated electrode is referred to as a "gate" electrode and can be independently biased to control translocation velocity of a biomolecule through the nanopore and to achieve either p-type or n-type behavior for embodiments comprising microribbons or nanoribbons for electrically characterizing the transiting biomolecule. The gate electrode is electrically isolated from other components of the system to provide independent control of the electric field in and/or adjacent to the nanopore. In an aspect, the gate electrode is tied to the source electrode. In an aspect, any number of independently biased gate electrodes can be incorporated, such as by a plurality of graphene layers shaped and electrically connected to a voltage source. The graphene layers embedded in the device to provide gate electrodes may be shaped into microribbons, nanoribbons and nanogaps. "Nano" refers to a dimension that is less than about 1 µm and greater than about 0.1 nm. "Micro" refers to a dimension that is less than about 1 mm and greater than about 1 µm.

In an aspect, the nanoribbon functions as a nucleotide reader with each nucleotide uniquely modulating the transverse current or conductance. Functionalization of nanoribbon edges with materials that interact with specific nucleotides can further enhance nucleotide-specific interactions, including exonuclease, polymerase, proteins, helicase or chemical moieties that specifically bind individual nucleotide or amino acid types or short specified sequences of polynucleotides or amino acids.

Any of the devices or methods provided herein optionally provide for the detection of a single unit of a multi-unit biomolecule (e.g., organic or synthetic nucleotides, amino acids) within a long biomolecule by electronic means. The electrodes, including electrodes embedded in the device, can sense or measure an electrical parameter, and also allow for field effect gating of the nanopore for slowing down or trapping a biomolecule.

One important aspect provided herein is a third nanoscale terminal made of graphene at the pore sandwiched between insulating layers, such as dielectric layers. Such a sandwiched conducting layer or terminal is also referred to as a "buried" layer, such as buried graphene. The buried graphene layer may be used as a sheet to measure current through biomolecules in or transiting the nanopore, or fashioned into a ribbon with a nanopore to measure transverse conductance or impedance as biomolecules pass through the pore, or to measure the tunneling current across two graphene electrodes. Another planar graphene electrode can be used to gate the pore and adjust the translocation velocity, such as slowing the biomolecule transit speed, thereby increasing signal to noise ratio.

Optionally, three or more graphene electrodes can be utilized in a Wheatstone Bridge architecture, for example, for sensitive detection of DNA and DNA/protein complexes. Horizontal Wheatstone Bridge structures are contemplated, where the species of interest passes adjacent to the electrodes, which are placed within a nanochannel. Vertical Wheatstone Bridge structures are also contemplated, where the electrodes include a nanopore aligned along a nanochannel and the species of interest passes through the nanopore. Accordingly, an embodiment of the invention relates to connecting the conducting layers, such as graphene layers, in a Wheatstone Bridge configuration for measuring an electrical parameter in or around the nanopore, wherein the electrical parameter is one or more of: differential impedance, tunneling current, resistance, capacitance, current or voltage.

In an embodiment, the device and methods relate to any one of DNA sequencing, RNA sequencing, sequencing of other polynucleotides such as LNA, PNA, or XNA, protein or amino acid sequencing, haplotyping, methylation detection and/or mapping, and related applications.

In an embodiment, provided are methods for characterizing a biomolecule parameter, such as by providing a nanopore in a membrane comprising a conductor-dielectric stack. The membrane separates a first fluid compartment from a second fluid compartment and the nanopore fluidly connects the first and said second fluid compartments. "Fluidly connects" refers to a fluid capable of moving between the compartments via the nanopore, and constituents within the fluid that are smaller than the nanopore capable of moving likewise. The biomolecule is applied to the first fluid compartment and an electric field applied across the membrane. In this manner, the biomolecule is forced or driven through the nanopore in a direction from the first to the second fluid compartment under the applied electric field, including for biomolecules that have a charge. An electrical parameter is monitored across the membrane as the biomolecule transits the nanopore, thereby characterizing the biomolecule parameter. Alternatively, the electrical parameter is monitored across the nanopore or through the nanopore. In an aspect, the conducting layer is one or more of an atomically thin conducting layer. In an aspect, atomically thin refers to a layer thickness that is on the order of a few atoms or less. In an aspect, atomically thin refers to a layer thickness that is less than about 1 nm thick, or less than about 0.5 nm thick.

The multilayer stack geometry provides a number of functional benefits, including the ability to activate and measure electric fields independently and in various directions in and around the pore. For example, outermost graphene layers may be energized to slow down the passage or ratchet a biomolecule that may normally transit the nanopore too quickly, with a central graphene layer, including a nanoribbon, used to characterize a biomolecule parameter based on changes in an electrical parameter such as conductance, impedance, resistance, current, and/or potential. Similarly, the multilayer stack geometry may be configured to provide a gate electrode, including for field effect gating and/or field effect sensing such as by an embedded electrode corresponding to either of the central or outermost graphene layers corresponding to the top layer or bottom layer. Any of the multilayer stacks are optionally covered with an insulating layer, including a patterned layer so that desired electrode regions are directly exposed to fluid in which the biomolecule is suspended.

In an aspect, the biomolecule parameter is selected from the group consisting of: polynucleotide sequence; presence of modified nucleotides including a tagged nucleotide, polynucleotide methylation or hydroxymethylation state, methyl or hydroxymethyl-dependent binding protein bound to a one or more methylated or hydroxymethylated sites on a polynucleotide sequence; presence of a protein-polynucleotide binding event; polypeptide sequence; biomolecule secondary structure; and amino acid sequence. The methods and devices provided herein are compatible with a range of biomolecule parameters, so long as the biomolecule parameter being characterized affects the electrical parameter being measured. The use of conducting layers such as graphene layers within a multilayer stack provides access to accurate and focused electric field manipulation and control, including by one or more gate electrodes.

Methods and devices provided herein are compatible with a range of biomolecules that are polymeric in nature with unit repeat structures, such as organic or synthetic nucleic acids, including polynucleotides, poly-amino acids, proteins, biopolymers and mixtures thereof. In an aspect, the polynucleotide is a polynucleotide that comprises DNA, RNA, PNA, LNA or XNA. In an embodiment, the DNA is single stranded. In an embodiment, the DNA is double stranded.

Any of the methods and devices provided herein relate to a graphene-dielectric stack comprising a plurality of graphene layers, wherein adjacent graphene layers are separated by a dielectric layer. In an aspect, the number of graphene layers are 2, 3, 4, 5 or 6. In an aspect, the number of graphene layers are at least 3, with a middle graphene layer corresponding to one or more micro or nanoribbons in electrical isolation for control and/or characterization of electric field in the nanopassage formed by the nanopore and outer graphene layers independently providing controlled gating.

In an embodiment, one of the graphene layers comprise a graphene microribbon, nanoribbon or nanogap through which the nanopore traverses in a direction that is transverse to a longitudinal direction of the graphene nanoribbon. In an aspect of this embodiment, the method further comprises measuring a time-course of electric potential or transverse current along the graphene microribbon, nanoribbon or nanogap during biomolecule transit through the nanopore, thereby characterizing a sequence or a length of the biomolecule. A plurality of microribbons or nanoribbons may be used to simultaneously measure different parameters or the same parameter at different biomolecule positions or orientations, thereby allowing multiple simultaneous reads of the translocating biomolecule. In an embodiment, vertically adjacent ribbons have longitudinal directions that are offset with respect to each other, such as by an offset angle that is greater than 20°, or selected from a range that is between about 10° and 180°, between about 30° and 130°, or about 90°. In this manner, the influence of adjacent electrically energized nanoribbons is minimized. In an aspect, the multiple longitudinal directions of micro or nanoribbons are arranged in a parallel configuration. In an aspect, a portion of the nanoribbons or microribbons are aligned parallel with respect with to each other and another portion has a different longitudinal orientation.

The multilayer aspect of the membrane, including embodiments having multiple graphene layers, facilitates a configuration for independently electrically biasing at least one of the graphene layers to provide electrical gating of the nanopore, including with respect to the biomolecule. In an aspect, the biasing is by electrically connecting an electrode embedded in the graphene-dielectric stack to an individual graphene layer, and the biasing modifies an electric field in the nanopore generated by the applied electric field across the membrane.

The methods and devices provided herein are compatible with a range of dielectric materials. In an aspect, any of the methods and devices related to a dielectric layer comprising Aluminum Oxide, Tantalum Oxide, Titanium Oxide, Silicon Dioxide, Hafnium Oxide, Zirconium Oxide, Boron Nitride, Silicon Nitride, nanolaminates thereof, or any combination thereof.

The particular electrical parameter of interest depends on the context in which the method or device is employed as well as the device configuration. Examples of relevant electrical parameters include: current or current blockade through the nanopore; tunneling current across the nanopore; conductance; electrochemical current through a transverse electrode; resistance; impedance; electric potential; and translocation time or transit speed of the biomolecule through said nanopore. The ability to precisely define embedded electrodes in the multilayer and with respect to the nanopore, facilitates electrical parameter measurements across (e.g., orthogonal to) or along the axial direction of the nanopore.

Any of the methods and devices provided herein optionally further comprise functionalizing exposed edges of graphene in the nanopore by attaching a chemical moiety to an exposed nanopore graphene edge. The chemical moiety has an affinity to a portion of the biomolecule, including a binding affinity that may periodically slow transit speed, and the chemical moiety interacting with the portion of the biomolecule changes the monitored electrical parameter as the biomolecule transits the nanopore. Examples of a chemical moiety include recognition molecules for a specific nucleotide, amino acid and/or sequence of nucleotides or amino acids of the biomolecule, including polynucleotides, polypeptides, polyamino acids, antibodies, receptors and artificially constructed chemicals and chemical groups having high affinity for a target molecule.

In an aspect, the chemical moiety is selected from the group consisting of: synthetic molecules, proteins and polynucleotides having a sequence that binds to a sequence within the biomolecule of interest; and a chemical construct having a binding affinity to a specific nucleotide within the biomolecule that is a polynucleotide, such as A, G, C or T nucleotide binding proteins or chemical constructs. Optionally, to further enhance binding affinity between the chemical moiety and the specific nucleotide the specific nucleotide in the biomolecule to which the chemical moiety binds is labeled with heavy atoms, chemical functional groups, or tags that enhance affinity with the chemical moiety.

In an embodiment, the method further comprises the step of digesting a biomolecule having a polynucleotide sequence into a plurality of smaller sequences by contacting the biomolecule with an exonuclease that is anchored to the graphene-dielectric stack, thereby providing sequencing by digestion. In an aspect, at least a portion of the plurality of smaller sequences corresponds to individual bases or nucleotides of the polynucleotide sequence.

In an embodiment, the method further comprises the step of synthesizing a polynucleotide sequence by adding nucleotides to the biomolecule that is transiting the nanopore, thereby providing sequencing by synthesis. In an aspect, the sequencing by synthesis is by a polymerase anchored to the graphene-dielectric stack and the added nucleotides are from a source of nucleotides in the first fluid compartment. Optionally, the sequencing by synthesis further comprises the step of detecting released $H^+$ or pyrophosphates during addition of a nucleotide to the biomolecule transiting the pore, such as by measuring a change in nanopore current. In this manner, the electrical parameter that is monitored reflects the nucleotide type that is added to the biomolecule. In another embodiment, a helicase is anchored to the graphene-dielectric stack to unwind DNA and pass single-stranded DNA through the pore, facilitating strand sequencing.

Any of the methods and devices provided herein relate to a nanopore that is a biological nanopore. A biological nanopore refers to a nanopore that further comprises a protein construct that contains an aperture that is the nanopore. The protein is selected depending on the biomolecule and biomolecule parameter being characterized. In an embodiment, the protein is a polymerase, nuclease, histone, helicase, transcription factor, alpha hemolysin or *Mycobacterium smegmatis* porin A or GP10. In an embodiment, the protein is selected based on the target biomolecule that is being detected, such as a protein nanopore having high binding affinity to the target biomolecule, including a specific portion of the biomolecule referred herein as the binding region of the biomolecule to the protein.

In an aspect, any of the methods and devices provided herein may be characterized in terms of the layout and positioning of layers, such as a top-most graphene layer that is in fluid and electrical contact with the first fluid compartment. In an embodiment of this aspect, the electrical parameter is from a resistive measurement by the graphene layer in fluid and electrical contact with fluid in the first fluid compartment.

In an embodiment, any of the methods provided herein measure the electrical parameter by field effect gating or field effect sensing by a graphene layer electrically insulated from the fluid in the fluid compartment and in the nanopore. In this embodiment, the graphene layer may be an interior layer of the stack and may be shaped to apply local AC or DC potentials in the port to provide precise gating or sensing, such as by one or more nanoribbons.

Any of the methods provided herein may relate to a biomolecule that is a double stranded polynucleotide sequence, wherein the method further comprises the step of unzipping the double stranded polynucleotide sequence and driving a single strand of the double stranded polynucleotide sequence through the nanopore, thereby providing sequencing of said biomolecule. In an aspect, the unzipping is by a helicase anchored to the multilayer stack, such as a graphene-dielectric stack.

In an aspect, a plurality of conducting layers are provided, such as three or four layers, with a buried graphene layer that measures the electrochemical current through another graphene layer.

In another embodiment, the invention is a device, including a device for implementing any of the methods provided herein, such as for characterizing a biomolecule parameter. In an aspect, the device comprises a membrane. The membrane has a first surface and a second surface opposite the first surface, wherein the membrane separates a first fluid compartment from a second fluid compartment. In an aspect, the membrane first and second surfaces form a surface of the first fluid compartment and the second fluid compartment, respectively. In an aspect, the membrane comprises a graphene/dielectric/graphene/dielectric stack, such as a graphene/$Al_2O_3$/graphene/$Al_2O_3$ stack, positioned between the membrane first surface and the second surface with a nanopore through the membrane that fluidically connects the first compartment and the second compartment. In an aspect, the outermost layers of the graphene/dielectric multilayer stack form the first and second surface. Alternatively, one or both of the outermost layers of the graphene/dielectric multilayer stack are coated with a coating layer that at least partially separates the outermost layers of the graphene/dielectric multilayer stack from the fluid compartments. In an aspect, the outermost graphene layer is at least partially coated with an electrically insulating layer or dielectric layer, including a dielectric or an $Al_2O_3$ coating layer. The device may further comprise components to provide controlled and focused electric field and corresponding detection of an electrical parameter used to characterize a biomolecule parameter of a biomolecule that transits or interacts with the nanopore. Examples of such components include a power or voltage supply to provide an electric potential difference between the first fluid compartment and the second fluid compartment, a detector to detect an electrical parameter associated with the biomolecule transit through the nanopore, including an electrical current through the nanopore, an electrochemical current through a graphene layer or across a transverse electrode, as a biomolecule transits the nanopore under an applied electric potential difference between the first and second fluid compartments, and electrodes such as gate, sensing, source and drain electrodes.

In an aspect, the device further comprises one or more gate electrodes, wherein each of the one or more gate electrodes is a graphene layer in the multilayer stack. In an aspect, the gate electrode is independently electrically connected to one or more of the graphene layers in the stack. In an aspect, the gate electrode is formed from at least a portion of the graphene layer, such as an electrode that is a nanoribbon or having a tip end geometry to focus electric field generation and/or electrical parameter detection.

In an aspect, any of the conducting, graphene or dielectric layers are described in terms of thickness. In an embodiment, the conducting or graphene layer has a thickness that is less than or equal to 3 nm at the nanopore. In an embodiment, the electrical contact comprises a metal pad, such as a Ti/Au pad, in electrical contact with the conducing or graphene layer and an electrically conductive wire in electrical contact with the metal pad, wherein the metal pad is electrically isolated from any of the first and second fluid compartment.

In an embodiment, the gate electrode is electrically connected to a source electrode powered by the power supply.

Any of the graphene layers provided herein may comprise a nanoribbon through which the nanopore transits in a transverse direction to the nanoribbon longitudinal axis. The nanoribbon optionally comprises electrical contacts for measuring a transverse current along the nanoribbon during transit of a biomolecule through the nanopore and another of the graphene layers is connected to a gate electrode to electrically bias the graphene layer. In an embodiment, any of the nanopores provided herein have a diameter that is greater than 5% of the nanoribbon width or is selected from a range between 5% and 95% of the nanoribbon width. In this manner, the nanoribbon may circumferentially surround the nanopore by a circumferential region that is relatively narrow or relatively wide dependent on the application of interest. The gate electrode electrically connected to the nanoribbon then provides the ability to independently electrically bias the nanoribbon to provide additional control to the system.

In an aspect, the detector is a tunneling detector comprising a pair of electrodes facing each other and centered within the nanopore in a direction transverse to the biomolecule transit direction in the nanopore, wherein the biomolecule transits between the pair of electrodes.

In an alternative embodiment, provided herein is a method of making a membrane comprising nanopores for characterizing a biomolecule parameter. In an aspect, the method comprises the steps of: forming a passage in a free-standing dielectric membrane, including an $Al_2O_3$ membrane; growing a graphene layer via chemical vapor deposition; coating or transferring to the free-standing dielectric membrane at least a portion of the graphene layer; forming a dielectric layer on the graphene layer; repeating the graphene layer step to generate a second graphene layer; repeating the dielectric depositing step to generate a second dielectric layer; forming a nanopore extending from a first surface of the membrane to a second surface of the membrane, wherein the nanopore traverses each of the graphene and dielectric layers, thereby making a membrane comprising a nanopore in a graphene/dielectric/graphene/dielectric stack. The forming dielectric layer and repeating step thereof on the transferred graphene layer may be with or without a metal seed layer.

In aspect, the method further comprises electrically contacting the first graphene layer, the second graphene layer or both the first graphene layer and the second graphene layer with an electrical contact to provide an independent electrically gated nanopore.

In an embodiment, the repeating step is repeated to generate three or more graphene layers, with adjacent graphene layers separated by dielectric layers. In this manner the stack may comprise any number of graphene layers, including stacks where none, one, or both the top-most and bottom-most layers comprise graphene layers. In an aspect, any one or more of the graphene layers are electrically contacted to provide an independent electrically gated nanopore.

In an aspect, any of the methods further comprises embedding a gate electrode in the nanopore membrane to modify a localized electric field in and adjacent to the nanopore. In this manner, any of the devices provided herein have an embedded gate electrode configured to modify a localized electric field in and adjacent to the nanopore. In an aspect, the embedded gate electrode comprises any of the graphene layers of the membrane.

In an aspect, the dielectric layer comprises a dielectric deposited by atomic layer deposition. In an aspect, the dielectric layer comprises $Al_2O_3$, $Ta_2O_5$, $SiO_2$, $Si_3N_4$, aluminum oxide, tantalum oxide, hafnium oxide, zirconium oxide, silicon dioxide, or silicon nitride or a combination of thereof.

In an embodiment, any of the methods and devices provided herein has an electrical circuit layout in a Wheatstone Bridge configuration. Accordingly, any of the methods may further comprise electrically connecting three or more graphene layers in Wheatstone Bridge configuration for measuring an electrical parameter in the nanopore. Such a Wheatstone Bridge provides the ability to measure an unknown electrical parameter by balancing different legs of the bridge circuit. In an aspect, the electrical parameter is one or more of: differential impedance, tunneling current, resistance, capacitance, current or voltage.

In an aspect, the method further comprises electrically biasing a central graphene layer of the three or more graphene layers with an AC bias relative to two outer graphene layers of the three or more graphene layers. In this manner, the method may further comprise monitoring impedances between the central graphene layer and the outer graphene layers. In an embodiment, the method further comprises biasing one or more graphene layers with an AC voltage signal.

Another embodiment of the invention relates to a method for identifying, characterizing or quantifying the methylation or hydromethylation status of a biomolecule by providing a nanopore in a suspended membrane that separates a first fluid compartment from a second fluid compartment. The membrane may comprise Aluminum Oxide, Tantalum Oxide, Titanium Oxide, Silicon Dioxide, Hafnium Oxide, Zirconium Oxide, Boron Nitride, Silicon Nitride, graphene or nanolaminates thereof, or any combination thereof. In an aspect, the membrane is a multilayer stack comprising an electrically conducting layer and dielectric layer, including a plurality of electrically conducting layers such as graphene separated by dielectric layers, or any of the stacks provided herein. Specific proteins, oligonucleotides or chemical tags are bound to methylated or hydroxymethylated site on target biomolecule. An electric field is applied across the membrane, from the first fluid compartment to the second fluid compartment, to drive the biomolecule through the nanopore. The bound protein or tags on said biomolecule are detected by monitoring changes in ionic current, tunneling current, voltage, conductance or impedance during biomolecule transit through the nanopore.

In an aspect, the method further comprises the step of sequentially shearing bound protein or tags from the biomolecule as the biomolecule transits through the nanopore.

In an embodiment, the devices and methods provided herein relate to a nanoscale pH sensor for use in detecting generation of pyrophosphates and changes in pH due to biochemical reactions at either the single molecule level or from a collection or aggregate of molecules.

Without wishing to be bound by any particular theory, there can be discussion herein of beliefs or understandings of underlying principles or mechanisms relating to embodiments of the invention. It is recognized that regardless of the ultimate correctness of any explanation or hypothesis, an embodiment of the invention can nonetheless be operative and useful.

DETAILED DESCRIPTION

Figure 1:
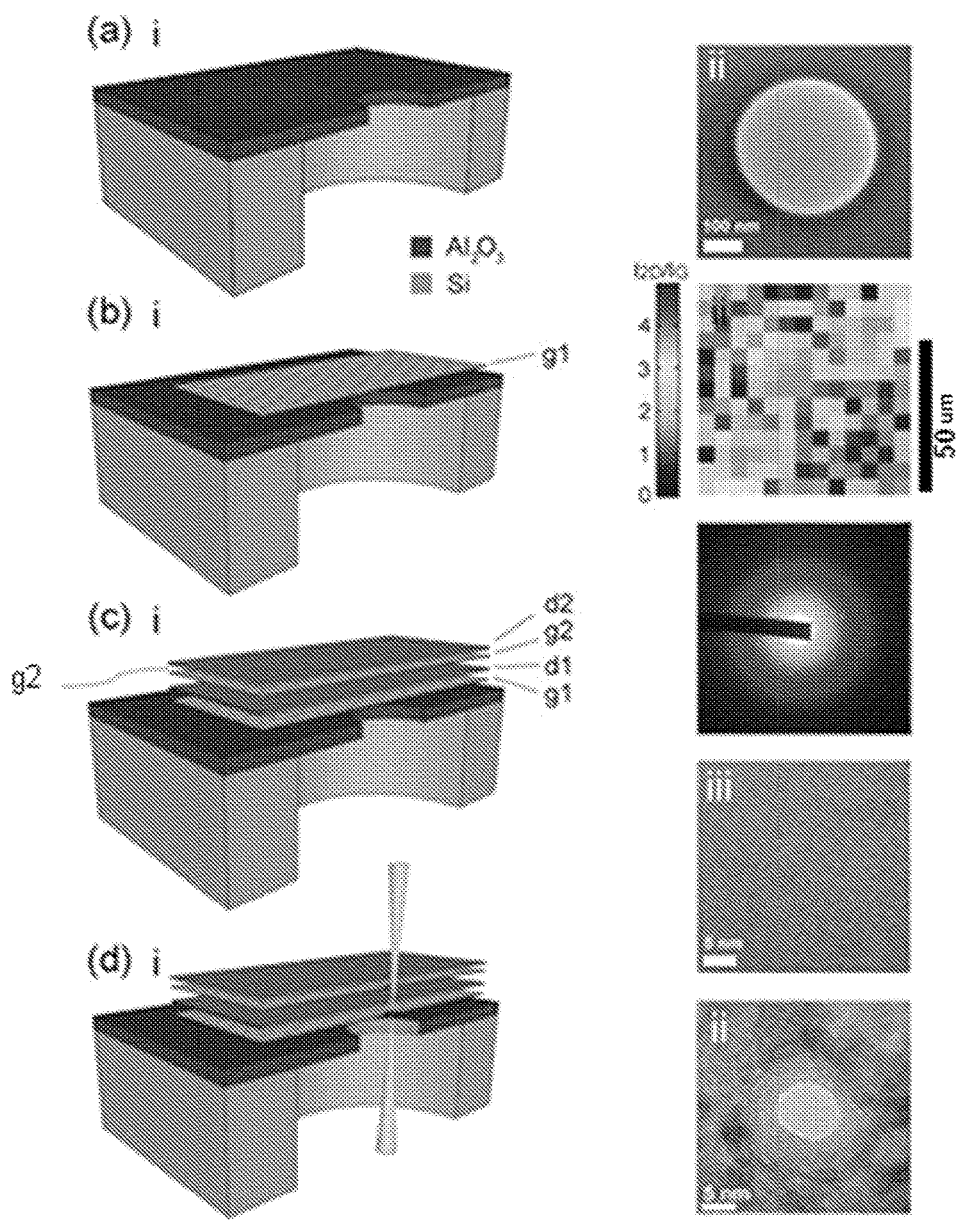
FIG. 1. Fabrication of graphene-$Al_2O_3$ nanopores: (a) A 300 nm diameter pore is first formed using a focused ion beam (FIB) tool in a free standing $Al_2O_3$ membrane (b) Transfer CVD grown graphene onto chip (c) Evaporate 1.5 nm Al as a seed layer and then deposit 6.5 nm of ALD $Al_2O_3$ (d1) on the chip. Transfer another graphene layer that extends to the edge of the chip for contacting g2 using gold pads, and repeat Al/$Al_2O_3$ deposition (d2). (d) FEGTEM nanopore formation.

"Biomolecule" is used broadly herein to refer to a molecule that is relevant in biological systems. The term includes, for example, polynucleotides, DNA, RNA, polypeptides, proteins, and combinations thereof. The biomolecule may be naturally occurring or may be engineered or synthetic. A "biomolecule parameter" refers to a measurable or quantifiable property of the biomolecule. The parameter may be a constant for the biomolecule, such as the sequence or a sequence portion. The parameter may vary for a particular biomolecule depending on the state or conditions of the biomolecule, such as for a biomolecule parameter that is a methylation state, binding event and/or secondary structure. An "electrical parameter" refers to a parameter that can be electrically measured or determined and that relates to the biomolecule parameter. Accordingly, electrical parameter may be electrical in nature, or may itself by a non-electrical parameter that is determined based on an underlying parameter that is electrical in nature, such as transit or translocation time, flux, or translocation frequency.

"Methylation" refers to DNA having one or more residues that are methylated. For example, in all vertebrate genomes some of the cytosine residues are methylated. DNA methylation can affect gene expression and, for some genes, is an epigenetic marker for cancer. Two different aspects of DNA methylation can be important: methylation level or content as well as the pattern of methylation. "Methylation state" is used broadly herein to refer to any aspect of methylation that is of interest from the standpoint of epigenetics, disease state, or DNA status and includes methylation content, distribution, pattern, density, and spatial variations thereof along the DNA sequence. Methylation detection via nanopores is further discussed in U.S. Pub. No. 2012/0040343 (168-08).

In addition, biomolecule parameter refers to a quantitative variable that is measurable and is affected by the biomolecule transit through a nanopore, such as for example, translocation speed through a nanopore, variations in an electrical parameter (e.g., changes in the electric field, ionic current, resistance, impedance, capacitance, voltage) in the nanopore as the biomolecule enters and transits the pore, changes arising from biochemical reaction between the biomolecule and a nanopore surface region functionalized with a chemical moiety such as the release of pyrophosphates, changes in pH including via a chemical moiety having exonuclease or endonuclease function.

"Dielectric" refers to a non-conducting or insulating material. In an embodiment, an inorganic dielectric comprises a dielectric material substantially free of carbon. Specific examples of inorganic dielectric materials include, but are not limited to, silicon nitride, silicon dioxide, boron nitride, and oxides of aluminum, titanium, tantalum or hafnium. A "high-k dielectric" refers to a specific class of dielectric materials, for example in one embodiment those dielectric materials having a dielectric constant larger than silicon dioxide. In some embodiments, a high-k dielectric has a dielectric constant at least 2 times that of silicon dioxide. Useful high-k dielectrics include, but are not limited to $Al_2O_3$, $HfO_2$, $ZrO_2$, $HfSiO_4$, $ZrSiO_4$ and any combination of these. In an aspect, any of the methods and devices provided herein have a dielectric that is $Al_2O_3$.

"Conductor-dielectric stack" refers to a plurality of layers, with at least one layer comprising an electrical conductor and another layer a dielectric. In an embodiment, a layer may be geometrically patterned or deposited, such as in a nanoribbon configuration including a conductor layer that is a conducting nanoribbon having a longitudinal direction that is transverse to the passage formed by the nanopore. In an aspect, the stack comprises 2 or more layers, 3 or more layers, or a range that is greater than or equal to 5 layers and less than or equal to 20 layers. In an aspect, adjacent conductor layers are separated from each other by a dielectric layer. In an aspect the outermost layers are conducting layers, dielectric layers, or one outermost layer that is dielectric and the other outermost layer at the other end of the stack is a conductor. In an aspect, local electric field may be applied and controlled near the membrane surface by selectively patterning a dielectric layer that covers an underlying conductor layer that is electrically energized. Any of the methods and devices provided herein have a conducting layer that is grapheme. As exemplified herein, the term graphene can be replaced, as desired, with other atomically thin electrically conducting layers, such as $MoS_2$, doped silicon, silicene, or ultra-thin metal.

"Fluid communication" or "fluidly connects" refers to a nanopassage that permits flow of electrolyte, and specifically ions in the electrolyte from one side of the membrane (e.g., first fluid compartment) to the other side of the membrane (e.g., second fluid compartment), or vice versa. In an aspect, the fluid communication connection is insufficient to permit biomolecule transit between sides without an applied electric field to facilitate transit through the nanopore. This can be controlled by combination of nanopore geometry (e.g., diameter), nanopore surface functionalization, applied electric field through the nanopore and biomolecule and fluid selection.

"Specific binding" refers to an interaction between two components wherein one component has a targeted characteristic. Binding only occurs if the one component has the targeted characteristic and substantially no binding occurs in the absence of the targeted characteristic. In an embodiment, the targeted characteristic is a nucleotide type (e.g., A, T, G, C), an amino acid, or a specific sequence of nucleotides.

The invention may be further understood by the following non-limiting examples. All references cited herein are hereby incorporated by reference to the extent not inconsistent with the disclosure herewith. Although the description herein contains many specificities, these should not be construed as limiting the scope of the invention but as merely providing illustrations of some of the presently preferred embodiments of the invention. For example, thus the scope of the invention should be determined by the appended claims and their equivalents, rather than by the examples given. PCT Pub. No. WO 2010/080617 (Atty ref. 168-08WO), U.S. Pat. Pub. No. 2012/0040343 and U.S. Pat. Pub. No. 2011/0226623 (Atty ref. 56-09, filed Dec. 17, 2010) are specifically incorporated by reference to the extent not inconsistent herewith for the systems, devices and methods provided therein as related to biomolecule characterization by transit of the biomolecule through a nanopore under an applied electric field.

EXAMPLE 1

Graphene-$Al_2O_3$ Nanopores

Graphene, an atomically thin sheet of carbon atoms densely packed into a two-dimensional honeycomb lattice possesses remarkable mechanical, electrical and thermal properties. The comparable thickness of a graphene monolayer to the 0.32-0.52 nm spacing between nucleotides in ssDNA, makes this material particularly attractive for electronic DNA sequencing. This example describes the development and characterization of novel graphene based $Al_2O_3$ nanopore sensors for the analysis of DNA and DNA-protein complexes. The nanopore is fabricated in a graphene-dielectric-graphene-dielectric stack, facilitating the independent biasing of each graphene layer. This structure is mechanically robust, exhibits stable conductance in ionic solution, is pH sensitive and is compatible with the integration of graphene nanoribbons and tunneling electrodes for graphene based nanopore DNA sequencing. In addition, the remarkable response of this platform to solution pH enables a sequencing by synthesis approach using ionic current alone. This platform is also well suited for use in diagnostics due to the single protein sensitivity demonstrated, particularly in methylation detection as shown here, applicable to cancer diagnostics.

Fabrication of Graphene-$Al_2O_3$ Nanopores. A 300 nm diameter pore is first formed using a focused ion beam (FIB) tool in a free standing $Al_2O_3$ membrane (FIG. 1a). Graphene, grown via chemical vapor deposition (CVD) is next transferred onto this substrate spanning over the 300 nm $Al_2O_3$ pore (FIG. 1b). This layer is referred to as graphene 1 or g1. Graphene growth conditions are as follows: CVD graphene is grown on 1.4 mil copper foils. The foils are annealed under $Ar/H_2$ flow for 45 mins and graphene is grown under a $CH_4/H_2$ flow at 1000° C., ≈500 mTorr for 20 mins. The resulting Cu/graphene substrates are cooled to room temperature under Ar flow at a rate of ~20° C./min. Transfer to the receiving substrate proceeds as follows: graphene is coated with a bilayer of PMMA (495 K and 950 K), backside graphene on the copper foil is removed in an $O_2$ plasma, and then the backside copper is etched in a 1 M $FeCl_3$ solution. The resultant PMMA/graphene film is wicked onto a glass slide, rinsed in DI water, rinsed in 10% HCl in DI to remove residual metal particles and wicked onto the receiving substrate. After the graphene dries on the receiving substrate, PMMA is removed in a 1:1 Methylene Chloride:Methanol solution. The transferred film is annealed in a CVD furnace at 400° C. under $Ar/H_2$ flow to remove any residual PMMA. Following the annealing step, electron diffraction imaging and Raman Spectroscopy are used to evaluate the quality of the graphene (FIG. 1b right column). Next, 1.5 nm of metallic Aluminum is evaporated onto the graphene to form an adhesion layer followed by 6.5 nm of $Al_2O_3$ (dielectric layer 1 or d1) deposited via atomic layer deposition (ALD). Process steps 1b and 1c are repeated once more i.e. growth and transfer of a second graphene layer (g2) and repeat $Al/Al_2O_3$ deposition (d2) resulting in a graphene/$Al_2O_3$/graphene/$Al_2O_3$ stack as shown in FIG. 1c. Note, a gold pad is used to contact the g2 layer at its edge allowing the application of gate potentials to the conductive g2 layer. Finally, a field emission gun TEM is used to form a nanopore in this stack as shown in FIG. 1d.

Figure 2:
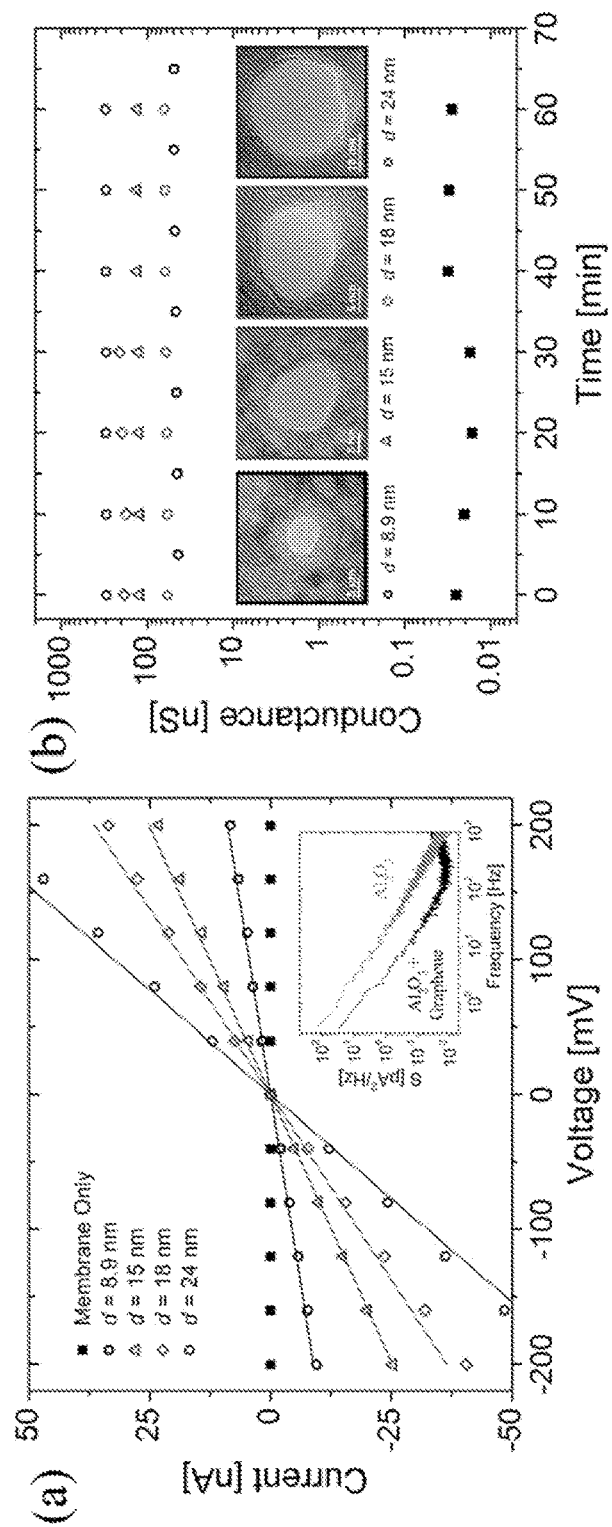
FIG. 2. Graphene-$Al_2O_3$ nanopore electrical characterization. (a) IV characteristics of graphene-$Al_2O_3$ nanopores of varying size show linear response. Note that the membrane has near negligible conductance. Fitted data is numerically computed. (Inset) 1/f noise of graphene-$Al_2O_3$ nanopores is comparable to if not better than $Al_2O_3$ nanopores. (b) These membranes and nanopores give stable conductance values as shown dependent on nanopore diameter.

Electrical Characterization of Graphene-$Al_2O_3$ Nanopores. The current-voltage characteristics of graphene-$Al_2O_3$ nanopores are shown in FIG. 2 for pores of varying size in 1M KCl, 10 mM Tris, 1 mM EDTA, pH 8. Linear IV curves are generally observed suggesting a symmetric nanopore structure as previously reported for $Al_2O_3$ nanopores. The IV characteristics of four pores of varying diameter are shown in FIG. 2. Also shown are fits to the data constructed using numerical simulations. FIG. 2 also shows the conductance stability of these same pores as a function of time. Stable conductance values are obtained for over 60 minutes, confirming the stability of these pores in ionic fluid. Conductance values after drilling a nanopore are several orders of magnitude higher than the conductance of a graphene-$Al_2O_3$ membrane with no pore as seen in FIG. 2b (solid squares).

Figure 3:
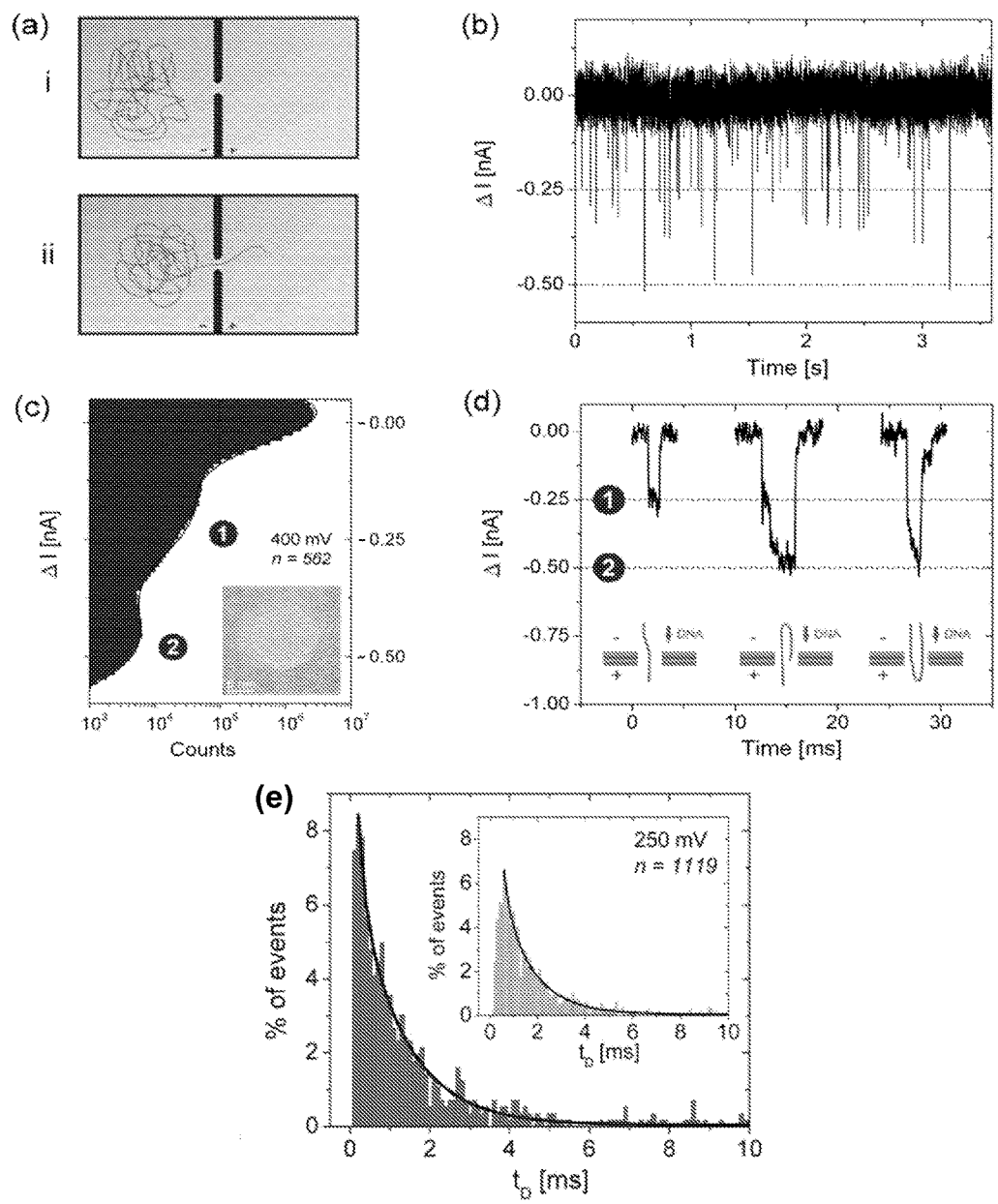
FIG. 3. λ-DNA Transport through a graphene-$Al_2O_3$ nanopore. (a) Schematic showing transport of λ-DNA through a nanopore. λ-DNA has a radius of gyration of ~1.33 μm and hence forms a large supercoiled ball in an electrolyte solution as shown. (ii) DNA threading process in a nanopore. (b) Characteristic translocation events of λ-DNA through an 11.3 nm graphene-$Al_2O_3$ nanopore. Clear downward blockades are observed. (c) Event current histogram constructed from 562 translocation events recorded at 400 mV. Two distinct current peaks are observed; 1, representing linear dsDNA transport through the pore, and 2, representing folded DNA transport through the pore. This phenomenon is illustrated in more detail in (d) and a summary histrogram in (e).

Detection of dsDNA using graphene-$Al_2O_3$ Nanopores. To study the transport properties of graphene-$Al_2O_3$ nanopores, experiments are performed involving the translocation of λ-DNA, a 48.5 kbp long, dsDNA fragment extracted and purified from a plasmid. Given the relatively small persistence length of dsDNA (54±2 nm), λ-DNA is expected to assume the shape of a highly coiled ball in high salt solution with a radius of gyration, $R_g=\sqrt{2l_pL}\approx1.33$ μm as shown in FIG. 3a (i). Upon capture in the nanopore, the elongation and threading process occurs as shown in part (ii). FIG. 3b illustrates the corresponding current blockades induced by λ-DNA as it translocates through an 11.3 nm diameter pore at an applied voltage of 400 mV in 1M KCl, 10 mM Tris, 1 mM EDTA pH 10.4. The λ-DNA concentration used in these experiments is 100 ng/μl. High pH buffer is used to minimize electrostatic interactions between the bottom graphene surface of the nanopore and the negatively charged dsDNA molecule. Also, it is important to note that $Al_2O_3$ is negatively charged at this pH value (isoelectric point of $Al_2O_3$ is 8-9) and thus will not electrostatically bind DNA. Thus, these experimental conditions yield repeatable DNA translocation through grahene-$Al_2O_3$ nanopores.

Two distinct blockade levels are observed in λ-DNA translocation experiments, a shallow blockade corresponding to linear dsDNA transport, and a deeper blockade level corresponding to folded DNA transport as seen in FIG. 3b and the current blockage histogram of FIG. 3c. Note that ΔI here represents the current blockage induced by dsDNA relative to the baseline current at a particular voltage (400 mV in this case). The current histogram of FIG. 3c is constructed from 562 individual DNA translocation events. To confirm that these events are indeed due to DNA translocation and not simply interactions with the pore surface, the effect of voltage on translocation time is probed. Voltage dependent DNA transport is observed, translocation times, $t_D$, decreasing with increasing voltage, corresponding to an increased electrophoretic driving force. Measured values for translocation time are $t_D$=1.81±2.77 ms at 400 mV (FIG. 3(e)) and $t_D$=2.66±4.08 ms at 250 mV from n=1119 events (FIG. 3(e) inset). The broad distribution of translocation times is representative of translocations involving significant interactions with the pore surface.

The λ-DNA translocation experiments described in this example show that the graphene-$Al_2O_3$ nanopore is highly sensitive at detecting not only the presence of a single molecule, but also discriminating its subtle secondary structure (folded or unfolded). Indeed, this system may read the topographic structure of protein bound DNA fragments and or secondary structures that form in ssRNA. Below, protein-DNA binding experiments involving estrogen receptor α to its cognate binding sequence are described.

EXAMPLE 2

Detection of Protein-DNA Complexes with Single Protein Resolution

Figure 4:
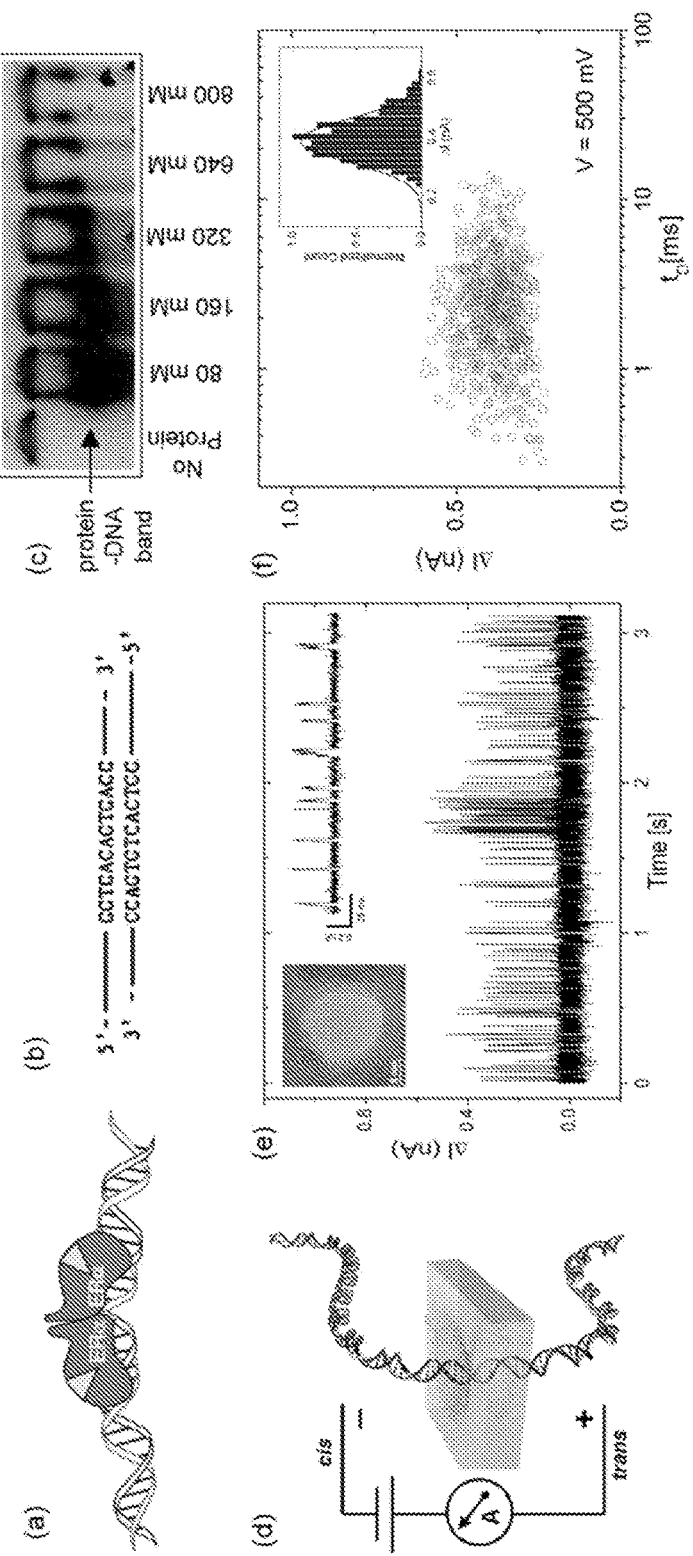
FIG. 4. DNA-protein binding: Transport of ERα/ERE through a Graphene/$Al_2O_3$ Nanopore (a) Schematic of ERαbound to DNA containing a single ERE. (b) ERE sequence (c) Gel-shift assay confirming the formation of the ERα/ERE complex at low salt concentrations. At salt concentrations >320 mM KCl, no protein-DNA band is seen. (d) Schematic showing dsDNA transport through a nanopore. (e) The introduction of the ERα/ERE complex into a 14 nm diameter pore resulted in current enhancements (upward spikes) (f) Translocation time versus current enhancement scatter plot for ERα/ERE (Inset) Current enhancement histogram shows a Gaussian distribution with a peak at 0.4 nA. (g) RecA-coated DNA translocation sample current traces through 23 nm diameter graphene $Al_2O_3$ nanopore at 500 mV applied voltage in 1M KCl, 10 mM Tris, 1 mM EDTA, and electrolyte pH of 8. $I_{BL}$ is baseline current, and downward spike corresponds to transport of either free RecA protein or single/multiple RecA-coated DNA molecules through the pore. The inset is a TEM image of the nanopore with a scale bar of 10 nm. (h) Event density plot constructed from 1368 translocation events, showing current blockage versus translocation time ($t_D$) at 500 mV applied bias. Legend bar represents number of events. (i) Current blockage histogram at 500 mV. Three distinct peaks are observed with Gaussian fits representing the transport of unbound RecA protein, single RecA-coated DNA molecules, and simultaneous transport of multiple RecA-coated DNA molecules. (j) High temporal resolution current traces showing the transport of RecA coated dsDNA: i. Free RecA protein translocation. Events are fast and low amplitude. ii. Single RecA DNA translocation. Events are deeper in amplitude and longer than those observed with free RecA. iii. Simultaneous translocation of multiple RecA coated DNA molecules. Translocation events are longer and higher amplitude than those observed in the single RecA DNA case.
Figure 4:
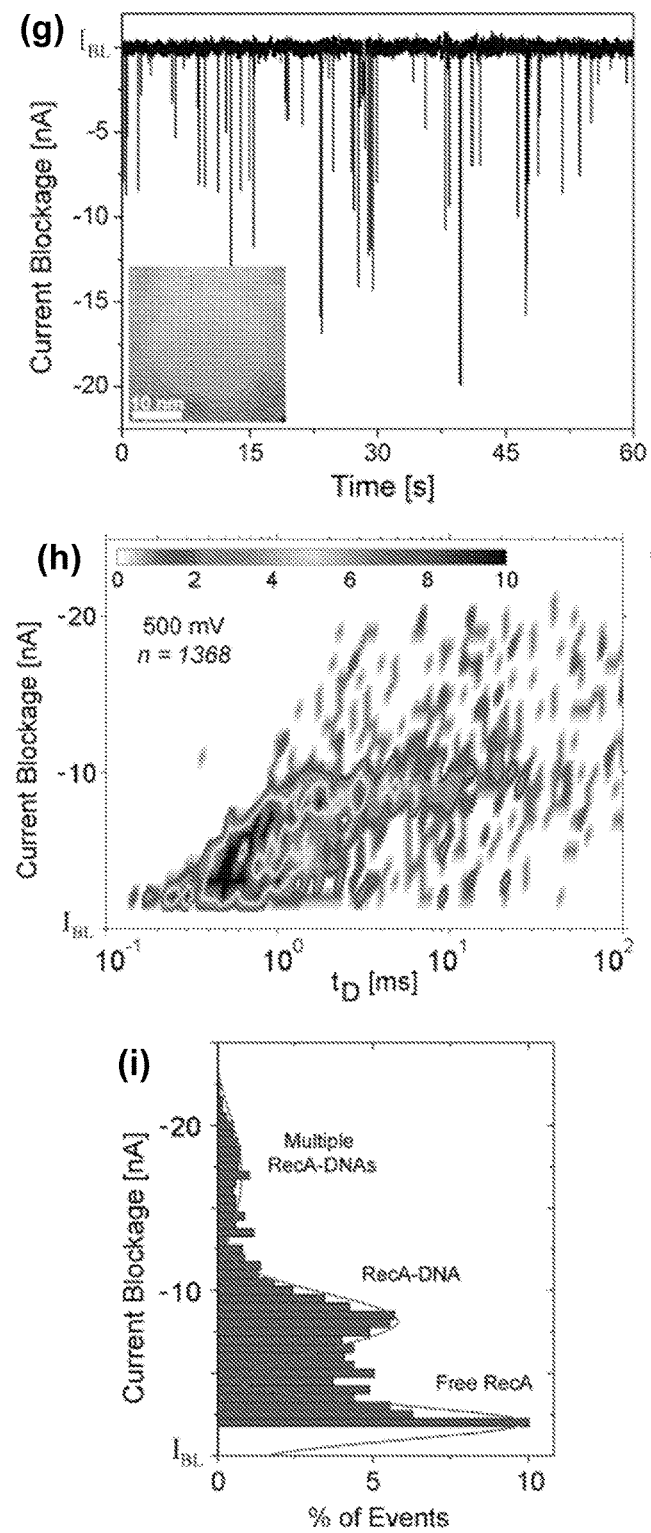
Figure 4:
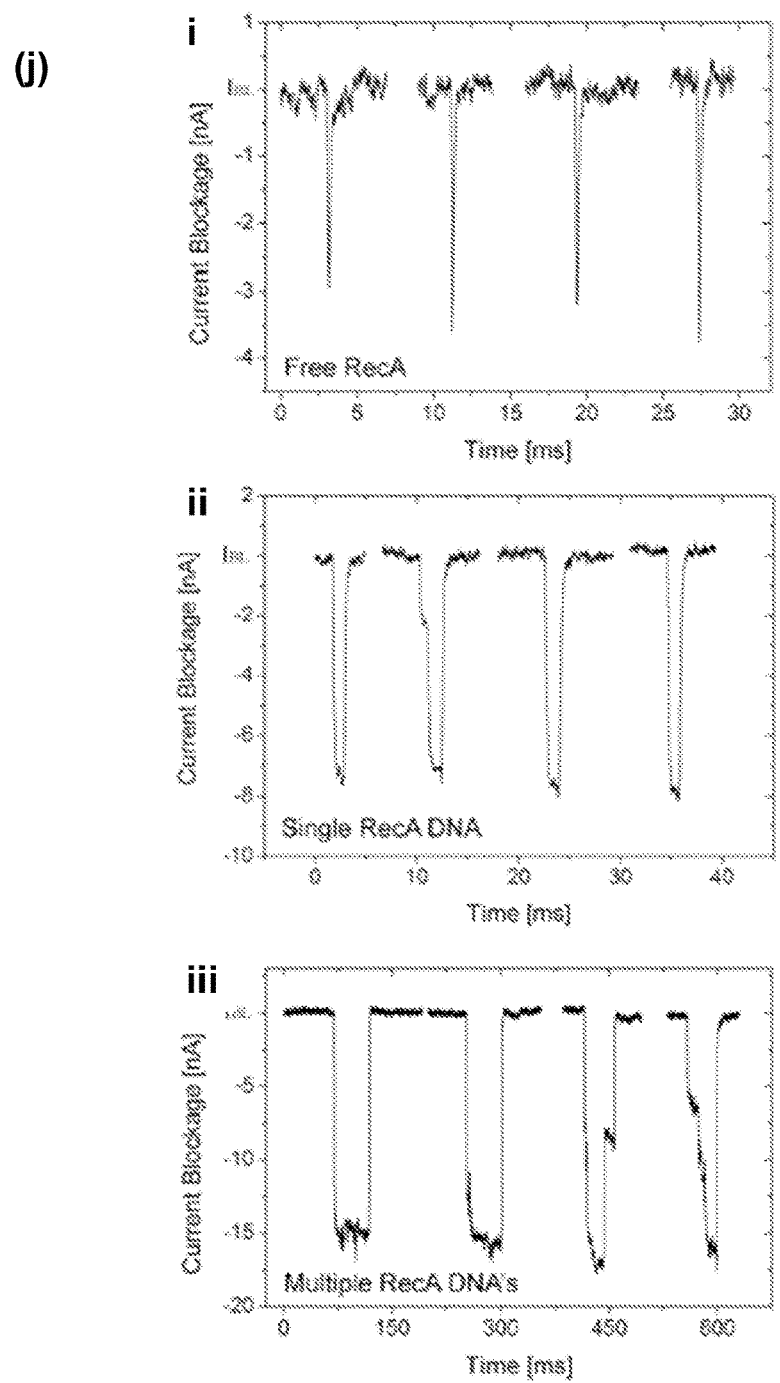

The translocation of protein-DNA complexes through a graphene/$Al_2O_3$ nanopore with the resolution of a single protein is shown in FIG. 4. The model DNA-protein system used in these studies is ERα bound to a 50 bp long probe containing a single ERE, the cognate binding sequence for the ERα protein. DNA-bound ERα primarily serves as a nucleating factor for the recruitment of protein complexes and is involved in key biological processes including oxidative stress response, DNA repair, and transcription regulation. A schematic showing the binding of ERα to dsDNA containing a single ERE and the ERE sequence itself are shown in FIGS. 4a and 4b respectively. FIG. 4c shows a gel shift assay, ERα/ERE binding being observed exclusively at low salt concentrations. The detection of protein-DNA complexes using a nanopore is analogous to dsDNA detection as shown in FIG. 4d. Notably, the transport of the ERα/ERE complex through a ~14 nm diameter pore in 80 mM KCl results in current enhancements (FIG. 4e), likely due to counterion condensation on the complex locally increasing pore conductance during transport as previously reported in DNA transport studies at low salt. A translocation time versus current enhancement scatter plot is shown in FIG. 4f. The most probable translocation time for this 50 bp long DNA probe at 500 mV with a single bound ERα protein is ~3 ms, two orders of magnitude slower than the estimated translocation time for a 50 bp dsDNA alone.

Another system examines recombination protein A, known to form stable nucleoprotein filaments on double-stranded DNA in the presence of magnesium and ATPγS. This model protein plays a central role in homologous recombination and DNA repair in prokaryotes. RecA-coated DNA molecules were prepared and provided by NABsys (Providence, R.I., USA) using a documented process (Smeets et al. Nano Lett. 2008, 9:3089-3095). The transport of this protein-DNA complex through a graphene-$Al_2O_3$ nanopore should induce significantly deeper current blockades relative to native dsDNA, as the effective diameter of this nucleoprotein filament is 7.5±0.5 nm. FIG. 4g shows nanopore current versus time for the transport of 8 kbp long RecA-coated dsDNA molecules through a 23 nm diameter graphene-$Al_2O_3$ nanopore in 1 M KCl, 10 mM Tris, 1 mM EDTA, pH 8 electrolyte at an applied voltage of 500 mV. Deep current blockades are observed during the translocation of the nucleoprotein filament through the pore with significantly higher signal-to-noise ratio (SNR) relative to native dsDNA (higher temporal resolution traces are shown in FIG. 4j). FIG. 4h shows an event density plot of current blockage versus translocation time (tD) constructed from 1368 individual RecA-related translocation events; the corresponding event amplitude histogram is shown in FIG. 4i. Two categories of transport events are clearly distinguishable: fast, low-amplitude events corresponding to the transport of unbound or free RecA protein as previously shown in SiN nanopores, and slower, higher amplitude current blockage events corresponding to the transport of single RecA-coated DNA molecules. The translocation time scales for the two event categories described are consistent with that reported in RecA-DNA translocation experiments in SiN nanopores (Smeets et al.; Kowalczyk et al. Nano Lett. 2009 10:324-328). Interestingly, a third high-amplitude peak at a current blockage value of about 18 nA is also observed in FIG. 4i. This may correspond to the simultaneous transport of multiple RecA-coated DNA molecules through the nanopore.

This example confirms that a multilayered graphene/$Al_2O_3$ nanopore can measure a biological parameter related to a single protein bound to dsDNA, and can be used in applications for detecting and spatially mapping single bound proteins on a DNA molecule.

EXAMPLE 3

Methylation Analysis

Current methods for gene based methylation analysis are highly labor intensive, require large sample volumes, suffer from high per run cost and in most cases lack the sensitivity needed to derive useful clinical outcomes. In contrast, a nanopore based approach to methylation analysis for early cancer detection, though a radical departure from current clinical paradigms, may deliver the sensitivity and speed needed in extracting useful clinical information, relevant to patient outcome. Nanopore based techniques are well suited for gene based methylation analysis due to their ability to (1) detect target molecules at extremely low concentrations from minute sample volumes, (2) detect a combination of methylation aberrations across a variety of genes (important in monitoring disease progression and prognosis), (3) detect subtle variations in methylation patterns across alleles that would not be detected using bulk ensemble averaging methods such as PCR and gel-electrophoresis, (4) perform rapid methylation analysis (hundreds of copies of the same gene analyzed in minutes), (5) reduce cost (small reagent volumes needed), (6) simplify experimental and analysis steps by eliminating cumbersome PCR, DNA sequencing and bisulfite conversion steps.

Figure 5:
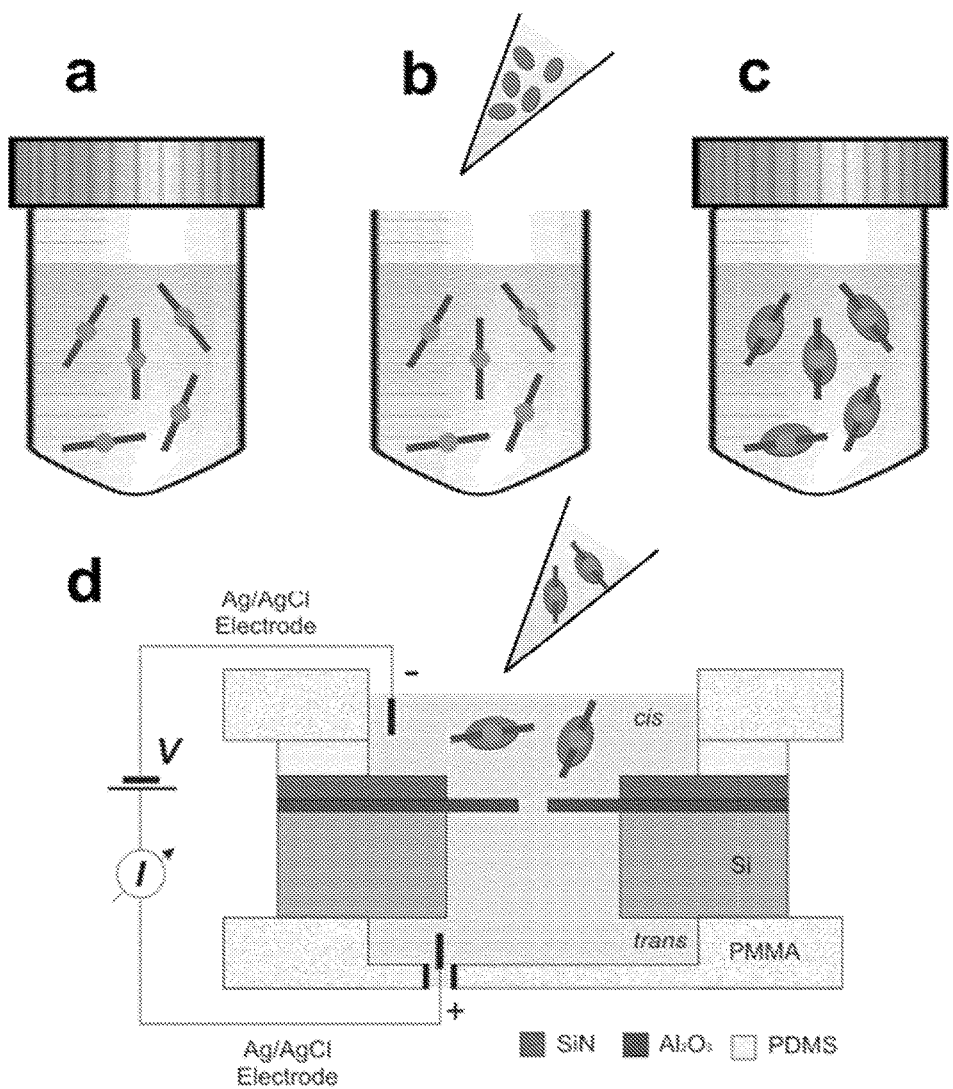
FIG. 5. (a) Start with enzyme methylated DNA fragments. (b) Add Methylated DNA binding protein to methylated DNA samples. (c) Incubation step to form stable MBD protein bound DNA complexes. (d) Introduction of MBD Protein-DNA complex into the cis chamber of the nanopore fluidic setup.

Analysis Protein bound Methylated DNA using Electrical Current Spectroscopy. The nanopore based methylation analysis process is illustrated in FIG. 5. First, methylated DNA molecules are combined with methyl-CpG binding proteins to form protein bound DNA complexes (FIGS. 5b and 5c). The methyl-CpG-binding protein family (MBD) consists of five proteins, MeCP2, MBD1, MBD2, MBD3 and MBD4, each containing a methyl-CpG-binding domain (MBD) that allows them to bind to methylated DNA. Any of these are used to label methylated CpG dinucleotides.

MeCP, MBD1 and MBD2 are selected as they bind specifically and exclusively to a single methylated CpG dinucleotides in vitro, and have been identified as critical components in transcriptional repression. The specificity of these proteins are used to label methylation sites along a methylated DNA molecule. The MBD-DNA complex is introduced into the cis chamber of the nanopore fluidic setup as shown in FIG. 5d. Under an applied potential, these protein bound, methylated DNA fragments translocate through the pore resulting in characteristic current blockades, representative of the methylation status of the molecule.

Figure 6:
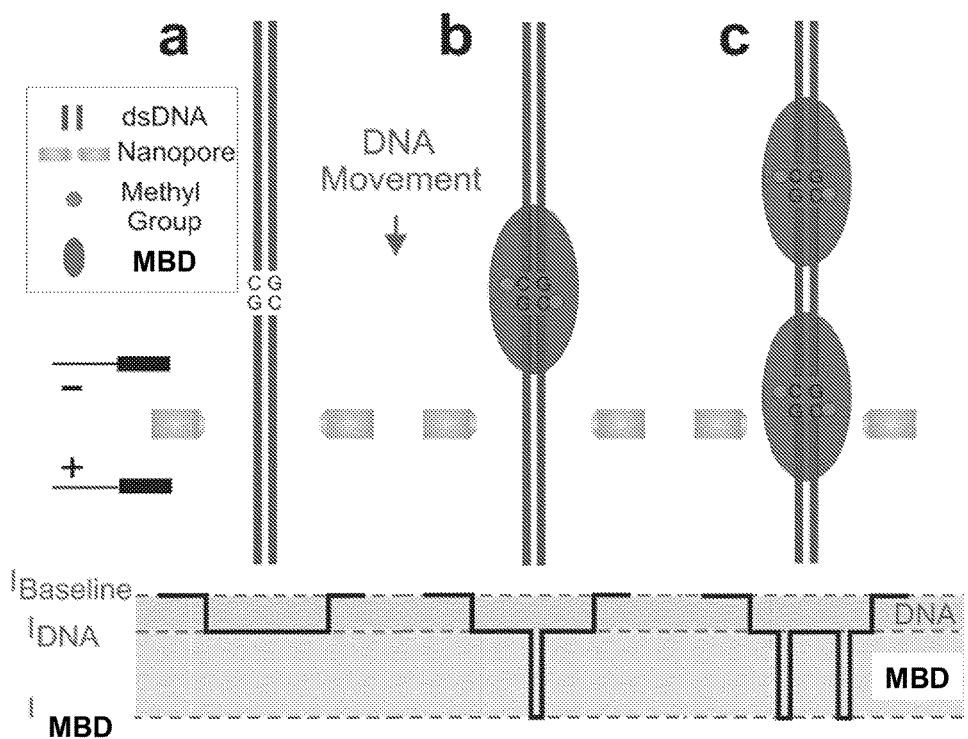
FIG. 6. (a) Passage of unmethylated DNA; shallow current blockades are seen. (b) Passage of DNA with MBD, such as MBD2 (MBD1, MeCP may also be used), bound to a single methylated CpG dinucleotide. Two blockade levels are seen: shallow blockade due to DNA, deep blockade due to MBD. (c) Passage of DNA with multiple bound MBD proteins. Current signature permits methylation quantification and mapping of methylation sites along a single molecule.

Methylation Determination: A single methylated DNA molecule from an unmethylated DNA fragment of equal length using nanopore based current spectroscopy methods (FIG. 6). The passage of unmethylated DNA through the pore produces only a slight deviation in the baseline current as illustrated in FIG. 6a. The passage of an MBD protein bound DNA fragment through the pore, however, results in a very different current signature (FIG. 6b). As the drop in pore current is related to the cross section of the translocating molecule, deeper blockades are observed when the large, bound protein traverses the pore. Two distinct blockade levels occur, the first corresponding to regions of DNA that do not contain bound proteins ($I_{DNA}$), and the second corresponding to regions containing the MBD protein ($I_{MBD}$). Gel shift assays have shown that fragments with multiple bound MBD proteins corresponding to multiple methylated CpG dinucleotides migrate slower through the gel and can be resolved with single protein resolution. Furthermore, each additional bound protein significantly reduces the mobility of the complex in the gel. This is attributed to two factors; (1) the high molecular weight of MBD2 relative to the short DNA fragments, (2) the positive charge of MBD2 in pH 8.0 buffer (isoelectric point of 9.1). Thus, under normal pore operating conditions (pH 7-8), MBD bound DNA translocation is expected.

Methylation Quantification and Mapping: Current spectroscopy allows for the mapping of methylation sites along a specific DNA fragment and to quantify overall level of methylation. The process is illustrated in FIG. 6c. The presence of multiple fully methylated CpG dinucleotides along a single DNA molecule facilitates the binding of multiple MBD proteins per DNA, each of which produces a deep current blockade during translocation. The translocation of fragments with multiple bound proteins results in an electrical readout as shown in FIG. 6 that resembles the spatial distribution of proteins along that fragment. This can then be used to determine the distribution of methylated CpG dinucleotides along the interrogated DNA fragment. The current signature can also be used to quantify the extent of methylation based on the number of deep current blockades per event.

This raises the question as to the spatial resolution of the technique. DNase I footprinting confirm that the MBD of MeCP2 protects a total of 12-14 nucleotides surrounding a single methylated CpG pair. As the MBD of MeCP2 and MBD2 are homologous, we expect that MBD2 will cover approximately 12-14 bp of DNA upon binding also. Additional methyl CpG dinucleotides within this 12-14 bp domain are not available to bind to other MBD2 molecules, thereby limiting the spatial resolution of this technique. It is therefore expected that the nanopore platform can resolve individual MBD molecules positioned along a single DNA strand with good resolution given its high signal-to-noise ratio. The length-wise topographic reading process described in this example allows for quantification of methylation levels and to map methylation distributions along a single DNA fragment, and can be extended to the analysis of specific genes. This highly sensitive nanopore based methylation analysis technique is useful in medical diagnostics.

EXAMPLE 4 pH Dependent Response of Graphene-Al$_2$O$_3$ Nanopores

Because of the high surface-to-volume ratio in nanopores, surfaces potentially have a very large effect on pore conductance at low salt concentrations. The surface charge characteristics and pH response of graphene-Al$_2$O$_3$ nanopores in particular can help facilitate a sequencing by synthesis approach by monitoring local changes in pH through the release of H$^+$ ions during the incorporation of nucleotides using a DNA polymerase. At high salt concentrations, charge carriers in the solution dominate the ionic current through the pore. The conductance scales linearly with the number of charge carriers, as observed experimentally, and surface charge has negligible effect. At low KCl concentrations, however, the total current through the nanopore is a combination of the contributions of the bulk concentration of ions in solution and the counterions shielding the surface charge (electroosmotic flow). Above the isoelectric point of Al$_2$O$_3$ (~pH 8-9), the surface charge in the pore is negative resulting in a double layer of condensed K ions, and below the isoelectric point, the surface charge is positive resulting in a double layer of condensed Cl counterions as shown in FIG. 7a. Pore conductance as a function of KCl concentration and pH is shown in FIGS. 7b and 7c respectively for 18±1 nm diameter and 8±0.5 nm diameter graphene-Al$_2$O$_3$ nanopores. Clearly the conductance of a graphene-Al$_2$O$_3$ nanopore is strongly influenced by local pH.

Figure 7:
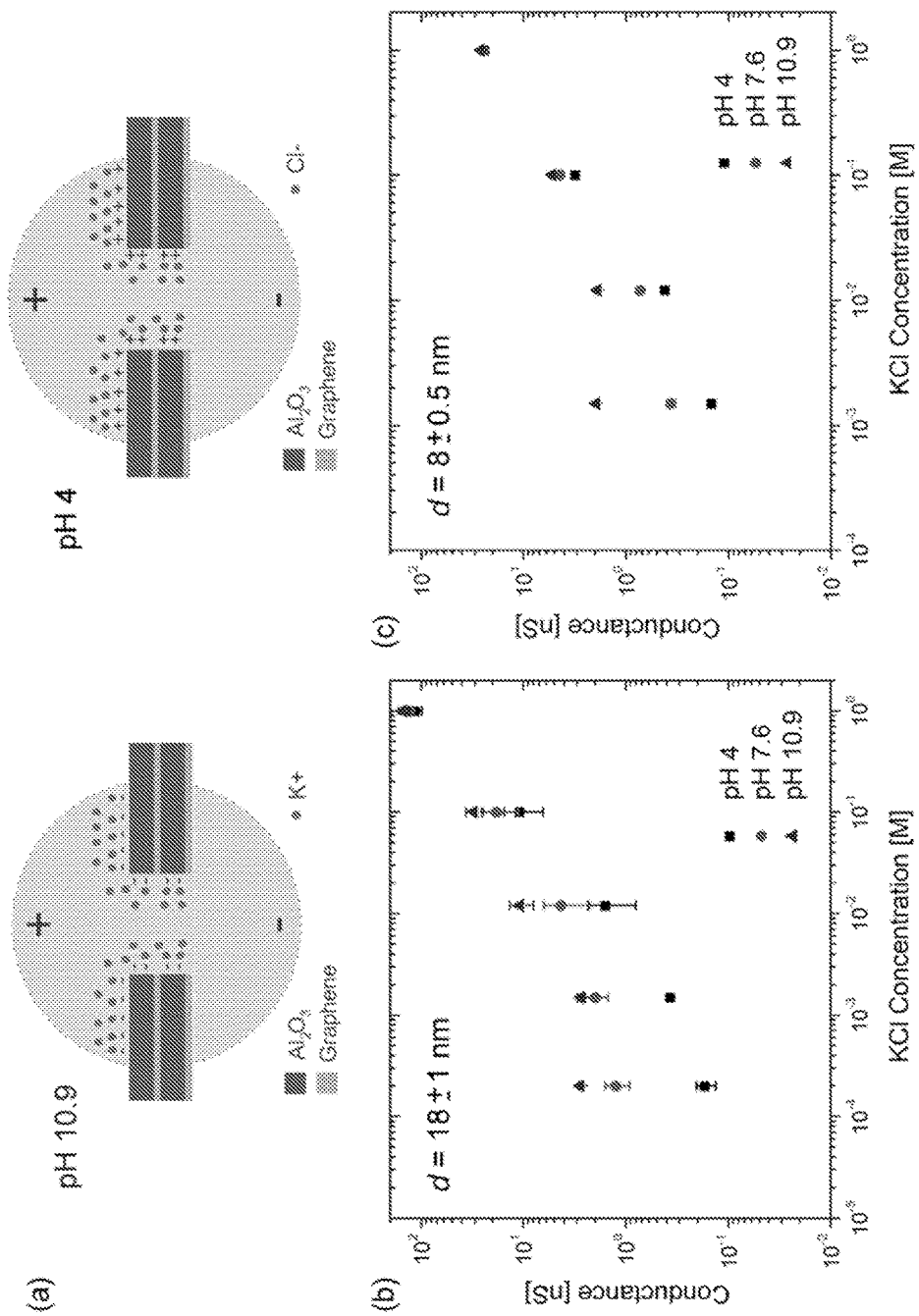
FIG. 7. (a) Schematics showing counterion condensation on the pore surface at both high pH and low pH assuming an isoelectric point of the nanopore is in the pH range of 5-7. (b) pH response of a 18±1 nm diameter graphene-$Al_2O_3$ pore as a function of KCl concentration and solution pH. (c) The effect of pore size: pH response of a 8±0.5 nm diameter graphene-$Al_2O_3$ pore as a function of KCl concentration and solution pH. Strong pH response is observed in both cases.

Conductance saturation is clearly observed at pH 10.9 as salt concentration is reduced, suggesting the presence of a highly charged, negative pore surface under these high pH conditions. In contrast, conductance saturation is not observed at pH 4 even at very low KCl concentrations (FIG. 7), suggesting that the pore is only weakly charged at this pH. The pH 4 response more closely resembles bulk behavior where the effects of surface charge on channel conductance are minimal. FIG. 7c illustrates the pH response of a smaller 8±0.5 nm diameter pore. Similar trends are seen as in FIG. 7b with lower pore conductance being observed at lower pH. Interestingly, saturation/plateauing in the conductance at pH 10.9 is observed at KCl concentrations starting at 10 mM, an order of magnitude higher than in FIG. 7b. This result is expected as Debye layer overlap and surface effects will begin to dominate at higher salt concentrations in smaller pores. The Debye screening length is approximately 3 nm in 10 mM KCl and thus is comparable to the 8 nm diameter of the pore in FIG. 7c. Thus, surface charge effects are expected to be significant at this relatively high salt concentration.

The pH response of graphene-$Al_2O_3$ nanopores is significantly more pronounced than the pH response of SiN and $TiO_2$ nanopores as well as $SiO_2$ nanochannels. This may in part be due to the presence of graphene in conjunction with the high surface charge density of $Al_2O_3$. Modulating the surface potential of the nanopore using solution pH can indeed modulate the conductance of the pore. This platform is suited to monitoring local pH during the incorporation of single nucleotides using DNA Polymerase, facilitating a sequencing by synthesis approach.

EXAMPLE 5

Graphene Gated Nanopores and Shaped Graphene Layers

Figure 8:
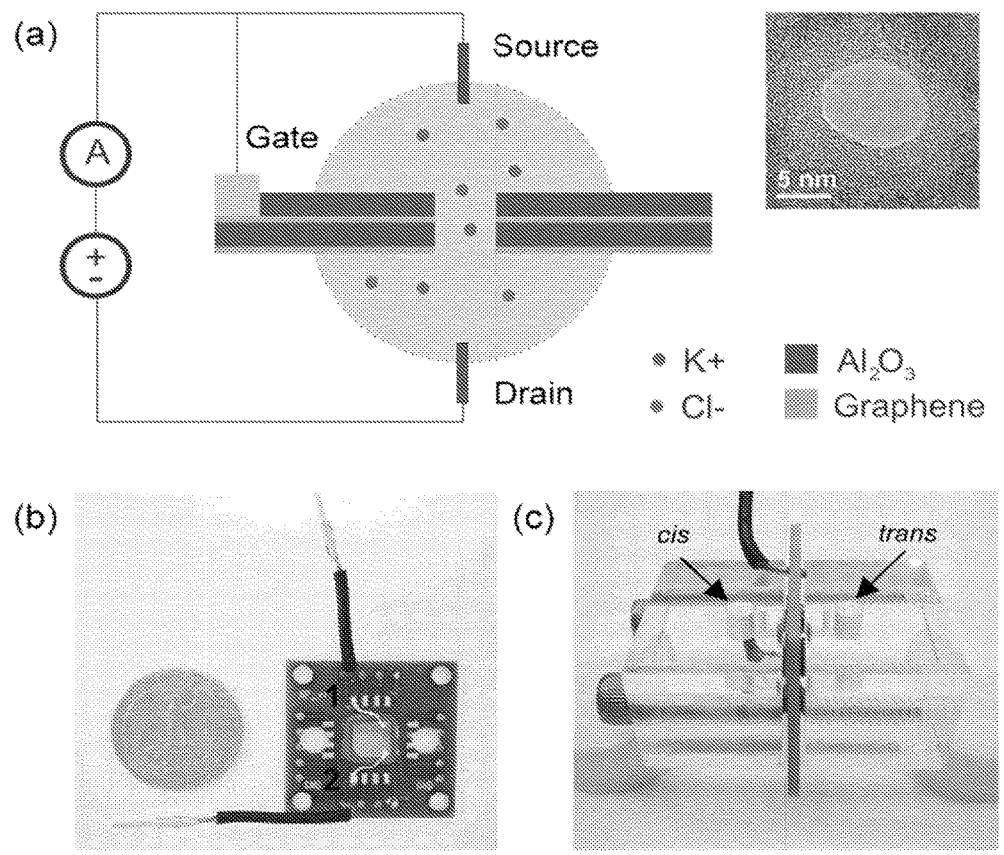
FIG. 8. (a) Graphene gated nanopore measurement setup. Graphene layer 2 (g2) is contacted using a 250 nm Ti/Au pad at the edge of the nanopore chip. Gate and source are tied together in all current measurements. (b) Nanopore chip is mounted on a PCB and the Ti/Au pads are contacted using In wires. The resistance across terminals 1 and 2 is typically ≤15 kΩ confirming the presence of a conducting graphene sheet after fabrication. (c) PCB with a nanopore chip is mounted in a fluidic setup as shown, which isolates the metal contact pads from the conductive solution.

The concept of an electrically gated solid-state nanopore has been discussed, but the use of graphene as the gate material and the implementation of such a system was not previously demonstrated. A third electrode embedded in the nanopore is particularly attractive as it can be used to modify the electric fields in the pore and could be used to slow down or capture a translocating DNA molecule, a key step for implementation of nanopore sequencing. The effects of an insulated third electrode (30 nm thick TiN layer) on the conductances of both nanochannels and nanopores have been described. This example, however, discusses using graphene, of thickness only a few monolayers, as a nanopore electrode or a gate electrode. The realization of such a structure involves modifications to the architecture shown in FIG. 8a (also shown in FIG. 1c). These modifications include the contact of graphene layer 2 (g2) in FIG. 1 with a 250 nm evaporated Ti/Au pad prior to atomic layer deposition of dielectric 2 (d2), as shown in FIG. 1c. The nanopore is next drilled in the contacted stack. After drilling the pore, the nanopore chip is epoxied to a custom designed PCB and the Ti/Au pads contacting the graphene gate are connected using indium wires to external PCB pads (1 and 2) as shown in FIG. 8b. FIG. 21B illustrates and independently energizable and detectable graphene gate electrode via the Ti/Au pad connected to a power supply and detector. The resistance across pads 1 and 2 after connecting the chip is in the range of 5-15 kΩ typically, confirming the presence of a conductive graphene sheet on the nanopore chip after fabrication. The PCB mounted nanopore chip is next inserted into a custom designed fluidic setup as shown in FIG. 8c. Care is taken to ensure that the Ti/Au pads are isolated from the fluid to prevent leakage currents.

Nanopore measurements with the graphene gate are conducted by tying the gate node to the source electrode, as shown in the schematic of FIG. 8a. The source and gate are tied to prevent leakage currents from flowing between the source and gate nodes. Even though graphene technically should act as a non-Faradaic electrode with very little electron exchange occurring in an ionic solution under low applied biases, the presence of defects and grain boundaries, characteristic of CVD grown graphene, may give rise to such a leakage current.

Figure 9:
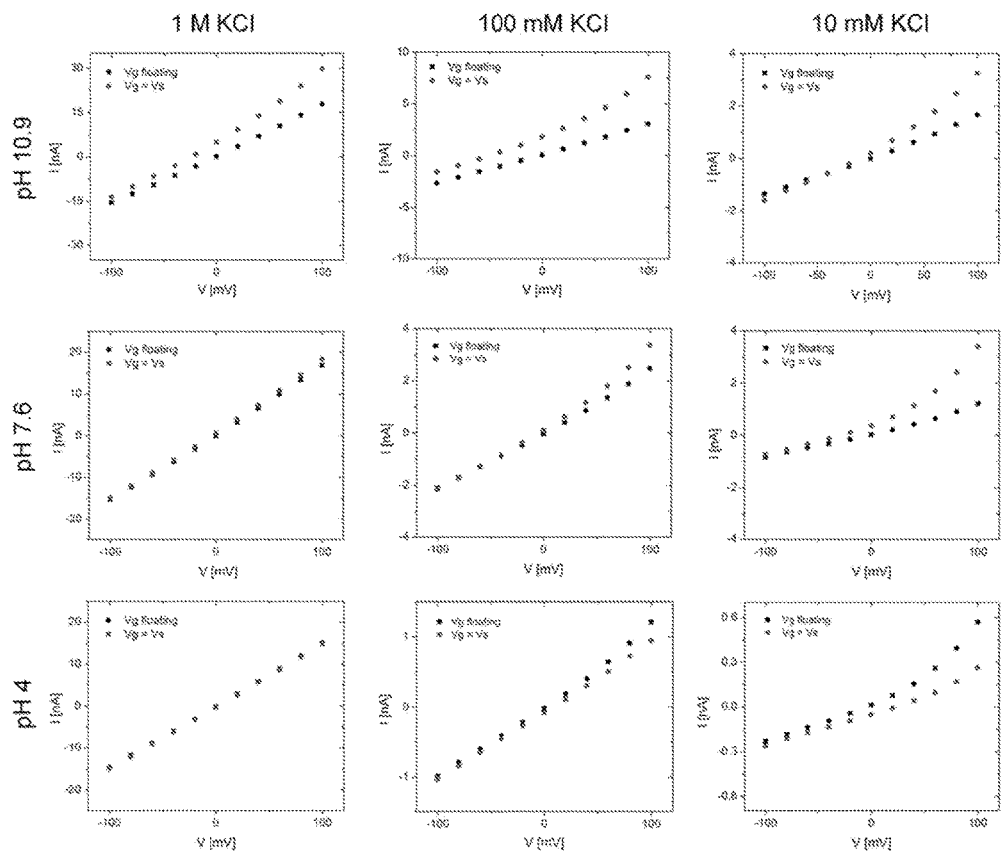
FIG. 9. Current-voltage (I-V) characteristics of a 19 nm diameter graphene-$Al_2O_3$ nanopore with gate (graphene layer 2) tied to the source and the gate left floating. The three rows represent I-V measurements taken at fixed pH values of 10.9, 7.6 and 4 and the three columns represent I-V measurements taken at fixed KCl concentrations of 1 M, 100 mM and 10 mM. Significant current rectification was observed at pH 10.9 at all salt concentrations probed. This effect was dramatically reduced at pH 4.

FIG. 9 illustrates the effect of connecting the graphene gate (tied gate-source) in graphene-$Al_2O_3$ nanopores versus leaving the gate floating, under a variety of salt conditions and pH values.

A higher conductance level is seen at pH 10.9 and pH 7.6 with the gate connected relative to the floating case. In contrast, lower conductance is observed at pH 4 with the gate connected relative to the floating gate case. Though this current enhancement and reduction is more pronounced as the salt concentration is reduced suggesting an electrostatic effect, this result cannot be attributed solely to an electrostatic modulation of the field in the pore. It is likely that there are also electrochemical currents flowing through the contacted g2 layer, which are more pronounced at higher pH. This potentially explains the significant current amplification observed at 1M KCl, pH 10.9 conditions even though the Debye screening length at this concentration is only ~0.3 nm. This is consistent with the notion that at high pH, OH— can disrupt the $sp^2$ bonding of graphene resulting in charge transfer at the graphene fluid interface. This effect does not occur at low pH values, consistent with the lack of current enhancement observed in our experiments. The current modulation through the pore with the gate connected also cannot be attributed solely to leakage currents. Little variation in leakage current as a function of pH in the voltage range (−100 mV to 100 mV), identical to what is probed in gated nanopore measurements is observed. The results described in this application also suggest that the g2 layer may in fact be used as a trans electrode in the pore given the significant current transfer that is observed at this interface. This layer can serve as a sensitive electrode in future DNA translocation experiments. The application of local potentials in the pore via this third electrode is also useful in slowing or trapping DNA molecules in the pore.

Figure 10:
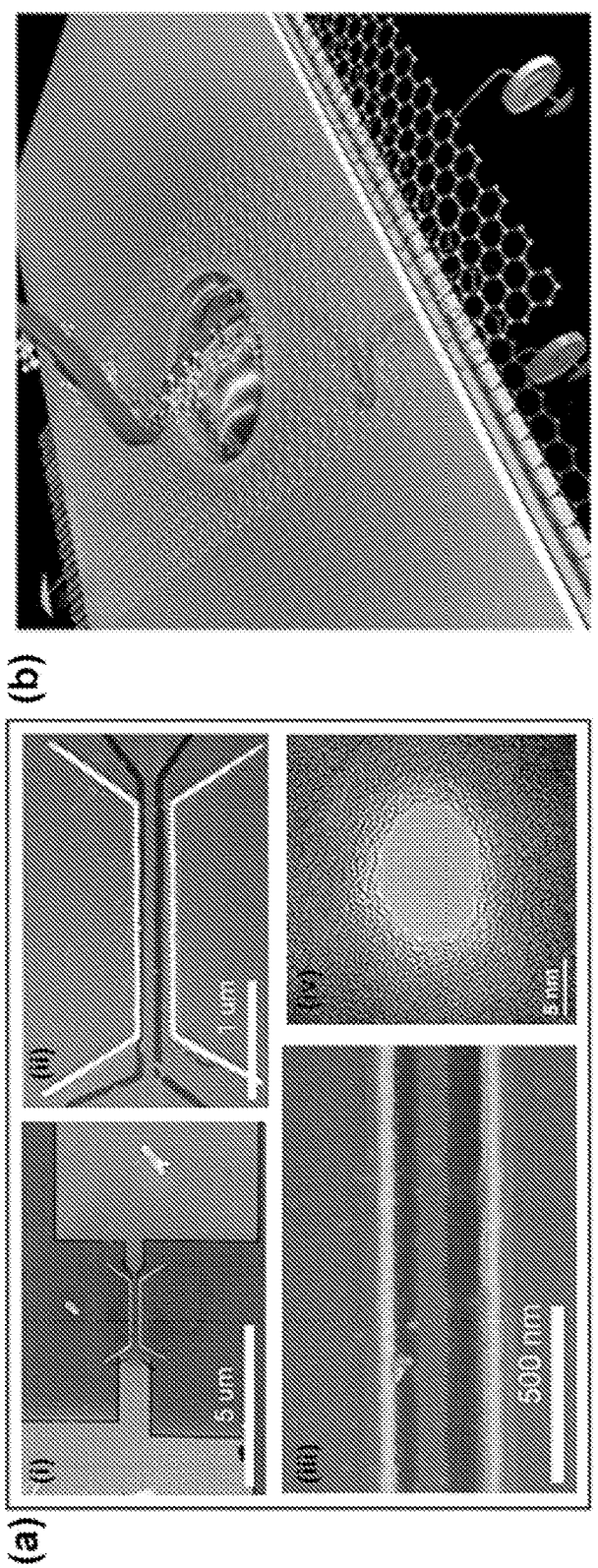
FIG. 10. A graphene nanoribbon with a nanopore for single molecule DNA sequencing. (a) SEM images of the graphene ribbon patterned in graphene layer 2 (g2) in the architecture shown in FIG. 1. (i-iii) Show SEM images of the ribbon with increasing magnification. (iv) A 14 nm pore drilled in the center of the GNR using a TEM (b) A schematic of a graphene nanoribbon on a solid-state nanopore with an embedded graphene gate. The graphene gate can achieve either p-type or n-type behavior for sufficiently small ribbons and to electrostatically control translocation velocity, such as decreasing ssDNA translocation velocity through a nanopore. The graphene ribbon may act as the nucleotide reader with each nucleotide uniquely modulating its transverse conductance. The functionalization of graphene ribbon edges in the nanopore can further enhance nucleotide specific interactions.

A Graphene Nanoribbon-Nanopore for DNA Detection and Sequencing: Theoretical-only feasibility of nucleotide discrimination using a graphene nanoribbon (GNR) with a nanopore in it was recently demonstrated. Nucleotide specific transverse currents through the ribbon are reported in those theoretical studies. This example uses a similar architecture for single molecule DNA sequencing. FIG. 10a shows a series of SEM images showing the fabrication a GNR and the formation a nanopore directly in the ribbon. Note the GNR is formed by patterning the g2 layer shown in FIG. 1. FIGS. 10b and 20b shows the approach to ssDNA sequencing. By measuring transverse current through the ribbon 132 during the passage of ssDNA, the GNR may serve as a nucleotide reader. The embedded graphene gate (layer g1) 602 provides a means to bias the GNR for either p-type or n-type behavior and can slow down DNA translocation electrostatically.

Figure 11:
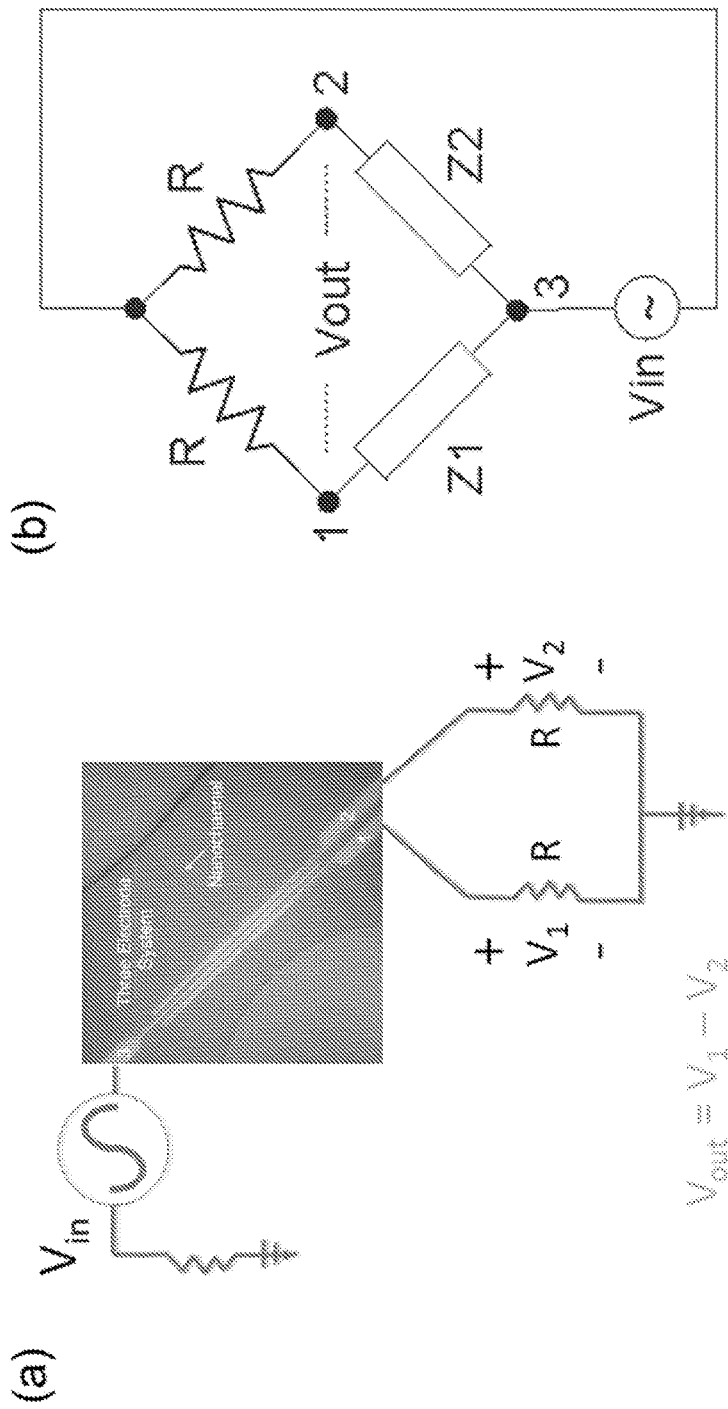
FIG. 11. (a) Wheatstone Bridge electrode architecture in a nanochannel for measuring individual DNAs and proteins using voltage rather than current. (b) Equivalent circuit for this system.

Nanoelectrodes in a Nanochannel as Voltage Sensors. The following electrode architecture (Wheatstone Bridge) in a nanochannel can facilitate the sensing of individual DNA molecules and DNA/protein complexes with very high spatial resolution, facilitating long range haplotype mapping of DNAs and sequencing using a voltage sensing approach. The architecture described here is shown in FIG. 11a and comprises three electrodes placed within a nanochannel, which passes either above or below the electrodes. An AC signal is applied to the center electrode (electrode 3) and the left (electrode 1) and right (electrode 2) electrodes are grounded. The impedance between electrodes 1 and 3 is given by Z1 and the impedance between electrodes 2 and 3 is given by Z2. In solution in the absence of DNA and other species, Z1 and Z2 are balanced due to the symmetry of the architecture, resulting in an output potential of Vout=V1−

V2=0. The equivalent circuit is shown in FIG. 11b. The introduction of DNA or protein results in the following: As a DNA molecule or protein passes through the region between electrodes 1 and 3, it modulates/changes Z1 and is detected as a voltage spike in the output voltage. Similarly, as the molecule passes by the region between electrodes 3 and 2, it modulates Z2 and results in a voltage spike of opposite polarity. This allows for a double count of a translocating molecule as it passes through the nanochannel. Also by comparing the amplitudes of spikes and controlling electrode separations at the nanoscale, it is possible to resolve sensitive topographic information along the length of a DNA molecule, for example, aptamers or bound proteins. Such an architecture can also be arrayed along the length of the channel to provide multiple independent counts on a single molecule for error checking purposes as well as providing length wise topographic information.

Figure 12:
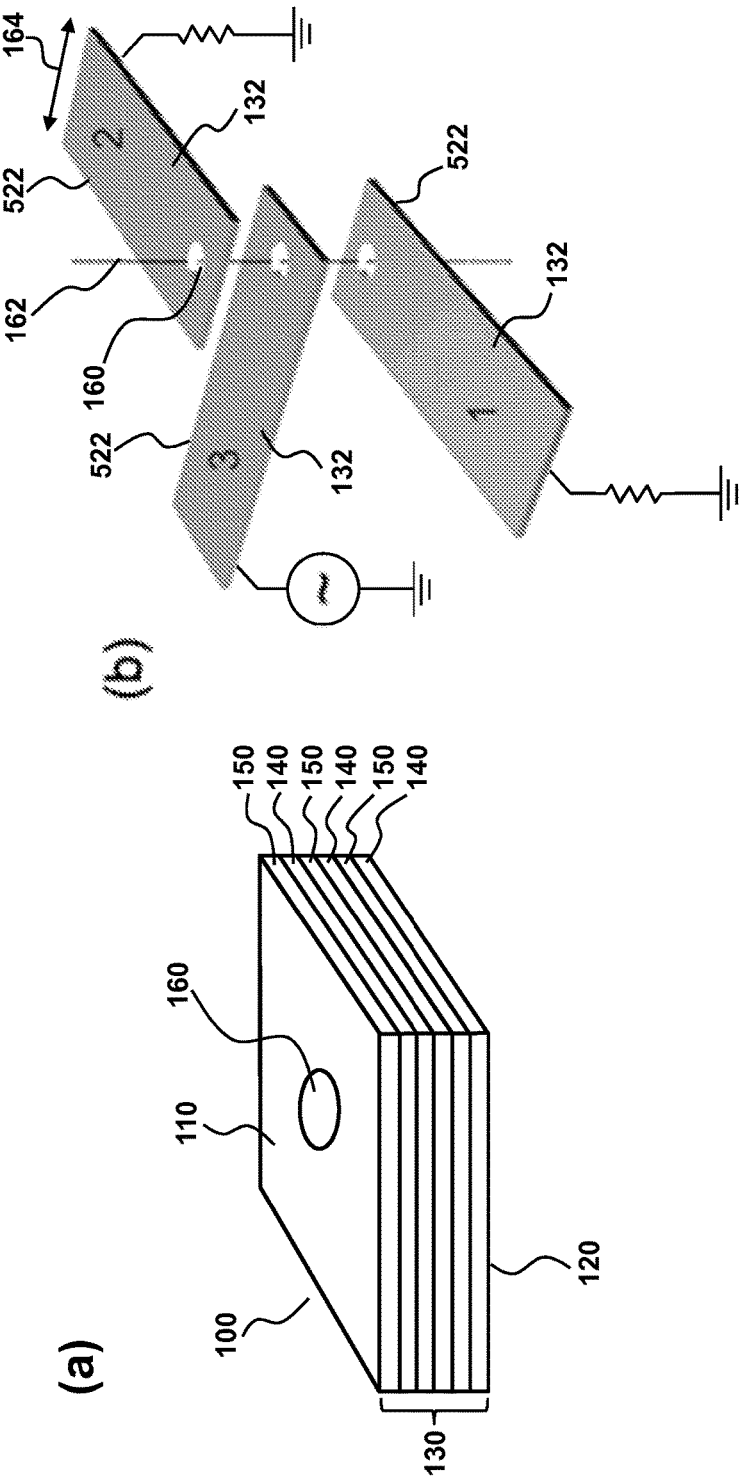
FIG. 12. (a) Multilayer graphene/$Al_2O_3$ structure with a nanopore patterned in the stack. Each graphene layer is patterned to minimize the overlap between the layers as shown in (b). The graphene layers are biased as shown in (b) to form a vertical Wheatstone Bridge architecture allowing individual molecules to be sensed in the nanopore using voltage measurements. Furthermore, this architecture facilitates the sensitive detection of topographic information along the length of the molecule.

Graphene Nanoelectrodes in a Nanopore as Voltage Sensors. This example extends the two layer graphene/dielectric architecture to three layers for applications such as shown in FIG. 12a. Referring to FIG. 12(a), the membrane 100 comprises a multilayer stack 130 of conducting layers (e.g., grapheme) 140 and dielectric 150 layers, in this example $Al_2O_3$. A first surface 110 and second surface 120 define the top and bottom of the stack 130 that face first fluid compartment and second fluid compartment, respectively. A nanopore 160 transits the membrane 100 from the first surface 110 to the second surface 120. Each graphene layer is patterned as shown in FIG. 12b with an overlap region into which a nanopore is drilled (dielectric not shown in FIG. 12b). Referring to FIG. 12b, the nanopore 160 defines a nanopore transit direction 162. Each graphene layer 140 is patterned as desired, including patterned as a nanoribbon graphene layer 132 oriented along a longitudinal axis 522 (corresponding to the direction of a long edge of each nanoribbon) and having a nanoribbon width as indicted by the arrow labeled 164. From FIG. 12b, it is appreciated that the longitudinal direction of any nanoribbon may be characterized as transverse or orthogonal with respect to nanopore transit direction 162. The graphene layers may have an angular offset with respect to each other, in this embodiment adjacent layers have an angular offset relative to each other of 90°. The overlap region is of the order of a 100 nm×100 nm in area and the patterned graphene layers will again be separated by a thin dielectric layer deposited via ALD. The graphene layers are biased as shown in FIG. 12b such as to achieve a vertical Wheatstone Bridge architecture versus the horizontal structure shown in FIG. 11. The central electrode again has an applied AC signal to it and the output potential is again measured across electrodes 1 and 2. By measuring modulations in Z1 (impedance across electrodes 1 and 3) and Z2 (impedances across electrodes 2 and 3), the detection and spatial mapping of molecules using electrical impedance as the molecule passes through the nanopore should be possible. The vertical structure shown here has the added advantage of precise control over the inter-electrode spacing at the Angstrom scale enabling more sensitive topographical measurements along a molecule with respect to the planar architecture shown in FIG. 11.

References

Wanunu, M. & Meller, A. Chemically Modified Solid-State Nanopores. Nano Letters 7, 1580-1585 (2007).

Nam, S.-W., Rooks, M. J., Kim, K.-B. & Rossnagel, S. M. Ionic Field Effect Transistors with Sub-10 nm Multiple Nanopores. Nano Letters 9, 2044-2048 (2009).

Stein, D., Kruithof, M. & Dekker, C. Surface-Charge-Governed Ion Transport in Nanofluidic Channels. Physical Review Letters 93, 035901 (2004).

Karnik, R. et al. Electrostatic Control of Ions and Molecules in Nanofluidic Transistors. Nano Letters 5, 943-948 (2005).

Nelson, T., Zhang, B. & Prezhdo, O. V. Detection of Nucleic Acids with Graphene Nanopores: Ab Initio Characterization of a Novel Sequencing Device. Nano Letters 10, 3237-3242 (2010).

EXAMPLE 6

Nano-Fabricated Graphene-$Al_2O_3$ Nanopores and Nanopore Arrays for the Sensitive Detection of DNA and DNA-Protein Complexes This example describes the fabrication of nanopores and nanopore arrays for the sensitive detection of single DNA molecules and DNA-protein complexes. High density arrays of ~15 nm diameter nanopores are fabricated using electron beam lithography and reactive ion etch steps in $SiN/Al_2O_3$ membranes, facilitating high throughput analysis of single DNA molecules. The fabrication of single nanopores in ultra-thin graphene/$Al_2O_3$ membranes is also reported for detection of DNA-protein complexes. Single protein resolution at low salt concentrations is demonstrated.

Nanopore DNA analysis is an emerging technique that involves electrophoretically driving DNA molecules through a nano-scale pore in solution and monitoring the corresponding change in ionic pore current. This versatile approach permits the label-free, amplification-free analysis of charged polymers (single stranded DNA, double stranded DNA and RNA) ranging in length from single nucleotides to kilobase long genomic DNA fragments with sub-nm resolution. Recent advances in nanopores suggest that this low-cost, highly scalable technology could lend itself to the development of third generation DNA sequencing technologies, promising rapid and reliable sequencing of the human diploid genome for under a $1000. To enable high throughput multiplexed sequencing using solid-state nanopores however, the fabrication of high density nanopore arrays is required. This example demonstrates an optimized process for the fabrication of ~15 nm diameter nanopore arrays in suspended $Al_2O_3/SiN$ membranes using electron beam lithography and dry etch processes, a platform technology well suited for parallel DNA analysis. The incorporation of graphene into solid-state nanopores also holds much promise. The comparable thickness of a graphene monolayer to the 0.32-0.52 nm spacing between nucleotides in single stranded DNA (ssDNA) makes this material particularly attractive for single nucleotide detection with application to electronic DNA sequencing. This example describes the fabrication of single nanopores in robust ultra-thin graphene/$Al_2O_3$ membranes and uses this architecture for the highly sensitive detection of single DNA-protein complexes. The model protein-DNA system used in these studies is Estrogen Receptor a (ERα) bound to a 50 basepair (bp) long probe containing its cognate binding sequence (Estrogen Response Element). These studies demonstrate the single protein sensitivity of this architecture and may be extended to the detection of various other DNA binding proteins, including transcription factors, nucleases and histones.

The principle of nanopore sensing is analogous to that of a Coulter counter. A nano-scale aperture or nanopore is formed in an insulating membrane separating two chambers filled with conductive electrolyte. In the case of solid-state membranes, nanopores are formed via decompositional sputtering using a focused convergent electron beam to form a pore of cross-sectional diameter comparable to the 2.2 nm cross-sectional diameter of double stranded (ds) DNA. Charged molecules (e.g. DNA) are inserted into one of the fluidic chambers, and are electrophoretically driven through the pore under an applied electric potential thereby modulating the ionic current through the pore. The corresponding electronic signature reveals useful information about the structure and dynamic motion of the translocating molecule. This concept can be extended to sequencing in that if each passing nucleotide in ssDNA yields a characteristic residual ionic current, this current trace can then be used to extract sequence information.

Experimental. Nanopore Array Fabrication. Free-standing $Al_2O_3$/SiN membranes are formed using a fabrication process documented previously. The membrane comprises a 350 Å thick $Al_2O_3$ layer deposited via atomic layer deposition (ALD) followed by a capping 430 Å thick SiN layer deposited via plasma enhanced chemical vapor deposition (PECVD). First, ZEP 520 e-beam resist dissolved in Anisole in a ratio of ZEP520:Anisole (2:3) is spun onto the free standing membrane (2000 rpm for 60 s), optimized to a final thickness of 750 Å for ~10 nm feature definition. The ZEP520 coated chips are next baked at 200° C. for 2 minutes, followed by electron beam exposure using a JEOL JBX-6000FS Electron Beam Lithography (dose=10,000 $\mu C/cm^2$). The array patterns are developed in Xylenes for 30 s followed by IPA for 30 s. A reactive ion etching (RIE) step is next used to transfer the array pattern in ZEP520 into the SiN. Etching is done in 60 sccm $CF_4$: 6 sccm $CHF_3$ at a power of 60 W and pressure of 80 mTorr. Etch rates of ~600 Å/min versus ~200 Å/min for ZEP520 are measured under these conditions. The ZEP520 and SiN etch windows serve as the mask for dry etching $Al_2O_3$, done in a PlasmaTherm SLR-770 Inductively Coupled Plasma (ICP) Reactive Ion Etcher. Etching is done in 10 sccm $BCl_3$: 40 sccm Ar at an ICP power of 200 W, platen power of 20 W at a DC Bias ~65V. An $Al_2O_3$ etch rate of ~220 Å/min versus 90 Å/min for SiN and 200 Å/min for ZEP520 is observed under these conditions.

Fabrication of single nanopores in graphene/$Al_2O_3$ membranes. Free-standing $Al_2O_3$/SiN membranes are again formed using the membrane fabrication process documented previously. Large ~300 nm diameter pores are milled in these membranes using a FEI DB235 focused ion beam (FIB) tool. Graphene films are grown using an Etamota chemical vapor deposition (CVD) system, on 1.4 mil copper foils purchased from Basic Copper. The foils are annealed under Ar/$H_2$ flow for 45 minutes and graphene is grown under a $CH_4$/$H_2$/Ar flow at 1000° C., ~500 mTorr for 20 min. The resulting Cu/graphene substrates are cooled to room temperature under Ar flow at a rate of ~20° C./min. Graphene transfer to the receiving substrate proceeds as follows: graphene is coated with a bilayer of PMMA (495K and 950K), backside graphene on the copper foil is removed in an $O_2$ plasma, and then the backside copper is etched in a 1M $FeCl_3$ solution. The resultant PMMA/graphene film is wicked onto a glass slide, rinsed in DI water, rinsed in 10% HCl in DI to remove residual metal particles, followed by a final DI rinse, and wicked onto the receiving substrate. After the graphene dries on the receiving substrate, PMMA is removed in a 1:1 Methylene Chloride:Methanol solution. The transferred film is annealed in a CVD furnace at 400° C. under Ar/$H_2$ flow to remove any residual PMMA. Next, a seed layer, such as a metal seed layer comprising 15 Å of metallic Al is evaporated on the graphene coated chip using a CHA SEC-600 E-Beam Evaporator. This layer completely oxidizes in air and serves as a seed layer for ALD $Al_2O_3$. 60 Å of $Al_2O_3$ is next deposited using ALD. A nanopore is drilled in the graphene/$Al_2O_3$ membrane using a focused convergent electron beam from a JEOL 2010F FEG-TEM with beam conditions similar to that used to drill pores in pure $Al_2O_3$ membranes.

Figure 13:
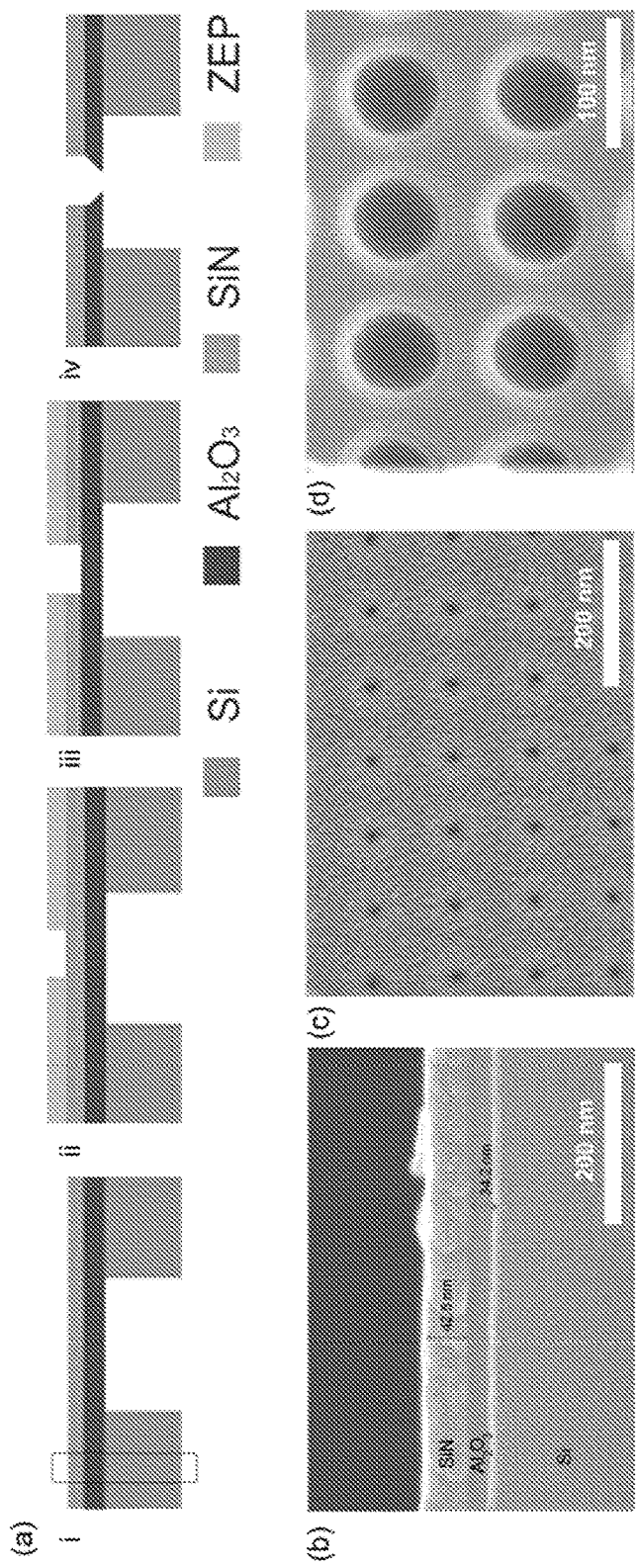
FIG. 13. Nanopore Array Fabrication (a) i Start with suspended $Al_2O_3$/SiN membrane, ii Pattern ZEP520 using e-beam lithography, iii Transfer pattern to SiN using RIE, iv Transfer pattern to $Al_2O_3$ using a $BCl_3$ etch done in an ICP-RIE. (b) SEM cross section of outlined region from (a) part i, showing thicknesses of $Al_2O_3$ and SiN layers. (c) Array of 15 nm diameter pores formed using this process. (d) Array of sub-65 nm diameter pores formed using this process.

Results and Discussion. The nanopore array fabrication process is shown in FIG. 13a. Arrays are formed by first patterning ZEP520 e-beam resist using electron beam lithography and then transferring this pattern into the SiN and $Al_2O_3$ layers using a series of reactive ion etch steps. The optimized process allows the parallel fabrication of ~15 nm diameter nanopores with a pitch of 100 nm as shown in FIG. 13c. Similarly, larger arrays can be fabricated with relative ease as shown in FIG. 13d. ZEP520 electron beam resist is selected for this application due to its high dry etch selectivity relative to PMMA and its ~10× lower electron dose required for clearance, providing rapid wafer scale fabrication of nanopore arrays. Prior to array fabrication in suspended membranes, electron dose is optimized using a series of test exposures on planar substrates to achieve sub-10 nm resolution. The process provided herein facilitates the highly anisotropic dry-etching of sub-20 nm wide features in SiN using a mixture of $CF_4$/$CHF_3$ with an etch selectivity for SiN:ZEP520 of 3:1. $Al_2O_3$ serves as a robust etch stop for this recipe. Pattern transfer into $Al_2O_3$ is achieved using a $BCl_3$:Ar etch recipe with a measured selectivity for $Al_2O_3$: SiN of 2.5:1. A tapered etch profile in $Al_2O_3$ is observed as schematically shown in FIG. 13a (iv) with a cone angle of ~54°, permitting the final pore diameter in $Al_2O_3$ to be significantly less than the patterned pore diameter in ZEP520. This feature is potentially very useful as it may facilitate the fabrication sub-10 nm diameter nanopore arrays in $Al_2O_3$. Integrating nanoscale electrodes into such an architecture to form arrays of individually addressed nanopores allows for high throughput detection of individual DNA molecules for sequencing applications.

Figure 14:
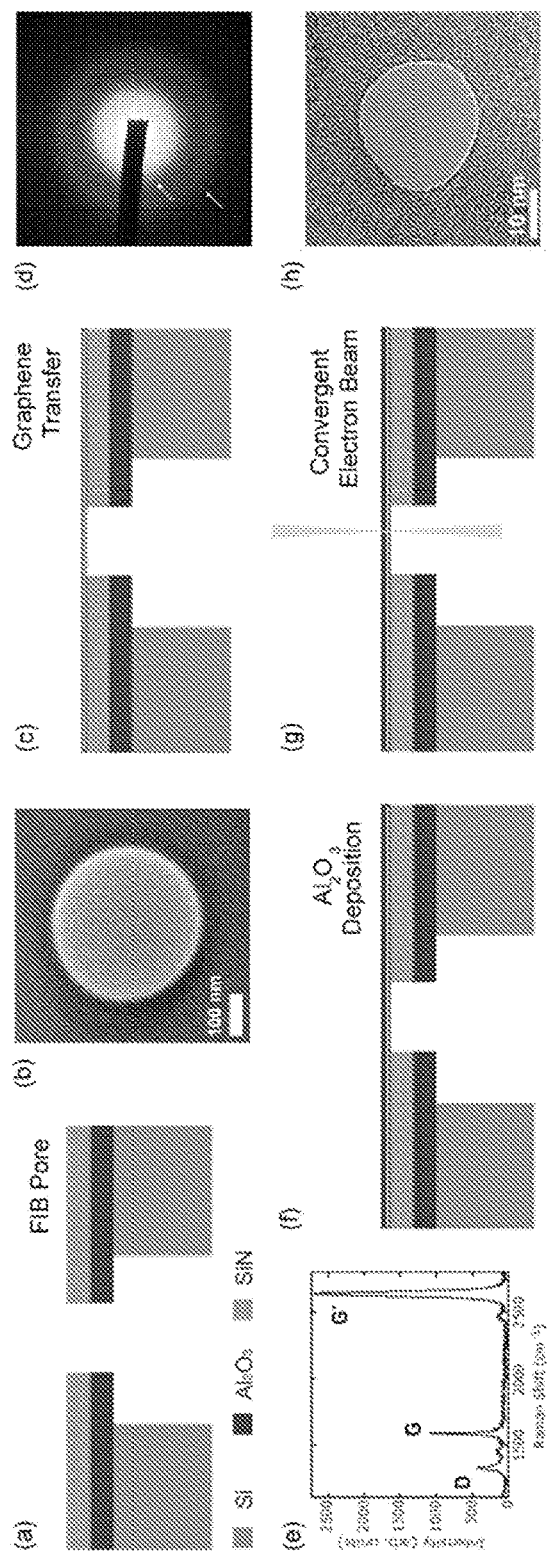
FIG. 14. Fabrication of single nanopores in ultra-thin graphene/$Al_2O_3$ membranes. (a) A ~300 nm diameter FIB pore is first formed as shown by the TEM image of (b). (c) Graphene is next transferred resulting in a suspended monolayer thick membrane confirmed using diffraction imaging (d), and Raman spectroscopy (e). (f) A 15 Å thick Al seed layer is next deposited followed by 60 Å of ALD $Al_2O_3$. (g) A single nanopore is decompositionally sputtered in this suspended membrane using a focused convergent electron beam (h) TEM image of a 25 nm diameter pore formed using this process.

The fabrication of individual nanopores in ultra-thin graphene/$Al_2O_3$ membranes is shown in FIG. 14. A single, ~300 nm pore is first formed in a free-standing SiN/$Al_2O_3$ membrane using a focused ion beam tool. CVD grown graphene is next transferred to the substrate containing the FIB pore as detailed in the experimental section. Following transfer, the integrity of the graphene at both the nano-scale and micro-scale is inspected using TEM diffraction imaging and Raman Spectroscopy. The hexagonal symmetry seen in the diffraction pattern (FIG. 14d) from the graphene membrane spanning the FIB pore suggests likely monolayer graphene, further supported by the peak intensities from the Raman spectrum of FIG. 14e where I(G')/I(G)>2.

The growth of primarily monolayer graphene using the CVD process employed here has been reported. Note the D peak seen in FIG. 14e is characteristic of CVD graphene and results from defects. A 15 Å thick Al seed layer is next evaporated onto the graphene layer followed by ALD deposition of 60 Å of $Al_2O_3$ giving a total membrane thickness of less than 8 nm. A single nanopore is formed in this ultra-thin graphene/$Al_2O_3$ membrane using a focused convergent electron beam as shown in FIGS. 14g and 14h (TEM image). These nanopores are remarkably robust and exhibit linear IV characteristics.

The translocation of protein-DNA complexes through a graphene/$Al_2O_3$ nanopore is shown in FIG. 4. The model DNA-protein system in these studies is ERα bound to a 50 bp long probe containing a single ERE, the cognate binding sequence for the ERα protein. DNA-bound ERα primarily serves as a nucleating factor for the recruitment of protein complexes and is involved in key biological processes including oxidative stress response, DNA repair, and transcription regulation. A schematic showing the binding of ERα to dsDNA containing a single ERE and the ERE sequence itself are shown in FIGS. 4a and 4b respectively. FIG. 4c shows a gel shift assay, ERα/ERE binding being observed exclusively at low salt concentrations. The detection of protein-DNA complexes using a nanopore is analogous to dsDNA detection as shown in FIG. 4d. Notably, the transport of the ERα/ERE complex through a ~14 nm diameter pore in 80 mM KCl results in current enhancements (FIG. 4e), likely due to counter-ion condensation on the complex locally increasing pore conductance during transport as previously reported in DNA transport studies at low salt. A translocation time versus current enhancement scatter plot is shown in FIG. 4f. The most probable translocation time for this 50 bp long DNA probe at 500 mV with a single bound ERαprotein is ~3 ms, two orders of magnitude slower than the estimated translocation time for a 50 bp dsDNA alone. The work presented here confirms that a graphene/Al$_2$O$_3$ nanopore can spatially resolve a single protein bound to dsDNA.

The fabrication of nanopores and nanopore arrays for the sensitive electrical detection of single DNA-protein complexes is demonstrated. The manufacture process allows for the formation of high density arrays of ~15 nm diameter nanopores and greater, fabricated using electron beam lithography and reactive ion etch steps in suspended SiN/Al$_2$O$_3$ membranes. The process may further comprise individually addressing these pores with nano-scale electrodes to facilitate high throughput DNA analysis with application to DNA sequencing. The fabrication of single nanopores in ultra-thin graphene/Al$_2$O$_3$ membranes and the detection of DNA-protein complexes, specifically ERα/ERE, is also demonstrated. Importantly, a spatial resolution of a single protein is achieved using this platform at low salt concentrations.

References

Venkatesan, B. M. & Bashir, R. Nanopore Sensors for Nucleic Acid Analysis. Nat. Nanotechnol., 6:615-624 (Available online Sep. 18, 2011).

Branton, D. et al. The potential and challenges of nanopore sequencing. Nat. Biotechnol. 26, 1146 (2008).

Venkatesan, B. M. et al. Highly Sensitive, Mechanically Stable Nanopore Sensors for DNA Analysis. Adv. Mater. 21, 2771-2776 (2009).

Venkatesan, B. M. et al. Lipid bilayer coated Al$_2$O$_3$ nanopore sensors: towards a hybrid biological solid-state nanopore. Biomed. Microdevices, 1-12 (2011).

Venkatesan, B. M., Shah, A. B., Zuo, J. M. & Bashir, R. DNA Sensing Using Nanocrystalline Surface-Enhanced Al$_2$O$_3$ Nanopore Sensors. Adv. Funct. Mater. 20, 1266-1275 (2010).

Li, X. et al. Large-Area Synthesis of High-Quality and Uniform Graphene Films on Copper Foils. Science 324, 1312-1314 (2009).

EXAMPLE 7

Nanopore Sensors for Nucleic Acid Analysis

Nanopore DNA analysis is an emerging technique that involves electrophoretically driving DNA molecules through a nano-scale pore in solution and monitoring the corresponding change in ionic pore current. This versatile approach permits the label-free, amplification-free analysis of charged polymers (single stranded DNA, double stranded DNA and RNA) ranging in length from single nucleotides to kilobase long genomic DNA fragments with sub-nm resolution. Recent advances in nanopores suggest that this low-cost, highly scalable technology could lend itself to the development of third generation DNA sequencing technologies, promising rapid and reliable sequencing of the human diploid genome for under a $1000. The emerging role of nanopores in sequencing, genomic profiling, epigenetic analysis and medical diagnostics is described in this example.

Sequencing the human genome has helped further understanding of disease, inheritance, and individuality. Genome sequencing has been critical in the identification of Mendelian disorders, genetic risk factors associated with complex human diseases, and continues to play an emerging role in therapeutics and personalized medicine. The growing need for cheaper and faster genome sequencing has prompted the development of new technologies that surpass conventional Sanger chain termination methods in terms of speed and cost. These novel second and third generation sequencing technologies, inspired by the $1000 genome challenge proposed by the National Institute of Health in 2004, are expected to revolutionize genomic medicine. Nanopore DNA sequencing is one such technology that is currently poised to meet this grand challenge.

Nanopore DNA sequencing is attractive as it is a label-free, amplification-free single-molecule approach that can be scaled for high throughput DNA analysis. This technique typically requires low reagent volumes, benefits from relatively low cost and supports long read lengths, potentially enabling de novo sequencing and long-range haplotype mapping. The principle of nanopore sensing is analogous to that of a Coulter counter. A nano-scale aperture or nanopore is formed in an insulating membrane separating two chambers filled with conductive electrolyte. Charged molecules are electrophoretically driven through the pore under an applied electric potential thereby modulating the ionic current through the pore. The corresponding electronic signature reveals useful information about the structure and dynamic motion of the translocating molecule. This concept can be extended to sequencing as first proposed by Deamer, Branton, and Church in the 90's, in that if each passing nucleotide in single stranded DNA (ssDNA) yields a characteristic residual ionic current, this current trace can then be used to extract sequence information.

Recent developments in biological nanopores suggest that nanopore sequencing is indeed feasible. Proof-of-principle experiments using biological α-hemolysin and MspA nanopores have shown significant progress in this direction. This example describes recent advances in this area along with new developments in solid-state and hybrid nanopore technology, in particular the incorporation of graphene that could enable single nucleotide discrimination and ultrafast sequencing. Efforts to slow down DNA translocation (FIG. 15) and novel sensing architectures and modalities that add functionality to the nanopore are also examined (Table 1). The application of these new techniques to sequencing and the associated challenges are briefly presented. Finally, the application of nanopores to areas outside sequencing are discussed, particularly the emerging role of this technology in medical diagnostics.

Ionic current approaches have shown significant success in proof-of-principle sequencing experiments, particularly sequencing by exonuclease digestion and DI sequencing. Nanopore based optical approaches also show promise but require extensive conversion of DNA. Computational studies suggest that transverse electron tunneling and capacitive nanopore approaches may also facilitate ultrafast sequencing, though the experimental realization of these techniques is still pending.

Figure 15:
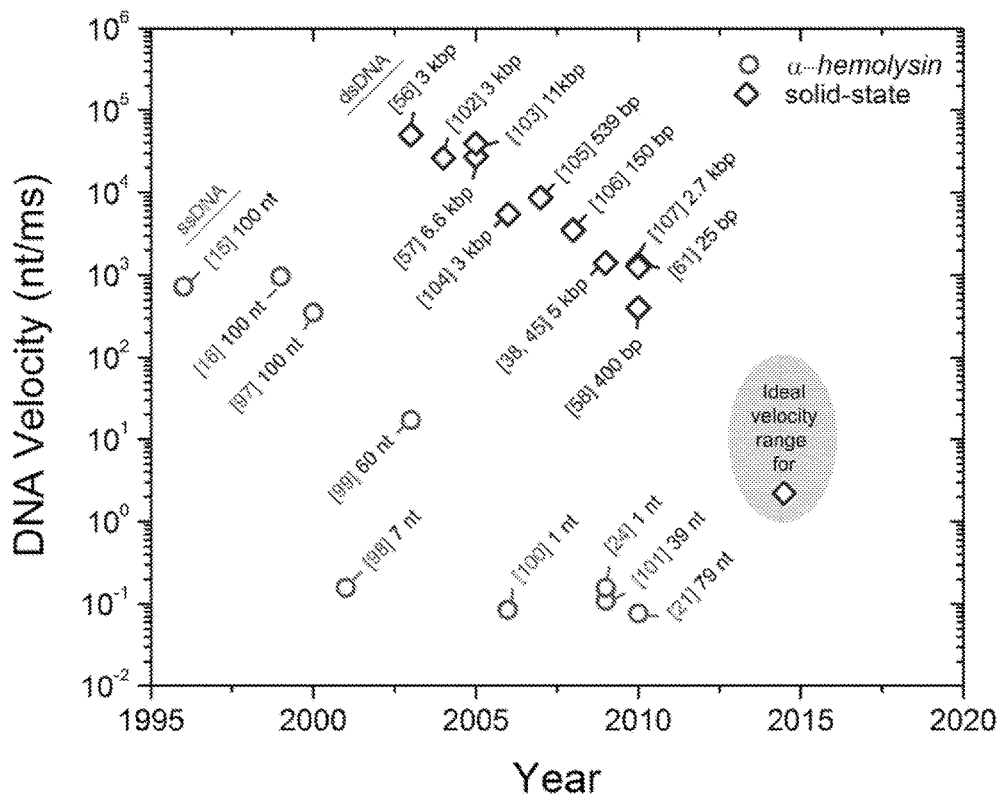
FIG. 15. Trends in Nanopore DNA Analysis. Methods to regulate DNA translocation have resulted in a substantial reduction in DNA translocation velocity each year since the inception of this technology, for both α-hemolysin and solid-state nanopores. Recent advances in biological nanopores have resulted in ssDNA transport speeds as low as ~0.1 nt/ms, and improved sensitivity (down to a single nucleotide), achieved via site specific mutagenesis of native α-hemolysin, the incorporation of DNA processing enzymes, chemically labeling nucleotides, and the covalent attachment of an aminocyclodextrin adapter, enabling DNA sequencing. Similar trends are observed with solid-state nanopores; reductions to translocation velocity and improved sensitivity being accredited to the optimization of solution conditions (temperature, viscosity, pH), chemical functionalization, surface charge engineering, varying the thickness and composition of membranes and the use of smaller diameter nanopores (thereby enhancing polymer-pore interactions). Further reductions to DNA velocity (a velocity of 1-10 nts/ms should be ideal for high resolution DNA analysis) and substantial improvements to sensitivity are needed to enable rapid electronic sequencing of DNA using solid-state nanopores. The development of new sensing modalities and architectures (tunneling junctions, capacitive nanopore structures, graphene gate, etc.) will be of fundamental importance in working towards this goal, though significant challenges are still faced in the development of such technologies (Table 1). This figure contains key nanopore developments that have reported a slowing in DNA transport or enhanced sensitivity, but is by no means an exhaustive list. Each data point in this plot contains the reference number and the shortest molecule detected in the referenced study.
Figure 16:
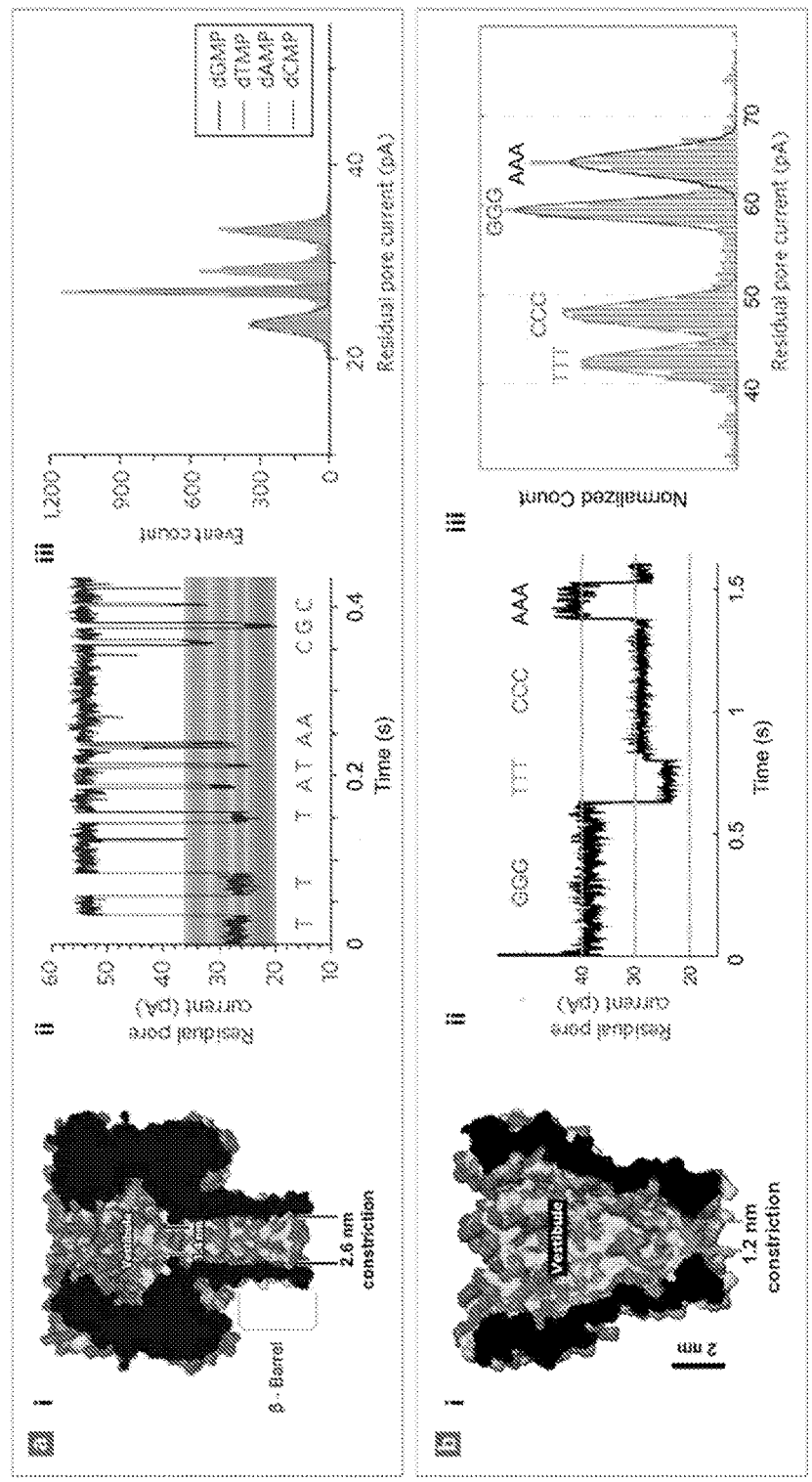
FIG. 16. Biological nanopores for DNA sequencing (a) i. Structural cross-section of α-hemolysin. 1.4 nm constriction permits the passage of ssDNA but not dsDNA ii. Typical current blockade levels induced by individual nucleotides as they traverse an aminocyclodextrin modified α-hemolysin nanopore iii. Nucleotide separation efficiency of α-hemolysin under optimized conditions. Coupled with an exonuclease, a sequencing by digestion approach is presented (b) i. Structural cross-section of MspA ii. Typical current blockades induced by the translocation of duplex interrupted DNA through MspA. A unique current level is observed for each triplet of nucleotides in a duplex interrupted molecule iii. Histogram showing the enhanced separation efficiency of MspA over α-hemolysin.

Biological Nanopores: Biological nanopores reconstituted into lipid bilayers present an attractive option for single molecule DNA analysis. Their versatility can be attributed to several factors: firstly, nature provides the cellular machinery to mass manufacture biological nanopores with an atomic level of precision that still cannot be replicated by the semiconductor industry; X-ray crystallographic information is available revealing pore structure with angstrom level resolution; techniques such as site directed mutagenesis can be used to tailor a pore's physical and chemical properties; and remarkable heterogeneity is observed amongst pores in terms of size and composition. In-vitro studies of DNA transport through biological nanopores have traditionally involved α-hemolysin, the structure of this heptameric protein pore shown in FIG. 16a. The channel is comprised of a 3.6-nm vestibule connected to a transmembrane β-barrel ~5 nm in length, containing a 1.4-nm constriction that permits the passage of single stranded DNA but not double stranded DNA (dsDNA). Kasianowicz first demonstrated the electrophoretic transport of individual ssDNA and ssRNA molecules through α-hemolysin. In particular, early results demonstrated the ability of native α-hemolysin to distinguish between freely translocating RNA homopolymers of cytidylic and adenylic acid, as well as poly(dA) and poly(dC) strands of ssDNA, suggesting the potential emergence of α-hemolysin as a next-generation DNA sequencing tool. The realization of such a tool however has proven challenging, primarily due to the remarkably high velocity with which ssDNA moves through the pore under typical experimental conditions (estimated at ~1 nucleotide/µs) as seen in FIG. 15. At these rapid timescales, as few as ~100 ions are available in the pore to correctly identify a translocating nucleotide, a daunting proposition given thermodynamic fluctuations (statistical variations in the number of charge carriers and position of the nucleotide in the pore) and the subtle chemical differences that exist amongst nucleotides. It has, therefore, proven impossible to sequence freely translocating ssDNA using α-hemolysin.

Most nanopore sequencing strategies to date have sought to actively or passively slow down the transport of ssDNA prior to electronic read-out. Active approaches typically incorporate enzymes to regulate DNA transport through the pore. An enzyme motor coupled to a nanopore is attractive for two reasons: (1) the enzyme-DNA complex forms in bulk solution enabling its electrophoretic capture in the pore and, (2) relatively slow and controlled motion is observed as the enzyme processively steps the DNA substrate through the pore. An elegant demonstration of this is the base-by-base ratcheting of ssDNA through α-hemolysin catalyzed by DNA Polymerase. Single nucleotide primer extension events were electronically observed only in the presence of a complementary nucleotide set, enabling sequencing. More recently, Lieberman et al. demonstrated the processive replication of ssDNA on α-hemolysin using phi29 DNA Polymerase. In addition to being able to resolve individual catalytic cycles, polymerase dynamics could also be discerned (dNTP binding, polymerase fingers opening-closing) using ionic current. A review on the controlled transport of DNA through α-hemolysin using DNA processing enzymes is provided by Deamer. Simpler, passive approaches to slowing down DNA also exist, for example, using nucleotide labeling, end termination of ssDNA with DNA hairpins, incorporating molecular brakes into the pore by lining the transmembrane domain with positively charged residues and so on, but no one approach has emerged in addressing the grand challenge of highly controlled, orientated molecule transport. Nucleotide labeling is quite attractive as the chemistry, charge, and size of the label can be varied potentially enabling "on the fly" sequencing, however labeling contiguous nucleotides in large genomic fragments presents challenges. A more versatile, label-free sequencing method was recently demonstrated by the Bayley group. In this study, Clarke et al. demonstrated the ability to continuously resolve indigenous mononucleotides (dAMP, dCMP, dGMP, dTMP) through α-hemolysin using resistive current measurements. Base selectivity was achieved by modifying a mutant α-hemolysin pore with an aminocyclodextrin adapter covalently bound within the β barrel of the transmembrane domain, thereby constricting the channel while enhancing the chemical specificity of the sensor. Raw mononucleotides were read with over 99% confidence under optimal operating conditions. By integrating this base identification platform with a highly processive exonuclease through either chemical attachment or genetic fusion, a nanopore based single molecule sequencing by digestion approach may indeed be feasible. Such an approach forms the basis for commercial sequencing efforts by Oxford Nanopore (Oxford, UK).

Although α-hemolysin has by far dominated the biological nanopore sequencing landscape in the past, more efficient biological nanopores for sequencing have already begun to emerge. A structural drawback with α-hemolysin pertains to its ~5 nm long cylindrical β barrel that accommodates up to ~10 nucleotides at a time. Nucleotides located in this β barrel significantly modulate the pore current and subsequently dilute the ionic signature specific to a single nucleotide in the narrowest 1.4 nm pore constriction, reducing the overall signal-to-noise ratio in sequencing applications. This inherent structural limitation is overcome by a relatively new candidate in the nanopore sequencing arena, the channel porin *Mycobacterium smegmatis* porin A (MspA). MspA is an octameric protein channel that contains a single constriction of diameter ~1.2 nm with a channel length of ~0.5 nm, forming a tapered funnel shape (structural cross section shown in FIG. 16b), as opposed to the cylindrical structure of α-hemolysin. Derrington et al. demonstrated the ability of genetically engineered MspA to discriminate between tri-nucleotide sets (AAA, GGG, TTT, CCC) with an impressive 3.5 fold enhancement in nucleotide separation efficiency over native α-hemolysin. Interestingly, in experiments involving immobilized ssDNA, as few as three nucleotides within or near the constriction of MspA were seen to contribute to the pore current, a significant improvement over the ~10 nucleotides known to modulate ionic current in native α-hemolysin. The authors hypothesize that this could be further improved to perhaps a single nucleotide through site specific mutagenesis, an obvious goal of future MspA mutants. The application of MspA to de novo sequencing is not without challenges either. The speed of unimpeded ssDNA translocation through MspA still remains too fast to sequence ssDNA 'on the fly'. To overcome this limitation, duplex interrupted (DI) nanopore sequencing was recently proposed. DI sequencing involves the insertion of a 'short' double-stranded DNA segment between each nucleotide in an analyte DNA molecule. As duplex converted DNA is driven through an MspA nanopore, each duplex sequentially halts the translocation process, exposing a single analyte nucleotide to the confining nanopore aperture for identification using ionic current.

Upon duplex dissociation, the DNA advances until the next duplex where the next analyte nucleotide is determined and so forth. Such a method could ultimately enable fast and long sequential reads; however, the ability to convert and read large genomic fragments with high fidelity using this approach still remains to be seen. An alternative approach to DI sequencing is to couple an enzyme-motor to MspA to controllably step ssDNA through the pore with nucleotide identification occurring at each step, a method referred to as strand sequencing. Candidate enzymes suited for this application include T7 DNA Polymerase, Klenow fragment of DNA Polymerase 1 and phi29 DNA polymerase, the latter known to be remarkably stable and highly efficient at catalyzing sequential nucleotide additions at the α-hemolysin orifice under a high 180 mV applied load. It is plausible therefore that phi29 DNA polymerase coupled to MspA could enable the sequencing of long strands of DNA, though the experimental realization of such a system has not yet been demonstrated.

The application of biological nanopores to areas outside DNA sequencing also holds tremendous potential. One particular biological pore that could find useful applications in molecular diagnostics and DNA fingerprinting is the connector protein from the bacteriophage phi29 DNA packaging motor. The versatility of this protein nanopore stems from its relative size, the protein hub being comprised of twelve GP10 subunits that self-assemble to form a channel of inner diameter ~3.6 nm. Interestingly, the open channel conductance of this nanopore is ~5 times higher than that of α-hemolysin under similar conditions, suggesting the possibility of screening larger analytes including dsDNA, DNA protein complexes and amino acid polymers for protein sequencing. The translocation of dsDNA through a genetically engineered connector channel embedded in a lipid bilayer was recently demonstrated by Wendell et al. Unidirectional transport of dsDNA through this channel (from N-terminal entrance to C-terminal exit) was observed, suggesting a natural valve mechanism in the channel that assists dsDNA packaging during bacteriophage phi29 virus maturation. The capabilities of this exciting protein nanopore will become more apparent in years to come.

Solid-State Nanopores. Despite the heterogeneity and remarkable sensitivity of biological nanopores, these sensors do exhibit some inherent disadvantages. The delicate nature of the mechanically supporting lipid bilayer, the sensitivity of biological pores to experimental conditions (pH, temperature, salt concentration), and challenges associated with large scale array integration for high throughput DNA analysis/sequencing limit the versatility of these biological platforms. Even with ongoing improvements to bilayer stability through the development of supported bilayers on solid and nanoporous substrates, varying bilayer lipid compositions, and the development of tethered bilayer architectures, the robustness and durability of solid-state membranes still significantly supersedes that of their biological counterparts. Coupled with advances in microfabrication techniques, solid-state nanopores are therefore fast becoming an inexpensive and highly versatile alternative to biological nanopores. Other advantages afforded by solid-state technology include the ability to tune nanopore dimensions with sub-nm precision, the ability to fabricate high density nanopore arrays, superior mechanical, chemical, and thermal characteristics over lipid-based systems and the possible integration with electrical and optical probing techniques.

The first reports of DNA sensing using solid-state nanopores emerged from the Golovchenko lab in early 2001. Nanopores were formed in thin SiN membranes using a custom built feedback controlled ion beam sculpting tool, a process that yields true nanometer control over pore size. Today, most groups prefer to use a focused convergent electron beam from a field emission gun (FEG) TEM to decompositionally sputter nanopores in thin insulating membranes, a technique that has evolved since the 1980s. The fabrication of solid-state nanopores in thin insulating membranes is reviewed by Healy et al. and the application of this technology to single molecule biophysics is reviewed by Dekker. SiN has traditionally been the nanopore membrane material of choice due to its high chemical resistance and low mechanical stress, deposited via an optimized low pressure chemical vapor deposition process. This process is typically done at elevated temperature (~800° C.) and lacks thickness control in the sub-nm regime. To effectively probe the local structure of DNA with the resolution of an individual nucleotide, insulating membranes of sub-nm thickness are required. In working towards this goal, a method of forming nanopores in ultra-thin insulating $Al_2O_3$ membranes using atomic layer deposition (ALD) is proposed, a process that yields angstrom level control over membrane thickness. The fabrication of nanopores in $Al_2O_3$ membranes using a focused electron beam revealed two interesting phenomena, the dose-dependent conversion of $Al_2O_3$ to metallic Al, applicable to the direct 'write' of nanoscale electrodes in the pore, and the controlled formation of α and γ nanocrystalline domains, permitting nano-scale surface charge engineering at the pore/fluid interface. Controlling the stoichiometry of the material in the pore and surface charge density is important given the impact of these parameters on 1/f noise and DNA transport velocities. Interestingly, slower DNA transport was observed in $Al_2O_3$ nanopores relative to SiN pores of similar diameter, attributed to strong electrostatic interactions between the positively charged $Al_2O_3$ surface and negatively charged dsDNA. Enhancing these interactions, either electrostatically or chemically, could further help reduce DNA transport velocities, a prerequisite for nanopore sequencing. The versatility of this ALD based technique also allows for: 1) the formation of membranes and nanopores in a variety of other high-k dielectric materials including $TiO_2$ and $HfO_2$, each with unique material properties and 2) the integration of metallic contacts and graphene layers directly into the membrane due to the low temperature nature of the ALD process (typically <250° C.). Though this approach has shown much promise, the fabrication of robust, insulating ALD membranes of sub-nm thickness has proven challenging due to ionic current leakage through pinholes in ultrathin films. The formation of sub-nm thick insulating membranes will therefore likely require a novel approach.

Figure 17:
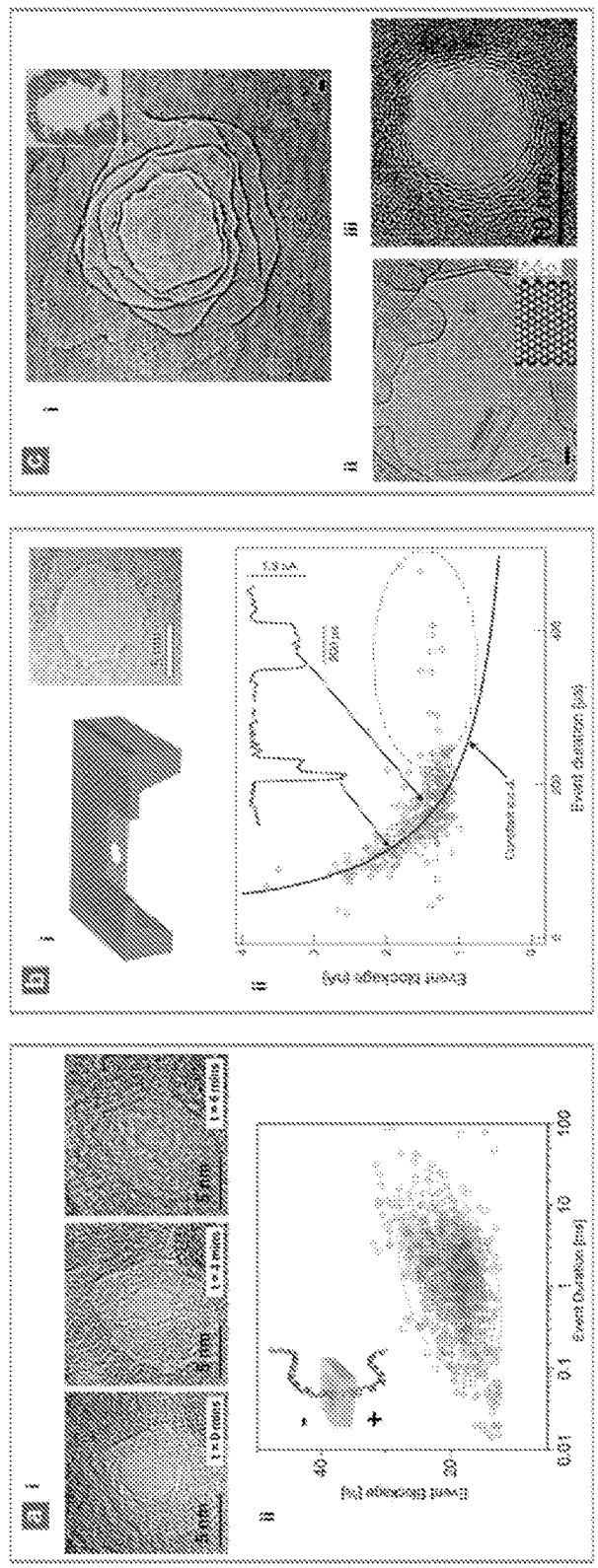
FIG. 17. Solid-state nanopore architectures for DNA analysis (a) $Al_2O_3$ nanopores i. Formation and controlled contraction of nanopores in ALD $Al_2O_3$ membranes using a focused electron beam. Sub-nm precision is achievable. ii. Scatter plot of 5 kbp dsDNA tranlocation through a 5 nm diameter $Al_2O_3$ pore showing a single blockage level corresponding to linear, unfolded dsDNA transport (b) Graphene nanopores i. TEM based formation of nanopores in 1-2 monolayers of graphene ii. Scatter plot shows unique conductance signatures that are representative of different DNA conformations translocating through the pore (folded and unfolded DNA) (c) i. TEM image of a terraced nanopore formed in ~10 monolayers of graphene, ii. Nanopore in a monolayer of graphene with primarily arm-chair edges surrounded by multilayered regions, iii. TEM image of a nanopore in multilayer graphene; ripples at the pore edge again show the terraced structure.
Figure 18:
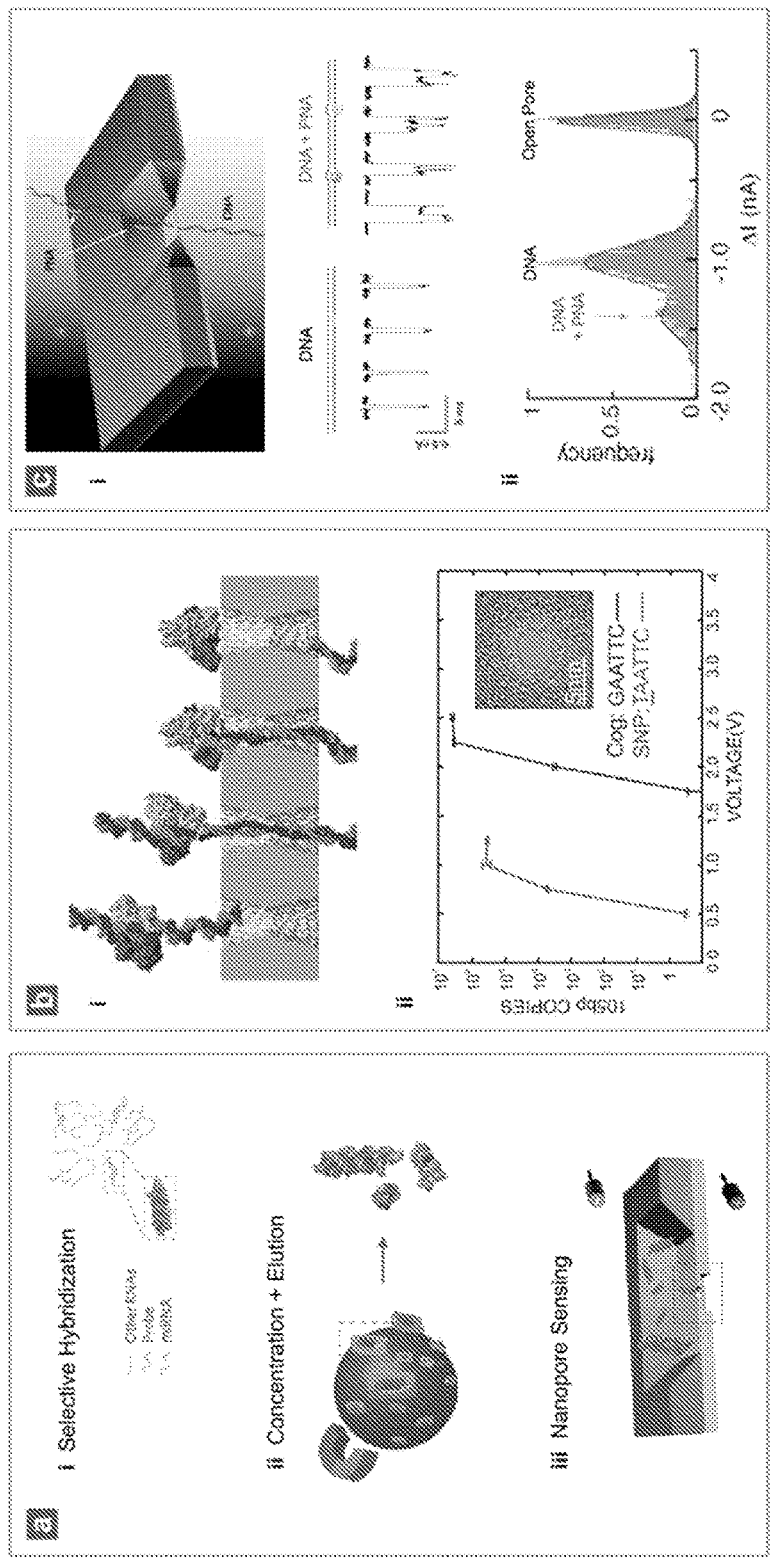
FIG. 18. Nanopore applications outside sequencing (a) Detection of sequence specific miRNAs from tissue: Probe specific hybridization used to separate and concentrate specific miRNAs from tissue samples followed by nanopore based quantification. This technique offers enhanced sensitivity over conventional microarray techniques (b) Detection of SNPs: Protein (EcoR1) bound dsDNA complexes were electrophoretically driven to a ~2 nm diameter nanopore and then sheared as shown in i. The introduction of a SNP into the protein binding sequence resulted in detectable shifts in the shearing threshold voltage as confirmed by quantitative PCR (ii), thereby allowing for the sensitive detection of SNPs (c) Genotyping and genomic profiling: PNA tagged dsDNA products produced unique current transients in nanopore measurements as shown in i. The number of PNA tags per molecule can be easily quantified, facilitating rapid electrical profiling of DNA molecules.

Graphene: Graphene, an atomically thin sheet of carbon atoms densely packed into a two-dimensional honeycomb lattice possesses remarkable mechanical, electrical and thermal properties. The comparable thickness of a graphene monolayer to the 0.32-0.52 nm spacing between nucleotides in ssDNA, makes this material particularly attractive for electronic DNA sequencing. The first reports of single nanopores and nanopore arrays fabricated in suspended graphene films emerged from the Drndic lab in 2008. Subsequent TEM based studies by the Zettl group elucidated both the kinetics of pore formation in graphene and graphene edge stability (zig-zag versus armchair) in-situ. The detection of individual dsDNA molecules using graphene nanopores however, has only been recently demonstrated. In separate studies, the Golovchenko (Harvard), Dekker (Delft), and Drndic (University of Pennsylvania) labs reported the electron-beam based fabrication of 5-25 nm diameter nanopores in suspended graphene films, prepared through either chemical vapor deposition (CVD) or exfoliation from graphite. Nanopores were formed in as few as 1-2 monolayers of graphene with membranes exhibiting remarkable durability and insulating properties in high ionic strength solution. The conductance of pores in monolayer thin membranes exhibited some unique trends. The Harvard study showed a linear scaling of pore conductance with pore diameter, $d_{pore}$, in monolayer thin membranes as opposed to the $d_{pore}^2$ scaling typically observed with pores in thick SiN membranes. An effective membrane thickness, $h_{eff}$, of ~0.6 nm was extracted for nanopores formed in a graphene monolayer. This result agrees with the theory in the limit as $h_{eff} \rightarrow 0$ where the dominant resistance is not the pore resistance itself ($R_{pore}$) but rather the access resistance ($R_{access}$ attributed to the potential drop in the electrolyte from the electrode to the nanopore), where $R_{access}$ scales inversely with $d_{pore}$. In contrast, the Delft studies showed that the conductance of nanopores in a graphene monolayer scales as a function of $d_{pore}^2$, an intriguing result that suggests a cylindrical nanopore geometry of non-negligible thickness ($R_{pore} > R_{access}$). The origin of this $d_{pore}^2$ scaling may be due to a polymer coating (6-mercaptohexanoic acid) introduced on the graphene to reduce DNA adsorption. Furthermore, the Delft group reported similar conductance values for equidiameter pores formed in a single monolayer versus pores formed in membranes of thickness up to 8 monolayers. The latter result is plausible as nanopore formation in multilayer graphene is known to induce a terrace effect where the number of graphene layers monotonically decreases radially in the direction of the pore center, with regions of only monolayer thickness lining the pore edge (FIG. 17c). This effect was confirmed recently using TEM image analysis and is also visible in earlier studies. A terraced nanopore architecture could prove very useful for two reasons: 1) it potentially relaxes the constraint of growing and transferring a large area monolayer in order to fabricate a graphene monolayer nanopore and 2) a multilayered support may increase the stability and longevity of a graphene nanopore sensor.

The translocation of dsDNA through graphene pores induced subtle fluctuations in the ionic current marking the transport of both folded and unfolded DNA structures, analogous to DNA induced current blockades in SiN nanopores. Translocation velocities ranged anywhere from 10-100 nts/μs, too fast for the electronic measurement of individual nucleotides. As a result, Garaj probed the theoretical spatial and geometric resolution of a graphene monolayer nanopore using computational analysis. Pseudo-static simulations of dsDNA in a 2.4-nm diameter graphene pore of thickness ~0.6 nm revealed a resolution of ~0.35 nm, identical to the size of an individual DNA nucleotide. This exciting result suggests that if DNA translocation could be sufficiently slowed in a graphene pore to say ~1 nt/ms, single nucleotide detection is theoretically possible potentially facilitating electronic sequencing. To enable such advancements however, the quantitative aspects of DNA transport need to be better understood. For example, it still remains to be seen why under normalized conditions (salt concentration, voltage), nanopores in multilayer graphene (3-15 monolayers) give deeper DNA induced current blockades relative to pores in single layer graphene. One possible explanation is the terrace effect previously mentioned, though more detailed studies on graphene nanopore structure, properties and quantitative DNA transport are needed. A number of fundamental questions pertaining to sequencing also remain. For example, it is not clear whether single nucleotide resolution is experimentally realizable in the presence of thermodynamic fluctuations and electrical noise. Furthermore, the chemical and structural similarity amongst purines and pyrimidines could inherently limit the identification of individual nucleotides using ionic current alone through a bare graphene pore. Surface functionalization of graphene pores may be necessary to enhance nucleotide specificity, though such an approach may compromise resolution due to membrane thickening.

Figure 19:
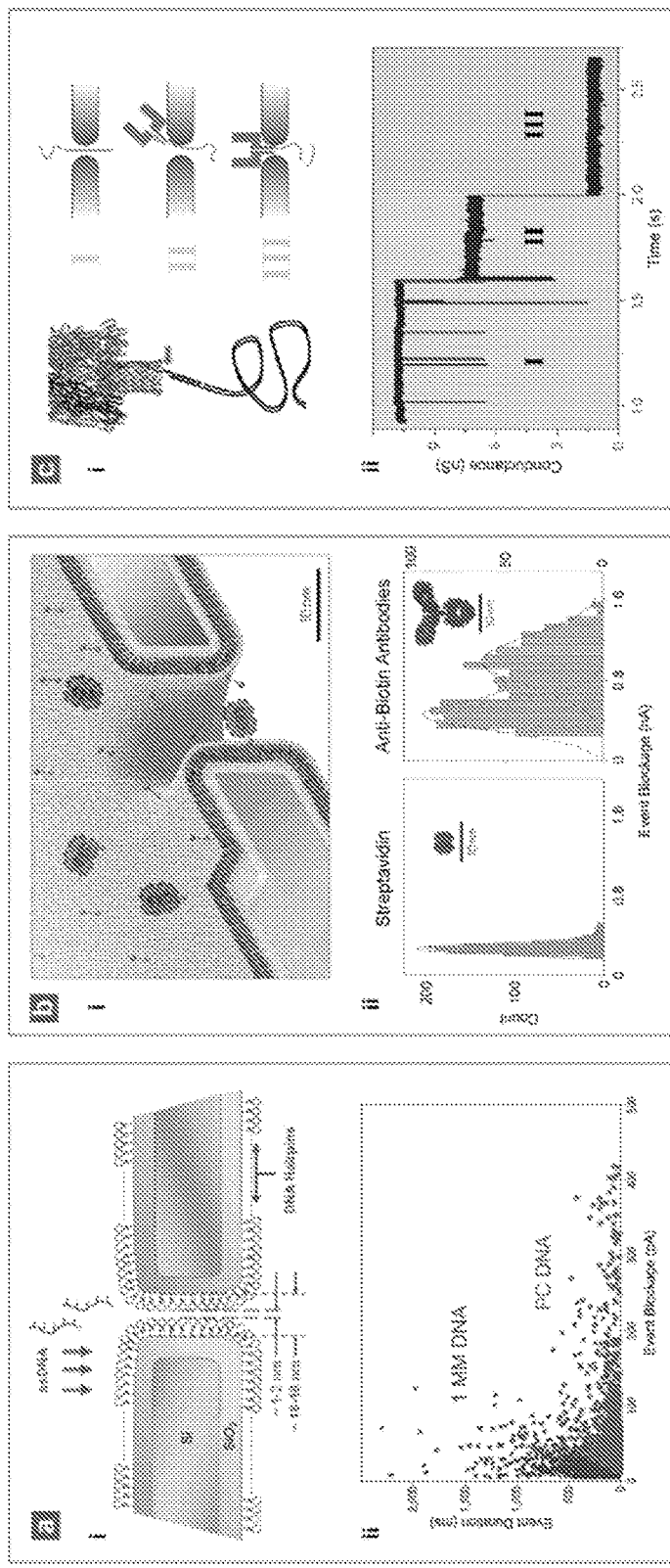
FIG. 19. Hybrid Biological Solid-State Nanopores (a) Hairpin DNA functionalized $SiO_2$ nanopores ii. The translocation of perfect complementary ssDNA (complementary to the hairpin sequence) versus a single base mis-match sequence (1 MM) resulted in a bimodal distribution as shown, thereby allowing for the sensitive detection of SNPs (b) Lipid bilayer coated SiN nanopores with fluid lipid side walls function as highly sensitive protein detection elements ii. Current blockage histograms could be used to detect and differentiate various protein analytes using this surface functionalized nanopore (c) Direct insertion of α-hemolysin into a SiN pore i. Schematic of α-hemolysin chemically modified with a dsDNA tail ii. The three stages of hybrid pore formation are shown, finally resulting in a conductance level (III) consistent with α-hemolysin in a lipid bilayer.

Nanopore applications outside DNA sequencing. The more immediate application for solid-state nanopores is likely in medical diagnostics. A nanopore based diagnostic tool could: (1) detect target molecules at very low concentrations from minute sample volumes (perhaps shed DNA from tumor cells in patient serum); (2) simultaneously screen panels of biomarkers/genes (important in diagnosis, monitoring progression and prognosis); (3) provide rapid analysis at relatively low cost; and (4) eliminate cumbersome amplification and conversion steps such as PCR, bisulfite conversion, and Sanger sequencing. MicroRNA (miRNA) expression profiling is one application where solid-state nanopore technology could excel. The detection and accurate quantification of these cancer biomarkers will likely have important clinical implications, facilitating disease diagnosis, staging, progression, prognosis, and treatment response. Wanunu et al. recently demonstrated a nanopore based approach for the detection of specific microRNA sequences enriched from cellular tissue with sensitivities surpassing conventional micro-array technologies (FIG. 19a). Another exciting prospect is the use of solid-state nanopores for epigenetic analysis, more specifically the detection of aberrant DNA methylation, an early and frequently observed event in carcinogenesis. Hypo- and hypermethylation in the promoter sequences of specific genes serve as both robust cancer biomarkers (e.g. GSTP1 promoter hypermethylation observed in over 90% of prostate cancer cases), as well as indicators of disease severity and metastatic potential in many tumor types. Preliminary progress towards nanopore based methylation analysis has been demonstrated by the Timp and Drndic labs involving the detection of methylated and hydroxymethylated DNA.

Genetic analysis involving the detection of single nucleotide polymorphisms (SNPs) is another important diagnostic application tailored for nanopores. SNPs and point mutations have been linked to a variety of Mendelian diseases such as cystic fibrosis and Huntington's disease as well as more complex disease phenotypes. In proof-of-principle experiments, Zhao and coworkers demonstrated the sensitive detection of SNPs using ~2 nm diameter SiN nanopores. Using the nanopore as a local force actuator, the binding energies of a DNA binding protein and its cognate sequence relative to a SNP sequence could be discriminated (FIG. 19b). This approach could be extended to screen mutations in the cognate sequences of various other DNA binding proteins, including transcription factors, nucleases and histones. The Meller lab, using solid-state nanopores, is actively pursuing another direction; the rapid genotyping of viruses and human pathogens. An innovative approach involving the introduction of highly invasive Peptide Nucleic Acid (PNA) probes was used to label target genomes with high affinity and sequence specificity, creating local bulges (P-loops) in the molecule. Translocation of this labeled molecule resulted in secondary DNA-PNA blockade levels (FIG. 19c), effectively barcoding a target genome. While further studies are needed to determine the ultimate spatial resolution of this technique, this methodology could potentially enable the rapid, accurate and amplification free, identification of small 5-10 kb viral genomes including Hepatitis C, Dengue and West Nile Virus.

Hybrid Biological/Solid-State Nanopores. A major drawback with solid-state nanopore technology at present is the inability to chemically differentiate analytes of the same approximate size. This lack of chemical specificity can be overcome through surface modification of the pore via the attachment of specific recognition sequences and receptors, in essence forming a hybrid structure. A chemically sensitive nanopore may be necessary to uniquely identify nucleotides in sequencing applications or to differentiate and quantify target proteins in diagnostic applications. Chemical functionalization and its effect on the electrical properties of polymer nanopores was recently demonstrated by Siwy. Surface functionalization can also be used to introduce DNA sequence specificity. In studies involving DNA hairpin functionalized $SiO_2$ nanopores, higher flux and smaller translocation times were observed for the passage of perfect complementary (PC) ssDNA versus single base mismatched probes (1 MM), a highly sensitive strategy for the detection of SNPs (FIG. 19a). Functionalized biomimetic nanopores in SiN have furthermore enabled the study of nucleocytoplasmic transport phenomena at the single-molecule level. Altering the surface chemistry of a pore can also facilitate the sensitive detection and discrimination of proteins. Drawing inspiration from the lipid coated olfactory sensilla of insect antennae, the Mayer lab recently demonstrated the identification of proteins using fluid lipid bilayer coated SiN nanopores (FIG. 19b). The incorporation of mobile ligands into the bilayer introduced chemical specificity into the pore, slowed the translocation of target proteins, prevented pores from clogging and eliminated non-specific binding, thereby resolving many issues inherent to solid-state nanopores. A lipid bilayer coated nanopore architecture of this nature (in either SiN or $Al_2O_3$) also allows for future integration with biological nanopores to form robust nanopore sequencing elements.

The concept of a hybrid biological solid-state nanopore was recently advanced by Dekker and co-workers, through the direct insertion of genetically engineered α-hemolysin into 2.4-3.6 nm diameter SiN nanopores. A simple yet elegant strategy was devised to control the orientation of α-hemolysin in the solid-state pore. By chemically linking a long dsDNA tail to the protein pore as shown in FIG. 19c, the entry of this engineered α-hemolysin channel into a SiN nanopore could be electrophoretically guided to form a coaxially aligned structure. Hybrid pore conductance and ssDNA translocation event durations were in good agreement with α-hemolysin embedded in lipid bilayers. Interestingly, ssDNA blockade amplitudes through hybrid pores were significantly less than in α-hemolysin-bilayer systems, attributed to both deformation of the biological pore, and leakage currents around its body when inserted into a solid-state pore. Also, an increase in electrical noise was observed in hybrid structures. These parameters will likely need to be optimized in order to match the single nucleotide sensitivity of aminocyclodextrin modified α-hemolysin. Nevertheless, this hybrid architecture opens up the exciting possibility of high throughput sequencing by coupling the single nucleotide recognition capabilities of either α-hemolysin or MspA, with wafer-scale arrays of individually addressed solid-state nanopores.

The advances described here suggest that nanopores will likely play an increasing role in medical diagnostics and DNA sequencing in years to come. As new optical and electronic approaches for the detection and sequencing of DNA molecules emerge, including single molecule evanescent field detection of sequencing-by-synthesis in arrays of nano-chambers (Pacific Biosciences), sequencing by ligation on self-assembled DNA nanoarrays (Complete Genomics), and the detection of $H^+$ ions released during sequencing-by-synthesis on silicon field effect transistors from multiple polymerase-template reactions (Ion Torrent), the goal of direct read 'on the fly' sequencing of a single molecule using a biological or solid-state nanopore still remains a highly attractive grand challenge. The exciting possibility of performing long base reads on unlabeled ssDNA molecules in a rapid and cost-effective manner could revolutionize genomics and personalized medicine. This fascinating prospect continues to drive innovation in both academic and commercial settings, including large scale investment from the NIH and private sector investment from companies including Roche/IBM, Oxford Nanopore, and NABsys. Current trends suggest that significant hurdles inhibiting the use of biological nanopores in sequencing (high translocation velocity, a lack of nucleotide specificity) have been resolved. Similarly, if DNA translocation through solid-state nanopores could be slowed down to ~3 Å/ms (length of a single nucleotide moving in a millisecond through a sensor region with spatial resolution of ~3 Å), and if nucleotides could be identified uniquely with an electronic signature, a 1 million base long molecule could be sequenced in less than 20 minutes. Scaling this technology to an array of 100,000 individually addressed nanopores operating in parallel could enable the sequencing of a 3 billion by human genome with 50 fold coverage in less than 1 hour.

Figure 20:
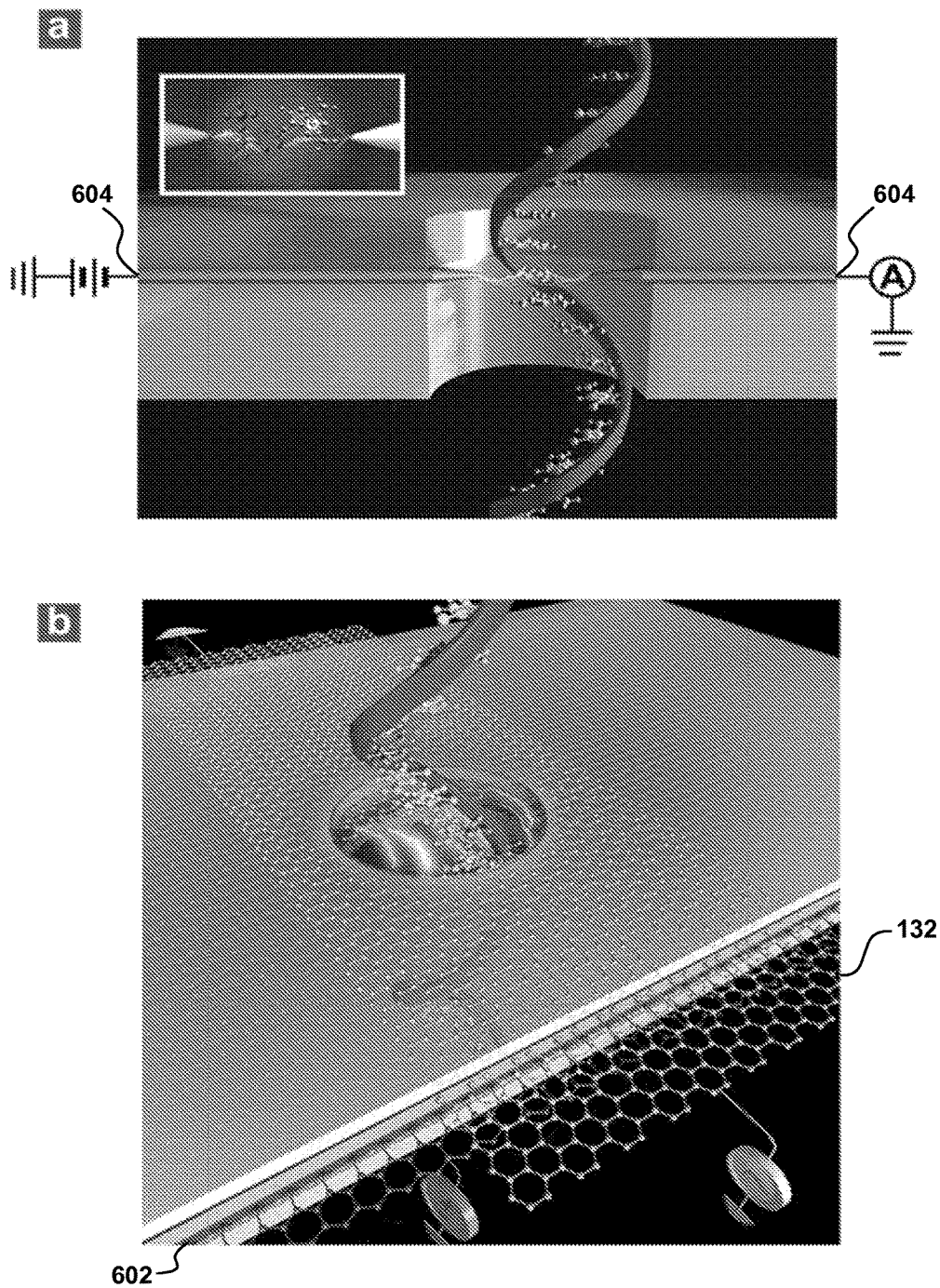
FIG. 20. Possible novel nanopore architectures for sequencing. (a) Cross section of a tunneling detector embedded in a nanopore. The detector comprises two electrodes spaced ~1 nm apart with the pore in the middle. The nanopore facilitates the linear passage of ssDNA/nucleotides past the detector and the detector is used to decode sequence information by measuring nucleotide specific tunneling currents (Inset) Top view of the tunneling electrodes with a nucleotide positioned in the nanogap. (b) A graphene nanoribbon on a solid-state nanopore with an embedded graphene gate. The graphene gate is used to achieve either p-type or n-type behavior for sufficiently small ribbons and to electrostatically slow down ssDNA. The graphene ribbon may act as the nucleotide reader with each nucleotide uniquely modulating its transverse conductance. The functionalization of graphene ribbon edges in the nanopore can further enhance nucleotide specific interactions.

To achieve this, novel architectures that add functionality at the nanopore interface are likely needed, such as the electronically gated nanopores and nanochannels provided herein, the integration of single-walled carbon nanotubes, and graphene nanoribbons and nanogaps embedded in a nanopore. IBM's approach to sequencing using a DNA nanopore transistor architecture is equally intriguing. Using molecular dynamics, the IBM group demonstrated the controlled base-by-base ratcheting of ssDNA through a nanopore formed in a multilayered metal-oxide membrane using alternating electric fields applied across the metal layers. An experimental demonstration of this result has not yet been shown however. Recent experimental advances using scanning tunneling microscopy are also exciting and suggest the possibility of identifying nucleotides using electron tunneling (nucleotide specific tunneling currents being associated with differences in the HOMO-LUMO gaps of A, C, G, T) and the partial sequencing of DNA oligomers. The use of nanofabricated metallic gap junctions to measure nucleotide specific electron tunneling currents is particularly fascinating in that if a tunneling detector of this nature could be embedded in a nanopore and DNA could be sufficiently slowed, the goal of solid-state nanopore sequencing may be attainable. Exemplary nanopore architectures for sequencing are shown in FIG. 20, with electrical contacts 604 to the embedded graphene layer to measure transverse current via the electrically connected power source and detector (FIG. 20a). FIG. 20b illustrates a nanoribbon graphene layer 132 and an embedded gate electrode 602 that is an embedded graphene layer.

Efforts to fabricate nanogap-nanopore tunneling detectors are currently underway, though the path to sequencing is not trivial given thermal fluctuations of bases within the nanopore (whether individual nucleotides or contiguous nucleotides in ssDNA) and electrical noise. Hence a statistical approach involving many repeat sampling events of each nucleotides/molecule will likely be needed to obtain sequence information. Additionally, as tunneling currents are exponentially dependent on barrier widths and heights (based on the effective tunnel distance and molecule orientation), a two point measurement might inherently provide only limited information. Perhaps a measurement setup analogous to a 4 point probe is needed, however, reliably fabricating such a structure with sub-nm precision is still a formidable task. It should also be noted that for certain applications, all 4 bases might not need to be uniquely identified. Investigators have been using binary conversion of nucleotide sequences (A/T=0, and G/C=1), to successfully map short DNA and RNA fragments to the genome for marker discovery and identification of genomic alterations. Hence, even the direct sequencing with binary identification of nucleotide pairs in dsDNA using nanopores could be of significant prognostic and diagnostic value.

In summary, significant advances have been made over the past few years in both biological and solid-state nanopores for label-free 'on the fly' sequencing of DNA molecules. There is no doubt that nanopores will stay as an important enabler of generation three sequencing technologies in the race towards affordable and personalized DNA sequencing.

Figure 21A:
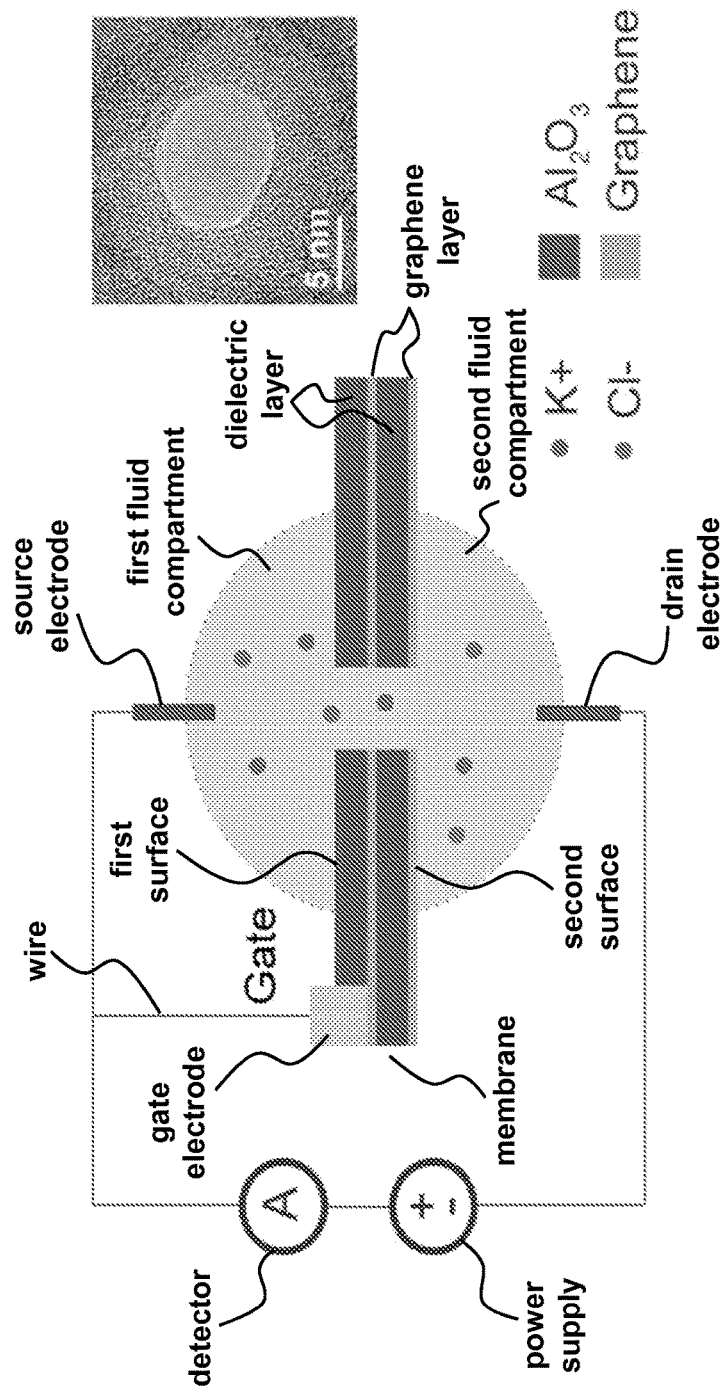
FIG. 21A is a schematic of one embodiment of membrane and related components for characterizing a biomolecule.
Figure 21B:
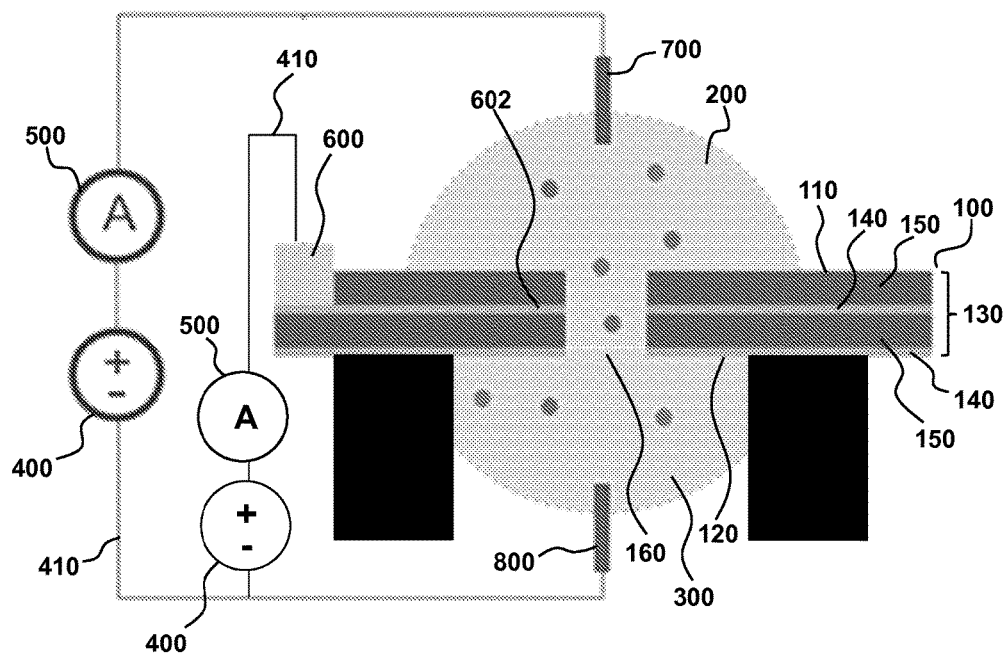
FIG. 21B is similar to the FIG. 21A, also having a bias at the gate electrode.
Figure 22:
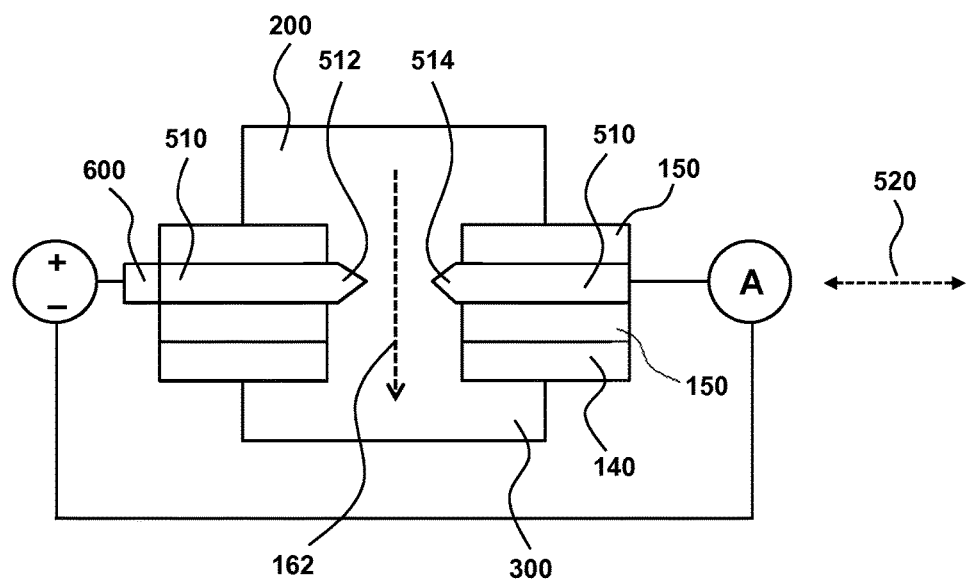
FIG. 22 is a schematic close-up of a tunneling detector comprising a pair of electrodes facing each other in a direction transverse to a biomolecule that transits the nanopore in a direction indicated by the dashed arrow. In this configuration the device may be characterized as a nucleotide reader.

Exemplary embodiments of certain devices and methods are provided in FIG. 21A, 21B and 22. Referring to FIG. 21B, membrane 100 comprises a stack 130 formed by a plurality of graphene layers 140 separated from each other by dielectric layers 150. A first surface 110 forms one surface of first fluid compartment 200 and a second surface 120 forms one surface of second fluid compartment 300. Nanopore 160 fluidically connects first and second fluid compartments 200 and 300 through membrane 100. Power supplies 400 and detectors 500 are used to energize the system and to measure an electrical parameter in the nanopore, including independently with embedded gate electrode 602 connected to a power supply and detector via gate electrode 600. Source 700 and drain 800 electrodes may bias the first and second fluid compartments relative to each other. Electrically conductive wire 410 may connect the various electrical components.

Referring to FIG. 22, a tunneling detector 510 is formed by a pair of electrodes 512 and 514 that face each other in the nanopore and oriented in a direction 520 that is transverse or orthogonal to the nanopore axial direction 162, as indicated by the dashed arrows. In an aspect, the pair of electrodes 512 and 514 are formed from a graphene layer 140. Gate electrode 600, such as Ti/Au pad, is connected to the tunneling detector to provide electrical contact to the tunneling detector corresponding to embedded graphene layer that is electrically isolated from the other layers. In this manner, a biomolecule interacting or transiting nanopore from first fluid compartment 200 to second fluid compartment 300 is characterized via monitoring of an electrical parameter that reflects a biomolecule parameter. For clarity, FIG. 22 is not drawn to scale, as the pair of facing electrodes may be positioned so that single stranded DNA passes between tips in a base-by-base translocation so that the tunneling detector measures an electrical parameter for individual bases within the biomolecule, thereby providing sequence information for the biomolecule (see also FIG. 20(a)).

REFERENCES

Thomas, P. D. & Kejariwal, A. Coding single-nucleotide polymorphisms associated with complex vs. Mendelian disease: Evolutionary evidence for differences in molecular effects. Proc. Natl. Acad. Sci. USA 101, 15398-15403 (2004).

The International HapMap, C. A haplotype map of the human genome. Nature 437, 1299-1320 (2005).

Mardis, E. R. Next-Generation DNA Sequencing Methods. Annu. Rev. Genom. Human Genet. 9, 387-402 (2008).

Metzker, M. L. Sequencing technologies—the next generation. Nat. Rev. Genet. 11, 31-46 (2010).

http://www.genome.gov/12513210.

Coulter, W. H. Means for counting particles suspended in a fluid. U.S. Pat. No. 2,656,508 (1953).

Church, G., Deamer, D. W., Branton, D., Baldarelli, R. & Kasianowicz, J. Characterization of individual polymer molecules based on monomer-interface interactions. U.S. Pat. No. 5,795,782 (1995).

Deamer, D. W. & Branton, D. Characterization of Nucleic Acids by Nanopore Analysis. Acc. Chem. Res. 35, 817-825 (2002).

Rhee, M. & Burns, M. A. Nanopore sequencing technology: research trends and applications. Trends Biotechnol. 24, 580-586 (2006).

Dekker, C. Solid-state nanopores. Nat. Nanotechnol. 2, 209-215 (2007).

Healy, K. Nanopore-based single-molecule DNA analysis. Nanomedicine 2, 459-481 (2007).

Branton, D. & et al. The potential and challenges of nanopore sequencing. Nat. Biotechnol. 26, 1146 (2008). This review article assesses the feasibility of various nanopore sequencing techniques that are currently under development (both optical and electrical).

Deamer, D. W. Nanopore analysis of nucleic acids bound to exonucleases and polymerases. Annu Rev Biophys 39, 79-90 (2010). This review article provides a historical perspective on the field of nanopore DNA sequencing and elaborates on nanopore based enzyme mediated sequencing approaches.

Iqbal, S. & Bashir, R. Nanopores: Sensing and Fundamental Biological Interactions, Edn. 1. (Springer, New York, 2011).

Kasianowicz, J. J., Brandin, E., Branton, D. & Deamer, D. W. Characterization of individual polynucleotide molecules using a membrane channel. Proc. Natl. Acad. Sci. USA 93, 13770-13773 (1996).

16. Akeson, M., Branton, D., Kasianowicz, J. J., Brandin, E. & Deamer, D. W. Microsecond Time-Scale Discrimination Among Polycytidylic Acid, Polyadenylic Acid, and Polyuridylic Acid as Homopolymers or as Segments Within Single RNA Molecules. Biophys. J. 77, 3227-3233 (1999).

Meller, A. & Branton, D. Single molecule measurements of DNA transport through a nanopore. Electrophoresis 23, 2583-2591 (2002).

Benner, S. et al. Sequence-specific detection of individual DNA polymerase complexes in real time using a nanopore. Nat. Nanotechnol. 2, 718-724 (2007).

Cockroft, S. L., Chu, J., Amorin, M. & Ghadiri, M. R. A Single-Molecule Nanopore Device Detects DNA Polymerase Activity with Single-Nucleotide Resolution. J. Am. Chem. Soc. 130, 818-820 (2008).

Lieberman, K. R. et al. Processive Replication of Single DNA Molecules in a Nanopore Catalyzed by phi29 DNA Polymerase. J. Am. Chem. Soc. 132, 17961-17972 (2010). A polymerase coupled to a nanopore as shown here, could be used for both strand sequencing as well as mechanistic studies of enzyme function.

Olasagasti, F. et al. Replication of individual DNA molecules under electronic control using a protein nanopore. Nat. Nanotechnol. 5, 798-806 (2010).

Rincon-Restrepo, M., Mikhailova, E., Bayley, H. & Maglia, G. Controlled Translocation of Individual DNA Molecules through Protein Nanopores with Engineered Molecular Brakes. Nano Lett. 11, 746-750 (2011).

Mitchell, N. & Howorka, S. Chemical Tags Facilitate the Sensing of Individual DNA Strands with Nanopores13. Angew. Chem. Int. Ed. 47, 5565-5568 (2008).

Clarke, J. et al. Continuous base identification for single-molecule nanopore DNA sequencing. Nat. Nanotechnol. 4, 265-270 (2009). This study forms the basis for Oxford Nanopore's sequencing by exonuclease digestion approach using biological α-hemolysin.

Stoddart, D., Heron, A. J., Mikhailova, E., Maglia, G. & Bayley, H. Single-nucleotide discrimination in immobilized DNA oligonucleotides with a biological nanopore. Proc. Natl. Acad. Sci. USA 106, 7702-7707 (2009).

Faller, M., Niederweis, M. & Schulz, G. E. The Structure of a Mycobacterial Outer-Membrane Channel. Science 303, 1189-1192 (2004).

Derrington, I. M. et al. Nanopore DNA sequencing with MspA. Proc. Natl. Acad. Sci. USA 107, 16060-16065 (2010). Proof-of-principle experiments demonstrating DI sequencing using MspA are shown in this work.

Wendell, D. et al. Translocation of double-stranded DNA through membrane-adapted phi29 motor protein nanopores. Nat. Nanotechnol. 4, 765-772 (2009).

Jing, P., Hague, F., Shu, D., Montemagno, C. & Guo, P. X. One-Way Traffic of a Viral Motor Channel for Double-Stranded DNA Translocation. Nano Lett. 10, 3620-3627 (2010).

Groves, J. T., Ulman, N. & Boxer, S. G. Micropatterning fluid lipid bilayers on solid supports. Science 275, 651-653 (1997).

Mager, M. D. & Melosh, N. A. Nanopore-Spanning Lipid Bilayers for Controlled Chemical Release. Adv. Mater. 20, 4423-4427 (2008).

White, R. J. et al. Ionic conductivity of the aqueous layer separating a lipid bilayer membrane and a glass support. Langmuir 22, 10777-10783 (2006).

Venkatesan, B. M. et al. Lipid bilayer coated $Al_2O_3$ nanopore sensors: towards a hybrid biological solid-state nanopore. Biomed. Microdevices, 1-12 (2011).

Chung, M. & Boxer, S. G. Stability of DNA-Tethered Lipid Membranes with Mobile Tethers. Langmuir 27, 5492-5497 (2011).

Langford, K. W., Penkov, B., Derrington, I. M. & Gundlach, J. H. Unsupported planar lipid membranes formed from mycolic acids of *Mycobacterium tuberculosis*. J. Lipid Res. 52, 272-277 (2011).

Knoll, W., Köper, I., Naumann, R. & Sinner, E.-K. Tethered bimolecular lipid membranes—A novel model membrane platform. Electrochim. Acta 53, 6680-6689 (2008).

Storm, A. J., Chen, J. H., Ling, X. S., Zandbergen, H. W. & Dekker, C. Fabrication of solid-state nanopores with single nanometer precision. Nat. Mater. 2, 537-540 (2003).

Venkatesan, B. M. et al. Highly Sensitive, Mechanically Stable Nanopore Sensors for DNA Analysis. Adv. Mater. 21, 2771-2776 (2009).

Kim, M. J., Wanunu, M., Bell, D. C. & A. Meller Rapid Fabrication of Uniformly Sized Nanopores and Nanopore Arrays for Parallel DNA Analysis. Adv. Mater. 18, 3149-3153 (2006).

Nam, S.-W., Rooks, M. J., Kim, K.-B. & Rossnagel, S. M. Ionic Field Effect Transistors with Sub-10 nm Multiple Nanopores. Nano Lett. 9, 2044-2048 (2009).

McNally, B. et al. Optical Recognition of Converted DNA Nucleotides for Single-Molecule DNA Sequencing Using Nanopore Arrays. Nano Lett. 10, 2237-2244 (2010). Each nucleotide is converted to a preset nucleotide specific sequence and hybridized with fluorescent probes. Hybridized probes are sequentially cleaved off during transport through <2 nm diameter pores allowing optical sequence read out.

Li, J. et al. Ion-beam sculpting at nanometre length scales. Nature 412, 166-169 (2001).

Salisbury, I. G., Timsit, R. S., Berger, S. D. & Humphreys, C. J. Nanometer scale electron beam lithography in inorganic materials. Appl. Phys. Lett. 45, 1289-1291 (1984).

Healy, K., Schiedt, B. & Morrison, A. P. Solid-state nanopore technologies for nanopore-based DNA analysis. Nanomedicine 2, 875-897 (2007).

Venkatesan, B. M., Shah, A. B., Zuo, J. M. & Bashir, R. DNA Sensing Using Nanocrystalline Surface-Enhanced $Al_2O_3$ Nanopore Sensors. Adv. Funct. Mater. 20, 1266-1275 (2010).

Hoogerheide, D. P., Garaj, S. & Golovchenko, J. A. Probing Surface Charge Fluctuations with Solid-State Nanopores. Phys. Rev. Lett. 102, 256804 (2009).

George, S. M. Atomic Layer Deposition: An Overview. Chem. Rev. 110, 111-131 (2009).

Geim, A. K. Graphene: Status and Prospects. Science 324, 1530-1534 (2009).

Fischbein, M. D. & Drndic, M. Electron beam nanosculpting of suspended graphene sheets. Appl. Phys. Lett. 93, 113107-113103 (2008). This is the first report of nanopore fabrication in a suspended graphene sheet using a focused convergent electron beam and has served as the inspiration for subsequent studies involving DNA transport through graphene nanopores.

Girit, Ç. Ö. et al. Graphene at the Edge: Stability and Dynamics. Science 323, 1705-1708 (2009).

Garaj, S. et al. Graphene as a subnanometre trans-electrode membrane. Nature 467, 190-193 (2010).

Merchant, C. A. et al. DNA Translocation through Graphene Nanopores. Nano Lett. 10, 2915-2921 (2010). Along with experimental data showing DNA translocation through a graphene monolayer nanopore, this paper importantly calculates the theoretical spatial resolution of a monolayer thin graphene nanopore sensor.

Schneider, G. g. F. et al. DNA Translocation through Graphene Nanopores. Nano Lett. 10, 3163-3167 (2010).

Hall, J. E. Access resistance of a small circular pore. J. Gen. Physiol. 66, 531-532 (1975).

Song, B. et al. Atomic-Scale Electron-Beam Sculpting of Near-Defect-Free Graphene Nanostructures. Nano Lett. 11, 2247-2250 (2011).

Li, J., Gershow, M., Stein, D., Brandin, E. & Golovchenko, J. A. DNA molecules and configurations in a solid-state nanopore microscope. Nat. Mater. 2, 611-615 (2003).

Storm, A. J. et al. Fast DNA Translocation through a Solid-State Nanopore. Nano Lett. 5, 1193-1197 (2005).

Wanunu, M., Morrison, W., Rabin, Y., Grosberg, A. Y. & Meller, A. Electrostatic focusing of unlabelled DNA into nanoscale pores using a salt gradient. Nat. Nanotechnol. 5, 160-165 (2010).

Cahn, G. A. & Croce, C. M. MicroRNA signatures in human cancers. Nat. Rev. Cancer 6, 857-866 (2006).

Volinia, S. et al. A microRNA expression signature of human solid tumors defines cancer gene targets. Proc. Natl. Acad. Sci. USA 103, 2257-2261 (2006).

Wanunu, M. et al. Rapid electronic detection of probe-specific microRNAs using thin nanopore sensors. Nat. Nanotechnol. 5, 807-814 (2010).

Strathdee, G. & Brown, R. Aberrant DNA methylation in cancer: potential clinical interventions. Expert Rev. Mol. Med. 4, 1-17 (2002).

Lee, W. H., Isaacs, W. B., Bova, G. S. & Nelson, W. G. CG island methylation changes near the GSTP1 gene in prostatic carcinoma cells detected using the polymerase chain reaction: A new prostate cancer biomarker. Cancer Epidem. Biomar. 6, 443-450 (1997).

Laird, P. W. The power and the promise of DNA methylation markers. Nat. Rev. Cancer 3, 253-266 (2003).

Mirsaidov, U. et al. Nanoelectromechanics of Methylated DNA in a Synthetic Nanopore. Biophys. J. 96, L32-L34 (2009).

Wanunu, M. et al. Discrimination of Methylcytosine from Hydroxymethylcytosine in DNA Molecules. J. Am. Chem. Soc. 133, 486-492 (2010).

Botstein, D. & Risch, N. Discovering genotypes underlying human phenotypes: past successes for mendelian disease, future approaches for complex disease. Nat. Genet. (2003).

Zhao, Q. et al. Detecting SNPs Using a Synthetic Nanopore. Nano Lett. 7, 1680-1685 (2007).

Singer, A. et al. Nanopore Based Sequence Specific Detection of Duplex DNA for Genomic Profiling. Nano Lett. 10, 738-742 (2010).

Iqbal, S. M., Akin, D. & Bashir, R. Solid-state nanopore channels with DNA selectivity. Nat. Nanotechnol. 2, 243-248 (2007).

Wanunu, M. & Meller, A. Chemically Modified Solid-State Nanopores. Nano Lett. 7, 1580-1585 (2007).

Siwy, Z. S. & Howorka, S. Engineered voltage-responsive nanopores. Chem. Soc. Rev. 39, 1115-1132 (2009).

Kowalczyk, S. W. et al. Single-molecule transport across an individual biomimetic nuclear pore complex. Nat. Nanotechnol. advance online publication (2011).

Yusko, E. G. et al. Controlling protein translocation through nanopores with bio-inspired fluid walls. Nat. Nanotechnol. 6, 253-260 (2011).

Hall, A. R. et al. Hybrid pore formation by directed insertion of alpha-haemolysin into solid-state nanopores. Nat. Nanotechnol. 5, 874-877 (2010).

Vercoutere, W. et al. Rapid discrimination among individual DNA hairpin molecules at single-nucleotide resolution using an ion channel. Nat. Biotech. 19, 248-252 (2001).

Eid, J. et al. Real-Time DNA Sequencing from Single Polymerase Molecules. Science 323, 133-138 (2009).

Drmanac, R. et al. Human Genome Sequencing Using Unchained Base Reads on Self-Assembling DNA Nanoarrays. Science 327, 78-81 (2010).

http://www.iontorrent.com.

http://www.genome.gov/27527584.

Karnik, R., Duan, C., Castelino, K., Daiguji, H. & Majumdar, A. Rectification of Ionic Current in a Nanofluidic Diode. Nano Lett. 7, 547-551 (2007).

Jin, X. & Aluru, N. Gated transport in nanofluidic devices. Microfluid. Nanofluid., 1-10 (2011).

Liu, H. et al. Translocation of Single-Stranded DNA Through Single-Walled Carbon Nanotubes. Science 327, 64-67 (2010).

Nelson, T., Zhang, B. & Prezhdo, O. V. Detection of Nucleic Acids with Graphene Nanopores Ab Initio Characterization of a Novel Sequencing Device. Nano Lett. 10, 3237-3242 (2010).

Min, S. K., Kim, W. Y., Cho, Y. & Kim, K. S. Fast DNA sequencing with a graphene-based nanochannel device. Nat. Nanotechnol. 6, 162-165 (2011).

Postma, H. W. C. Rapid Sequencing of Individual DNA Molecules in Graphene Nanogaps. Nano Lett. 10, 420-425 (2010).

Prasongkit, J., Grigoriev, A., Pathak, B., Ahuja, R. & Scheicher, R. H. Transverse Conductance of DNA Nucleotides in a Graphene Nanogap from First Principles. Nano Lett. 11, 1941-1945 (2011).

Luan, B. et al. Base-By-Base Ratcheting of Single Stranded DNA through a Solid-State Nanopore. Phys. Rev. Lett. 104, 238103 (2010). IBM's DNA transistor architecture and proposed approach to nanopore based single molecule DNA sequencing are presented here.

Huang, S. et al. Identifying single bases in a DNA oligomer with electron tunnelling. Nat. Nanotechnol. 5, 868-873 (2010).

Zwolak, M. & Di Ventra, M. Colloquium: Physical approaches to DNA sequencing and detection. Rev. Mod. Phys. 80, 141-165 (2008).

Tanaka, H. & Kawai, T. Partial sequencing of a single DNA molecule with a scanning tunnelling microscope. Nat. Nanotechnol. 4, 518-522 (2009).

Tsutsui, M., Taniguchi, M., Yokota, K. & Kawai, T. Identifying single nucleotides by tunnelling current. Nat. Nanotechnol. 5, 286-290 (2010). This is the first report of a nanofabricated gap junction being used to successfully discriminate individual nucleotides through electron tunneling measurements.

Taniguchi, M., Tsutsui, M., Yokota, K. & Kawai, T. Fabrication of the gating nanopore device. Appl. Phys. Lett. 95, 123701-123703 (2009).

Ivanov, A. P. et al. DNA Tunneling Detector Embedded in a Nanopore. Nano Lett. 11, 279-285 (2010).

Asmann, Y. W., Kosari, F., Wang, K., Cheville, J. C. & Vasmatzis, G. Identification of Differentially Expressed Genes in Normal and Malignant Prostate by Electronic Profiling of Expressed Sequence Tags. Cancer Res. 62, 3308-3314 (2002).

Feldman, A. L. et al. Discovery of recurrent t(6; 7)(p25.3; q32.3) translocations in ALK-negative anaplastic large cell lymphomas by massively parallel genomic sequencing. Blood 117, 915-919 (2010).

Meller, A., Nivon, L., Brandin, E., Golovchenko, J. & Branton, D. Rapid nanopore discrimination between single polynucleotide molecules. Proc. Natl. Acad. Sci. USA 97, 1079-1084 (2000).

Howorka, S., Cheley, S. & Bayley, H. Sequence-specific detection of individual DNA strands using engineered nanopores. Nat. Biotech. 19, 636-639 (2001).

Bates, M., Burns, M. & Meller, A. Dynamics of DNA Molecules in a Membrane Channel Probed by Active Control Techniques. Biophys. J. 84, 2366-2372 (2003).

Astier, Y., Braha, O. & Bayley, H. Toward Single Molecule DNA Sequencing: Direct Identification of Ribonucleoside and Deoxyribonucleoside 5'-Monophosphates by Using an Engineered Protein Nanopore Equipped with a Molecular Adapter. J. Am. Chem. Soc. 128, 1705-1710 (2006).

Borsenberger, V., Mitchell, N. & Howorka, S. Chemically Labeled Nucleotides and Oligonucleotides Encode DNA for Sensing with Nanopores. J. Am. Chem. Soc. 131, 7530-7531 (2009).

Chen, P. et al. Probing Single DNA Molecule Transport Using Fabricated Nanopores. Nano Lett. 4, 2293-2298 (2004).

Storm, A. J., Chen, J. H., Zandbergen, H. W. & Dekker, C. Translocation of double-strand DNA through a silicon oxide nanopore. Phys. Rev. E 71, 051903 (2005).

Fologea, D., Uplinger, J., Thomas, B., McNabb, D. S. & Li, J. Slowing DNA Translocation in a Solid-State Nanopore. Nano Lett. 5, 1734-1737 (2005).

Kim, Y. R. et al. Nanopore sensor for fast label-free detection of short double-stranded DNAs. Biosensors Bioelectron. 22, 2926-2931 (2007).

Wanunu, M., Sutin, J., McNally, B., Chow, A. & Meller, A. DNA Translocation Governed by Interactions with Solid-State Nanopores. Biophys. J. 95, 4716-4725 (2008).

Chen, Z. et al. DNA translocation through an array of kinked nanopores. Nat. Mater. 9, 667-675 (2010).

Ling, X. S., Bready, B. & Pertsinidis, A. Hybridization-assisted nanopore sequencing of nucleic acids. U.S. Pat. No. 2007 0190542 (2007). The HANS approach is being commercially developed by NABsys. 6-mer oligonucleotide probes are hybridized to ssDNA and current-vs-time traces are recorded as the complex translocates through the pore, spatially revealing the probe's position on the ssDNA template.

Lagerqvist, J., Zwolak, M. & Di Ventra, M. Fast DNA Sequencing via Transverse Electronic Transport. Nano Lett. 6, 779-782 (2006).

Heng, J. B. et al. Beyond the gene chip. Bell Labs Tech. J. 10, 5-22 (2005).

Gracheva, M. E. et al. Simulation of the electric response of DNA translocation through a semiconductor nanopore-capacitor. Nanotechnology 17, 622-633 (2006).

Sigalov, G., Corner, J., Timp, G. & Aksimentiev, A. Detection of DNA Sequences Using an Alternating Electric Field in a Nanopore Capacitor. Nano Lett. 8, 56-63 (2007).

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

Examples of documents incorporated specifically by reference to the extent the disclosure is not inconsistent with that provided herein include: Venkatesan et al. "Stacked Graphene-$Al_2O_3$ Nanopore Sensors for Sensitive Detection of DNA and DNA-Protein Complexes." ACS NANO 6(1): 441-450 (2012); PCT Pub. No. WO 2010/08061; U.S. Pat. Pub. Nos. 2012/0040343 and 2011/0226623.

When a Markush group or other grouping is used herein, all individual members of the group and all combinations and subcombinations possible of the group are intended to be individually included in the disclosure. Every formulation or combination of components described or exemplified can be used to practice the invention, unless otherwise stated. Whenever a range is given in the specification, for example, a number range, a voltage range, or a velocity range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

TABLE 1

Nanopore sequencing techniques and potential challenges:

| Sensing Modality | Description of Technique | Potential Challenges |
| --- | --- | --- |
| Ionic Current | Hybridization assisted nanopore sequencing | High spatial resolution required, Complex algorithms needed for analysis |
| | Sequencing by exonuclease digestion | Requires sequential passage of mononucleotides in order in which they are cleaved |
| | Sequencing by synthesis | Retaining processing enzymes (DNA polymerase) at the pore, Achieving long read lengths and maintaining enzyme activity under a voltage load |
| | Duplex Interrupted (DI) DNA sequencing | Converting large genomic ssDNA fragments to DI structure |
| Optical Readout | Optical recognition of converted DNA | Complex and error-prone DNA conversion steps, High density <2 nm nanopore arrays needed |
| Transverse election tunneling | Tunneling detector on a nanopore (Metal, Graphene, Carbon Nanotubes) | Precisely controlling orientation and position of nucleotides in the gap, Slow transiocation rates required to sufficiently sample over noise, Nucleotide dependent tunneling currents need to be measured in solution |
| Capacitive Sensing | Metal-Oxide-Semiconductor nanopore capacitor | Must operate in high ionic strength solution with negligible drift and leakage, DNA translocation rates need to be substantially reduced |

We claim:

1. A method for characterizing a biomolecule parameter, said method comprising the steps of:
   providing a nanopore in a membrane comprising a conductor-dielectric stack, wherein said membrane separates a first fluid compartment from a second fluid compartment and said nanopore fluidly connects said first and said second fluid compartments and said conductor comprises graphene or an atomically thin electrically conducting layer of Molybdenum disulfide ($MoS_2$), doped silicon, silicene, or ultra-thin metal;
   providing the biomolecule to said first fluid compartment;
   applying an electric field across said membrane;
   driving said biomolecule through said nanopore to said second fluid compartment under said applied electric field;
   monitoring an electrical parameter across the membrane or along a plane formed by the membrane as the biomolecule transits the nanopore, thereby characterizing said biomolecule parameter; and
   synthesizing a polynucleotide sequence by adding nucleotides to the biomolecule that is transiting the nanopore, thereby providing sequencing by synthesis; wherein the sequencing by synthesis is by a polymerase anchored to the conductor-dielectric stack and the added nucleotides and reagents are from a source of nucleotides in the first or second fluid compartment, and the sequencing by synthesis further comprises the step of detecting released $H^+$ or pyrophosphates during addition of a nucleotide to the biomolecule transiting the pore, and the detecting released $H^+$ or pyrophosphates is by measuring a change in nanopore current.

2. A method for characterizing a biomolecule parameter, said method comprising the steps of:
   providing a nanopore in a membrane comprising a conductor-dielectric stack, wherein said membrane separates a first fluid compartment from a second fluid compartment and said nanopore fluidly connects said first and said second fluid compartments and said conductor comprises graphene or an atomically thin electrically conducting layer of Molybdenum disulfide ($MoS_2$), doped silicon, silicene, or ultra-thin metal;
   providing the biomolecule to said first fluid compartment;
   applying an electric field across said membrane;
   driving said biomolecule through said nanopore to said second fluid compartment under said applied electric field;
   monitoring an electrical parameter across the membrane or along a plane formed by the membrane as the biomolecule transits the nanopore, thereby characterizing said biomolecule parameter; and
   wherein the electrical parameter is measured by field effect gating or field effect sensing by a graphene layer electrically insulated from the fluid in the fluid compartment and in the nanopore.

3. The method of claim 1, wherein said conductor comprises graphene.

4. The method of claim 2, wherein said conductor comprises graphene.

* * * * *